US007148398B2

(12) United States Patent
Bougri et al.

(10) Patent No.: US 7,148,398 B2
(45) Date of Patent: Dec. 12, 2006

(54) ACQUIRED RESISTANCE GENES IN PLANTS

(75) Inventors: Oleg V. Bougri, Germantown, MD (US); Caius M. T. Rommens, Chesterfield, MO (US); Neelam Srivastava, Ann Arbor, MI (US); Kathleen M. M. Swords, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/151,373

(22) Filed: Jun. 13, 2005

(65) Prior Publication Data

US 2005/0235380 A1 Oct. 20, 2005

Related U.S. Application Data

(60) Continuation of application No. 10/318,780, filed on Dec. 13, 2002, now Pat. No. 7,030,293, which is a division of application No. 09/569,804, filed on May 12, 2000, now Pat. No. 6,506,962.

(60) Provisional application No. 60/133,965, filed on May 13, 1999.

(51) Int. Cl.

| | |
|---|---|
| ***C12N 15/09*** | (2006.01) |
| ***C12N 15/29*** | (2006.01) |
| ***C12N 15/82*** | (2006.01) |
| *A01H 5/00* | (2006.01) |
| *C12N 15/00* | (2006.01) |

(52) U.S. Cl. ...................... 800/279; 800/278; 800/295; 800/298; 435/320.1; 435/468; 536/23.6

(58) Field of Classification Search ................ 800/279, 800/278, 298, 295; 435/320.1, 468; 536/23.6
See application file for complete search history.

(56) References Cited

FOREIGN PATENT DOCUMENTS

| | | |
|---|---|---|
| WO | WO 94/16077 | 7/1994 |
| WO | WO 97/49822 | 12/1997 |
| WO | WO 98/06748 | 2/1998 |
| WO | WO 98/26082 | 6/1998 |
| WO | WO 99/14350 | 3/1999 |
| WO | WO 00/28036 | 5/2000 |

OTHER PUBLICATIONS

Cao et al., The Arabidopsis *NPR1* Gene that Controls systemic Acquired Resistance Encodes a Novel Protein Containing Ankyrin Repeats, *Cell 88*:57-63 (1997).

Cao et al., Characterization of an Arabidopsis Mutant That Is Nonresponsive to Inducers of Systemic Acquired Resistance, *The Plant Cell 6*:1583-1592 (1994).

Delaney et al., *Arabidopsis* signal transduction mutant defective in chemically and biologically induced disease resistance, *Proc. Natl. Acad. Sci. USA 92*:6602-6606 (1995).

Gorlach et al., Benzothiadiazole, a Novel Class of Inducers of Systemic Acquired Resistance, Activates Gene Expression and Disease Resistance in Wheat, *The Plant Cell 8*:629-643 (1996).

Hwang et al., Induced Resistance of Spring Barley to *Erysiphe granimis f.* sp. *Hordei, Phytopath. Z. 103*:41-47 (1982).

Kadyrzhanova et al., Sequences for STS primer sets, Database *Embl. Sequence Library*, Accession No. L43984 (1995).

Kmecl et al., Quantitative field resistance of wheat to powdery mildew and defense reactions at the seedling stage: identification of a potential marker, *Physiological and Molecular Plant Pathology 47*:185-199 (1995).

Linthorst et al., Constitutive Expression of Pathogenesis-Related Proteins PR-1, GRP and PR-S in Tobacco has no Effect on Virus Infection, *American Society of Plant Physiologists 1*:285-291 (1989).

Morris et al., Induced Resistance Responses in Maize, *Mol. Plant Microbe Interact 11*:643-658 (1998).

Ryals et al., The Arabidopsis *NIM1* Protein Shows Homology to the Mammalian Transcription Factor Inhibitor IkB, *The Plant Cell 9*:425-439 (1997).

Ryals et al., *The Plant Cell 8*:1809-1819 (1996).

Sasaki, Rice cDNA from Callus 1995, Database, *Dbest Database*, Genbank Accession No. D40521 (1994).

Schweizer et al., cDNA cloning, in vitro transcription and partial sequence analysis of mRNAs from winter wheat (*Triticum aestivum L.*) with induced resistance to *Erysiphe graminis f.* sp. *Tritici, Plant Molecular Biology 12*:643-654 (1989).

Smith et al., *Pseudomonas syringae* pv. *Syringae* induces systemic resistance to *Pyricularia oryzae* in rice, *Physiological and Molecular Plant Pathology 39*:451-461 (1991).

Ushimia et al., On nucleotide sequence of Oryza sativa, Database, *Embl. Sequence Library*, Accession No. D42201 (1998).

*Primary Examiner*—Medina A. Ibrahim
(74) *Attorney, Agent, or Firm*—Timothy K. Ball, Esq.

(57) ABSTRACT

The invention provides acquired resistance genes isolated from plants, and methods of using the genes to produce disease resistant transgenic plants.

8 Claims, 13 Drawing Sheets

3b

3a 1 2 3 4 5

SEQUENCE LISTING

```
<160> NUMBER OF SEQ ID NOS: 36

<210> SEQ ID NO 1
<211> LENGTH: 1428
<212> TYPE: DNA
<213> ORGANISM: Oryza sativa

<400> SEQUENCE: 1

atggaggagc tcgtgccggg aggccgcgtg gggcgcgacg ccttcctgtc gctgctgggt     60

tacctgtaca cgggcaagct ccggccggcg ccggatgacg tggtgtcctg cgccgacccc    120

atgtgcccgc acgactcgtg cccgccggcg atcaggttca acgtcgagca aatgtacgcg    180

gcgtgggcgt tcaagatcac cgagctcatc tcgctgttcc agcgacggct tcttaacttc    240

gtcgataaga ctctagtaga agatgttctt ccaattctgc aagttgcttt tcattcagag    300

ctgactccag tgcttgaaaa atgtattcgg agaattgcaa gatcaaatct tgataatgta    360

tcgttggata aggaacttcc tccagaagtt gctgttcaga taaaagagat tcgccaaaaa    420

tctcagccaa atgagggtga cactgtcatt tcagaccctg tacatgagaa aagggtcaga    480

agaatccaca gggcactgga ttctgatgat gttgagcttg tgaagttgct tcttaacgag    540

tctgagatca ccttggatga tgccaatgca ttgcactatg ctgctgctta ctgtgattcg    600

aaagttgttt cggagttgtt agacttgaga cttgccaact tgaatttgaa gaattcgcgt    660

ggatacacgg cactccatct ggctgctatg aggagagagc cagctattat catgtgtctc    720

ctaaacaaag gagcagctgt atcacaattg actgctgatg gccagagtgc aatgagtatc    780

tgccggaggt taacaaggtt gaaagactac aatacaaaga tggagcaagg ccaagagtca    840
```

-continued

```
aacaaagaca ggttatgtat tgatatatta gatagggaga tgataaggaa acctatggca    900

gtggaagatt ctgtcacctc gcctttgttg gctgacgatc ttcacatgaa gcttctctac    960

cttgaaaaca gagttgcatt tgcaagatta ttttttcctg cagaagcaaa ggttgcaatg   1020

caaattgcac aagcagacac cacaccagaa tttggcattg ttcctgcagc tagcacttct   1080

ggaaaattga aggaagtcga tctgaacgag acaccagtaa cacaaaacaa aaggctccgt   1140

tcaagggtgg atgcactcat gaaaacagtt gagctgggac gtcgctactt ccctaactgc   1200

tcgcaggtgc tcgacaaatt tctggaggat gatttgcccg atagtcctga tgcactcgac   1260

ctccaaaatg gcacttctga tgagcaaaat gttaaaagga tgcggttctg tgagttaaag   1320

gaggatgtgc gcaaggcatt cagcaaagcc agagctgata atagcatgtt ttctatcttg   1380

tcatcttcat cgtcctcttc gccacctccc aaggttgcaa agaaatga                1428
```

<210> SEQ ID NO 2
<211> LENGTH: 2368
<212> TYPE: DNA
<213> ORGANISM: Oryza sativa

<400> SEQUENCE: 2

```
ttaaaataaa aacgagcgtc ttatcctttt ggtataacat gtagccgcca tgctgtttac     60

acgacccaaa ttacagccat ttacctccgg attgacctca agaaaacaaa ccttccgcag    120

cagagacgga actgttatcc agaacctcca tggtgctcaa ctctcaccga agaaatttat    180

aatgatacat ctggcaatta gtccaaacaa ggttggcacc ccagacttca aagctgcaac    240

agcttaatcc agcataccgg aaagtcggtc caacaataac catgaaaatt gatgagcacc    300

aacaattacc aacattagac aagtcattcc ggaagcacca tgtaatgagc acagtgatca    360

cagcaaaaca tcatcttctt gcttcagatg tcaagatccc agacggccac ctcaaccaag    420

tttgattcgc aagaatactc ctttcttcgg gtgacttcag gttgaacttg tcttcaggtc    480

accttaaaac gacgagagaa tgctacaatt tcttggttgt tgcgctgtag ctccacgttt    540

agattcacgc gcgatcgttg aacgatgtag tcgcagtggg atctgagaga gaggactggg    600

gggaggccgc ggtacaagat ggaggagctc gtgccgggag gccgcgtggg gcgcgacgcc    660

ttcctgtcgc tgctgggtta cctgtacacg ggcaagctcc ggccggcgcc ggatgacgtg    720

gtgtcctgcg ccgaccccat gtgcccgcac gactcgtgcc cgccggcgat caggttcaac    780

gtcgagcaaa tgtacgcggc gtgggcgttc aagatcaccg agctcatctc gctgttccag    840

cgacggcttc ttaacttcgt cgataagact ctagtagaag atgttcttcc aattctgcaa    900

gttgcttttc attcagagct gactccagtg cttgaaaaat gtattcggag aattgcaaga    960

tcaaatcttg ataatgtatc gttggataag gaacttcctc cagaagttgc tgttcagata   1020

aaagagattc gccaaaaatc tcagccaaat gagggtgaca ctgtcatttc agaccctgta   1080

catgagaaaa gggtcagaag aatccacagg gcactggatt ctgatgatgt tgagcttgtg   1140

aagttgcttc ttaacgagtc tgagatcacc ttggatgatg ccaatgcatt gcactatgct   1200

gctgcttact gtgattcgaa agttgtttcg gagttgttag acttgagact tgccaacttg   1260

aatttgaaga attcgcgtgg atacacggca ctccatctgg ctgctatgag gagagagcca   1320

gctattatca tgtgtctcct aaacaaagga gcagctgtat cacaattgac tgctgatggc   1380

cagagtgcaa tgagtatctg ccggaggtta acaaggttga aagactacaa tacaaagatg   1440

gagcaaggcc aagagtcaaa caaagacagg ttatgtattg atatattaga tagggagatg   1500

ataaggaaac ctatggcagt ggaagattct gtcacctcgc ctttgttggc tgacgatctt   1560
```

-continued

```
cacatgaagc ttctctacct tgaaaacaga gttgcatttg caagattatt ttttcctgca   1620

gaagcaaagg ttgcaatgca aattgcacaa gcagacacca caccagaatt tggcattgtt   1680

cctgcagcta gcacttctgg aaaattgaag gaagtcgatc tgaacgagac accagtaaca   1740

caaaacaaaa ggctccgttc aagggtggat gcactcatga aaacagttga gctgggacgt   1800

cgctacttcc ctaactgctc gcaggtgctc gacaaatttc tggaggatga tttgcccgat   1860

agtcctgatg cactcgacct ccaaaatggc acttctgatg agcaaaatgt taaaaggatg   1920

cggttctgtg agttaaagga ggatgtgcgc aaggcattca gcaaagccag agctgataat   1980

agcatgtttt ctatcttgtc atcttcatcg tcctcttcgc cacctcccaa ggttgcaaag   2040

aaatgacaga agttttgtaa caaatttccg ctcgtgatgt tactgggaca agagatatcg   2100

atcaatagac ctgtatagtc ttacagtggt ataacaatta gatatcgaag cttcttcgaa   2160

tattagaaag tgctgttctg ggctgcactc agctggttta tgggacccat gcggtgaaac   2220

tggcaaaaga aaaccagctg attagaggct ccaaagtagt gtctctcgtg aatatgtttg   2280

tagcattctg ttttgttcag gatggctgta atgataaaat cttttcaata gatatatagc   2340

taattgtctc gtaaaaaaaa aaaaaaaa                                      2368
```

<210> SEQ ID NO 3
<211> LENGTH: 705
<212> TYPE: DNA
<213> ORGANISM: Oryza sativa

<400> SEQUENCE: 3

```
cacagggcgt tggataggga tgatgttgag cttgtgaagt tgcttcttaa cgaatctgag     60

atcaccttgg atgatgccaa tgcattgcac tatgctgctg cttactgtga ttcgaaagtt    120

gtttcggagt tgttagactt gagacttgcc aacttgaatt tgaagaattc gcgtggatac    180

acggcactcc atctggctgc tatgaggaga gagccagcta ttatcatgtg tctcctaaac    240

aaaggagcag ctgtatcaca attgactgct gatggccaga gtgcaatgag tatctgccgg    300

aggttaacaa ggatgaaaga ctacaataca aagatggagc aaggccaaga gtcaaacaaa    360

gacagattat gtattgatat attagatagg gagatgataa ggaaacctat ggcagtggaa    420

gattctgtca cctcgccttt gttggctgac gatcttcaca tgaagcttct ctaccttgaa    480

aacagagttg catttgcaag attatttttt cctgcagaag caaaggttgc aatgcaaatt    540

gcacaagcag acaccacacc agaatttggc attgttcctg cagctagcac ttctggaaaa    600

ttgaaggaag tcgatctgaa cgagacacca gtaacacaaa acaaaaggct ccgttcaagg    660

gtggatgcac tcatgaaaac agtcgaactc ggcccaccgc ttctt                    705
```

<210> SEQ ID NO 4
<211> LENGTH: 475
<212> TYPE: PRT
<213> ORGANISM: Oryza sativa

<400> SEQUENCE: 4

```
Met Glu Glu Leu Val Pro Gly Gly Arg Val Gly Arg Asp Ala Phe Leu
  1               5                  10                  15

Ser Leu Leu Gly Tyr Leu Tyr Thr Gly Lys Leu Arg Pro Ala Pro Asp
             20                  25                  30

Asp Val Val Ser Cys Ala Asp Pro Met Cys Pro His Asp Ser Cys Pro
         35                  40                  45

Pro Ala Ile Arg Phe Asn Val Glu Gln Met Tyr Ala Ala Trp Ala Phe
```

-continued

```
    50                  55                  60

Lys Ile Thr Glu Leu Ile Ser Leu Phe Gln Arg Arg Leu Leu Asn Phe
65                  70                  75                  80

Val Asp Lys Thr Leu Val Glu Asp Val Leu Pro Ile Leu Gln Val Ala
                85                  90                  95

Phe His Ser Glu Leu Thr Pro Val Leu Glu Lys Cys Ile Arg Arg Ile
            100                 105                 110

Ala Arg Ser Asn Leu Asp Asn Val Ser Leu Asp Lys Glu Leu Pro Pro
        115                 120                 125

Glu Val Ala Val Gln Ile Lys Glu Ile Arg Gln Lys Ser Gln Pro Asn
    130                 135                 140

Glu Gly Asp Thr Val Ile Ser Asp Pro Val His Glu Lys Arg Val Arg
145                 150                 155                 160

Arg Ile His Arg Ala Leu Asp Ser Asp Asp Val Glu Leu Val Lys Leu
                165                 170                 175

Leu Leu Asn Glu Ser Glu Ile Thr Leu Asp Asp Ala Asn Ala Leu His
            180                 185                 190

Tyr Ala Ala Ala Tyr Cys Asp Ser Lys Val Val Ser Glu Leu Leu Asp
        195                 200                 205

Leu Arg Leu Ala Asn Leu Asn Leu Lys Asn Ser Arg Gly Tyr Thr Ala
    210                 215                 220

Leu His Leu Ala Ala Met Arg Arg Glu Pro Ala Ile Ile Met Cys Leu
225                 230                 235                 240

Leu Asn Lys Gly Ala Ala Val Ser Gln Leu Thr Ala Asp Gly Gln Ser
                245                 250                 255

Ala Met Ser Ile Cys Arg Arg Leu Thr Arg Leu Lys Asp Tyr Asn Thr
            260                 265                 270

Lys Met Glu Gln Gly Gln Glu Ser Asn Lys Asp Arg Leu Cys Ile Asp
        275                 280                 285

Ile Leu Asp Arg Glu Met Ile Arg Lys Pro Met Ala Val Glu Asp Ser
    290                 295                 300

Val Thr Ser Pro Leu Leu Ala Asp Asp Leu His Met Lys Leu Leu Tyr
305                 310                 315                 320

Leu Glu Asn Arg Val Ala Phe Ala Arg Leu Phe Phe Pro Ala Glu Ala
                325                 330                 335

Lys Val Ala Met Gln Ile Ala Gln Ala Asp Thr Thr Pro Glu Phe Gly
            340                 345                 350

Ile Val Pro Ala Ala Ser Thr Ser Gly Lys Leu Lys Glu Val Asp Leu
        355                 360                 365

Asn Glu Thr Pro Val Thr Gln Asn Lys Arg Leu Arg Ser Arg Val Asp
    370                 375                 380

Ala Leu Met Lys Thr Val Glu Leu Gly Arg Arg Tyr Phe Pro Asn Cys
385                 390                 395                 400

Ser Gln Val Leu Asp Lys Phe Leu Glu Asp Asp Leu Pro Asp Ser Pro
                405                 410                 415

Asp Ala Leu Asp Leu Gln Asn Gly Thr Ser Asp Glu Gln Asn Val Lys
            420                 425                 430

Arg Met Arg Phe Cys Glu Leu Lys Glu Asp Val Arg Lys Ala Phe Ser
        435                 440                 445

Lys Ala Arg Ala Asp Asn Ser Met Phe Ser Ile Leu Ser Ser Ser Ser
    450                 455                 460

Ser Ser Ser Pro Pro Pro Lys Val Ala Lys Lys
465                 470                 475
```

-continued

<210> SEQ ID NO 5
<211> LENGTH: 1824
<212> TYPE: DNA
<213> ORGANISM: Triticum aestivum

<400> SEQUENCE: 5
atggagccgt cgtcgtccat cacggtcgcc tcctcgtcgt cctacctgtc caacggctct 60
agcccctgct ccggcgctct ggcgccgctg cccgcggcgg acgggtgggg cggggctggg 120
ggagggggag ggagcagcag cagcgtcgag gctgtgagtc tgagtcgcct cagcagcaac 180
ctcgagcgcc tcctcctcga ttctgaactc gactgcagcg acgccgacgt cgacgtggcg 240
gacggcgggc cgcccatccc catccaccgc tgcatcctcg ccgcgcgcag cccccttcttc 300 cacgacctct tccgcgcccg cgggagccgc agtgatgggg cagtcaccgc ctccgcctcc 360
gccaccagtg gcggagcggg aggggatgtt accgggaggc cgcagtacaa gatggaggac 420
ctcgtcccag gtggccgtgt gggtcgcgag gccttcctgg cgttcatggg gtacctctac 480
acgggcaggc tccggccagc gccgctggac gtggtgtcat gtgctgatct tgtgtgcccg 540
cacgactcgt gcccgccggc catcaggttc gccgtcgagc tcatgtacgc ggcgtggacc 600
ttcaggatcc ccgagctcat gtcgctgttc cagcgacggc ttatgaactt tgttgacaag 660
actctggctg aagacgtcct acctattttg caagttgctt tccactcgga gcttactcaa 720
gtgcgtgaaa aatgtgttca aaggattgca agatcggatc ttgatattat gtctttggat 780
aaggaactcc ttcccgaaat cgctgatgag ataaaaagaa tccgacagaa atctccccca 840
attgatggtg acaccatcat ttcggaccct atacacgaga aaagagtaag aagaatccac 900
agggcactgg attctgatga tgttgagctt gtgaagttgc ttcttaatga gtctgaaatc 960
accctagacg acgccaacgc attgcattat gctgcagctt actgcgattc taaagttctt 1020
acagagttgt taggcctgga acttgccaac ttgaatttga agaacagtcg tgggtacaca 1080
gcactccacc tagctgctat gaggagagaa ccagctatta ttatgtgtct cttaagcaaa 1140
ggagcagtgg cgtcgcaatt gacagatgat ggccgccttg caagtaatat ttgtcgaaga 1200
ttaacaagac taaaagatta caatgcaaag atggagcagg gccaagagtc aaataaagat 1260
aggatgtgca ttgacatcct agagagggag atgatgagga atcctatgac agcggaagat 1320
tcagtcacct cacctttatt ggctgatgat cttcacatga aactaagcta cctggaaaat 1380
agagtcgcgt ttgcaagatt attcttccct gctgaagcga aggttgcgat gcaaattgcg 1440
caagcagaca tcacaccaga agttggtggt ttttctgcag caagtacttc tggtaaactg 1500
agggaagtcg atctgaatga gacgccagta acaaaaaaca aaaggctacg ttcgagggtg 1560
gatgcactag tgaaaacagt ggaactgggc cgtcggtact tcccaaactg ctcgcaggtg 1620
ctcgacaaat tcttggaaga tggcctgcct gatggccttg atgcattcca gcagcaaagc 1680
ggcacccctg atgagcaaca ggtgaagaag atgcgcttct gcgaggtgaa ggaggacgtg 1740
cgcaaagcat acagcaaaga cacggccgat aacagcatgt tttcagccct gtcgtcaaac 1800
tcctcatcct cggcgatgaa gtga 1824

<210> SEQ ID NO 6
<211> LENGTH: 1830
<212> TYPE: DNA
<213> ORGANISM: Triticum aestivum

<400> SEQUENCE: 6

-continued

```
atggagccgt cgtcgtccat cacgttcgcc tcctcgtcgt cctacctgtc caacggctct     60
agcccctgct ccggcgctct ggcaccgctg cccgcggcgg acgggtgggg cgggggcggt    120
ggagggggag ggggagggag cagcagcagc gtcgaggccg tgagcttgaa tcgcctcagc    180
agcaacctcg agcgcctcct cctcgattct gaactcgact gcagcgacgc tgacgtcgac    240
gtcgcggacg gcggtccgcc catccccgtc caccgttgca tcctcgccgt gcgcagctcc    300
ttcttccacg acctcttccg cgcccgcggg agccgcagtg atggggccgt cactgcctct    360
gcctccgcca ccggaggcgg agcgggaggg gatgtgaacg ggaggccgca gtacaagatg    420
gaggacctcg tcccaggtgg ccgtgtgggc cgcgaggcct tcctagcgtt catggggtac    480
ctctacacgg gcaggctccg gccggcgccg ctggacgtgg tgtcatgtgc tgatcttgtg    540
tgcccgcacg actcgtgccc gccggctatc aggttcgccg tcgagctcat gtacgcggct    600
tggaccttca ggatccccga gctcatgtcg ctgttccagc gacggcttat gaactttgtt    660
gacaagactc tggcggaaga cgtcctacct attttgcaag ttgctttcca ctcggagctt    720
actcaagtgc gtgaaaaatg tgttcaaagg attgcaagat cggatcttga tattatgtct    780
ttggataagg aactccctcc agaaattgct gacgagataa aaaagatccg tcagaaatct    840
ccgccaattg atggtgacac catcatttcg gaccctgtac acgagaaaag agtaagaaga    900
atccacaggg cactggattc tgatgatgtt gaacttgtca agttgcttct taatgagtct    960
gaaatcaccc ttgacgacgc aaacgcattg cattatgctg cagcttactg cgattccaaa   1020
gttcttacag agttgttagg cctggaactt gccaacttga atttgaagaa cagtcgtggg   1080
tacacagcac tccacctagc tgctatgagg agagaaccag ctattattat gtgtctctta   1140
agcaaaggag cagtggcgtc gcaattgaca gatgacggcc gccttgcaag taatatttgt   1200
cgaaggttaa caagactaaa agattacaat gcgaagatgg agcagggcca agagtcaaat   1260
aaagatagga tgtgcattga catcctagag agggagatga tgaggaatcc tatgacagcg   1320
gaagattctg tcacctcacc tttattggct gatgatcttc acatgaaact aagctacctg   1380
gaaaacagag tcgcgttcgc aagactgttc ttccctgctg aagccaaggt tgccatgcaa   1440
attgcacaag cagacgtcac accagaagtt ggtggttttt ctgcagcaag tacttctggt   1500
aaactgaggg aagtcgatct gaatgagacg ccagtaacaa aaaacaaaag gctgcgttca   1560
agggtggatg cactagcgaa aacagtggaa ctgggccgtc ggtacttccc aaactgctcg   1620
caggtgctcg acaaattctt ggaagatggc ctgcctgatg gccttgatgc gttccagcag   1680
caaagcggca cccctgatga gcaacaggtg aagaagatgc gcttctgcga ggtgaaggag   1740
gacgtgcgca aagcatacag caaagacacg gccgataaca gcatgttttc ggccctgtcg   1800
tcaaactcct cgtcctcggc gatgaagtga                                    1830
```

<210> SEQ ID NO 7
<211> LENGTH: 2420
<212> TYPE: DNA
<213> ORGANISM: Triticum aestivum

<400> SEQUENCE: 7

```
gccgtccctt ctccgctgag tttaggcggg gggtgacgtg ggggagtttc cgtgccgacg     60
cggatctgcg tggtgccaaa caaagcctgc ccgaattgcg cagttcggcc gggagcgacc    120
aaaaggcagc ctcccccctt tgccttccca cacatggtgg tccggctcta gggccctttc    180
gcctcgtgct tggcggcggt gatggagccg tcgtcgtcca tcacggtcgc ctcctcgtcg    240
tcctacctgt ccaacggctc tagcccctgc tccggcgctc tggcgccgct gcccgcggcg    300
```

-continued

```
gacgggtggg gcggggctgg gggaggggga gggagcagca gcagcgtcga ggctgtgagt    360
ctgagtcgcc tcagcagcaa cctcgagcgc ctcctcctcg attctgaact cgactgcagc    420
gacgccgacg tcgacgtggc ggacggcggg ccgcccatcc ccatccaccg ctgcatcctc    480
gccgcgcgca gcccccttctt ccacgacctc ttccgcgccc gcgggagccg cagtgatggg    540
gcagtcaccg cctccgcctc cgccaccagt ggcggagcgg gaggggatgt taccgggagg    600
ccgcagtaca agatggagga cctcgtccca ggtggccgtg tgggtcgcga ggccttcctg    660
gcgttcatgg ggtacctcta cacgggcagg ctccggccag cgccgctgga cgtggtgtca    720
tgtgctgatc ttgtgtgccc gcacgactcg tgcccgccgg ccatcaggtt cgccgtcgag    780
ctcatgtacg cggcgtggac cttcaggatc cccgagctca tgtcgctgtt ccagcgacgg    840
cttatgaact ttgttgacaa gactctggct gaagacgtcc tacctatttt gcaagttgct    900
ttccactcgg agcttactca agtgcgtgaa aaatgtgttc aaaggattgc aagatcggat    960
cttgatatta tgtctttgga taaggaactc cttcccgaaa tcgctgatga gataaaaaga   1020
atccgacaga aatctccccc aattgatggt gacaccatca tttcggaccc tatacacgag   1080
aaaagagtaa gaagaatcca cagggcactg gattctgatg atgttgagct tgtgaagttg   1140
cttcttaatg agtctgaaat caccctagac gacgccaacg cattgcatta tgctgcagct   1200
tactgcgatt ctaaagttct tacagagttg ttaggcctgg aacttgccaa cttgaatttg   1260
aagaacagtc gtgggtacac agcactccac ctagctgcta tgaggagaga accagctatt   1320
attatgtgtc tcttaagcaa aggagcagtg gcgtcgcaat tgacagatga tggccgcctt   1380
gcaagtaata tttgtcgaag attaacaaga ctaaaagatt acaatgcaaa gatggagcag   1440
ggccaagagt caaataaaga taggatgtgc attgacatcc tagagaggga gatgatgagg   1500
aatcctatga cagcggaaga ttcagtcacc tcacctttat tggctgatga tcttcacatg   1560
aaactaagct acctggaaaa tagagtcgcg tttgcaagat tattcttccc tgctgaagcg   1620
aaggttgcga tgcaaattgc gcaagcagac atcacaccag aagttggtgg tttttctgca   1680
gcaagtactt ctggtaaact gagggaagtc gatctgaatg agacgccagt aacaaaaaac   1740
aaaaggctac gttcgagggt ggatgcacta gtgaaaacag tggaactggg ccgtcggtac   1800
ttcccaaact gctcgcaggt gctcgacaaa ttcttggaag atggcctgcc tgatggcctt   1860
gatgcattcc agcagcaaag cggcacccct gatgagcaac aggtgaagaa gatgcgcttc   1920
tgcgaggtga aggaggacgt gcgcaaagca tacagcaaag acacggccga taacagcatg   1980
ttttcagccc tgtcgtcaaa ctcctcatcc tcggcgatga agtgaaggta ctgtaacagg   2040
ctgttttctg gagatgtcag gactaaagag ggatcgctgg tcatgcgcat gtatagtgct   2100
caccatcgtg taaaactgaa tatgaacatg aaagaaggcc ccaaaatagt agaagatgat   2160
atatactttg ctggacttgg agtttgttgg agaaggctgt gccatcccat tccagattcc   2220
caatatcaat tttcccatgc tggttgtgaa gacagagccg cggatcatcc agctccgacg   2280
ctatgcatgc gtgcagcctg ctgtatttgt ttcgcatagc tgcaatactt atatgtttaa   2340
taatagtact agggagtagt aggttattga ggctgtagcg gaagttggaa cctaccttaa   2400
tgtaagtgaa agggggcccg                                                2420
```

<210> SEQ ID NO 8
<211> LENGTH: 2120
<212> TYPE: DNA
<213> ORGANISM: Triticum aestivum -continued

<400> SEQUENCE: 8

```
gggtttccgt gccgacgcgg atctgtgtgg tgccaaacaa agcctgcccg aattgcgcag      60
ttcggccggg agcgaccaaa aggcagcctc cccctttgc cttcacacat ggtggtccgg      120
ctctagggcc ctttcgcctc gtgcttggcg gcggtgatgg agccgtcgtc gtccatcacg     180
ttcgcctcct cgtcgtccta cctgtccaac ggctctagcc cctgctccgg cgctctggca     240
ccgctgcccg cggcggacgg gtggggcggg ggcggtggag ggggaggggg agggagcagc     300
agcagcgtcg aggccgtgag cttgaatcgc ctcagcagca acctcgagcg cctcctcctc     360
gattctgaac tcgactgcag cgacgctgac gtcgacgtcg cggacggcgg tccgcccatc     420
cccgtccacc gttgcatcct cgccgtgcgc agctccttct tccacgacct cttccgcgcc     480
cgcgggagcc gcagtgatgg ggccgtcact gcctctgcct ccgccaccgg aggcggagcg     540
ggaggggatg tgaacgggag gccgcagtac aagatggagg acctcgtccc aggtggccgt     600
gtgggccgcg aggccttcct agcgttcatg gggtacctct acacgggcag gctccggccg     660
gcgccgctgg acgtggtgtc atgtgctgat cttgtgtgcc cgcacgactc gtgcccgccg     720
gctatcaggt tcgccgtcga gctcatgtac gcggcttgga ccttcaggat ccccgagctc     780
atgtcgctgt tccagcgacg gcttatgaac tttgttgaca agactctggc ggaagacgtc     840
ctacctattt tgcaagttgc tttccactcg gagcttactc aagtgcgtga aaaatgtgtt     900
caaaggattg caagatcgga tcttgatatt atgtctttgg ataaggaact ccctccagaa     960
attgctgacg agataaaaaa gatccgtcag aaatctccgc caattgatgg tgacaccatc    1020
atttcggacc ctgtacacga gaaaagagta agaagaatcc acagggcact ggattctgat    1080
gatgttgaac ttgtcaagtt gcttcttaat gagtctgaaa tcacccttga cgacgcaaac    1140
gcattgcatt atgctgcagc ttactgcgat tccaaagttc ttacagagtt gttaggcctg    1200
gaacttgcca acttgaattt gaagaacagt cgtgggtaca cagcactcca cctagctgct    1260
atgaggagag aaccagctat tattatgtgt ctcttaagca aaggagcagt ggcgtcgcaa    1320
ttgacagatg acggccgcct tgcaagtaat atttgtcgaa ggttaacaag actaaaagat    1380
tacaatgcga agatggagca gggccaagag tcaaataaag ataggatgtg cattgacatc    1440
ctagagaggg agatgatgag gaatcctatg acagcggaag attctgtcac ctcaccttta    1500
ttggctgatg atcttcacat gaaactaagc tacctggaaa acagagtcgc gttcgcaaga    1560
ctgttcttcc ctgctgaagc caaggttgcc atgcaaattg cacaagcaga cgtcacacca    1620
gaagttggtg gtttttctgc agcaagtact tctggtaaac tgagggaagt cgatctgaat    1680
gagacgccag taacaaaaaa caaaaggctg cgttcaaggg tggatgcact agcgaaaaca    1740
gtggaactgg gccgtcggta cttcccaaac tgctcgcagg tgctcgacaa attcttggaa    1800
gatggcctgc ctgatggcct tgatgcgttc cagcagcaaa gcggcacccc tgatgagcaa    1860
caggtgaaga agatgcgctt ctgcgaggtg aaggaggacg tgcgcaaagc atacagcaaa    1920
gacacggccg ataacagcat gttttcggcc ctgtcgtcaa actcctcgtc ctcggcgatg    1980
aagtgaaggt actgtaacag gctgttttct cgagatgtca gggctaaaga gggatcgctg    2040
gtcatgcgca tgtatagtgc ccaccatcgt gtaaaaccga atatgaacat gaaaggaggc    2100
cccaaaatag tagaagaccg                                                2120
```

<210> SEQ ID NO 9
<211> LENGTH: 706
<212> TYPE: DNA
<213> ORGANISM: Triticum aestivum -continued

<400> SEQUENCE: 9

```
tcacagggcg ttggactggg atgatgttga acttgtgaag ttgcttctta atgagtctga     60
aatcacccta gacgacgcca acgcattgca ttatgctgca gcttactgcg attccaaagt    120
tcttaccgag ttgttaggcc tggaacttgc caacttgaat ttgaagaaca gtcgtgggta    180
cacagcactc cacctagctg ctatgaggag agaaccagct attattatgt gtctcttaag    240
caaaggagca gtggcgtcgc aattgacaga tgatggccgc cttgcaagta atatttgtcg    300
aagattaaca agactaaaag attataatgc aaagatggag cagggccaag agtcaaataa    360
agataggatg tgcattgaca tcctagagag ggagatgatg aggaatccta tgacagcgga    420
agattcagtc acctcacctt tattggctga tgatcttcac atgaaactaa gctacctgga    480
aaatagagtc gcgtttgcaa gattattctt ccctgctgaa gcgaaggttg cgatgcaaat    540
tgcgcaagca gacgtcacac cagaagttgg tgtttttct gcagcaagta cttctggtaa     600
actgagggaa gtcgatctga atgagacgcc agtaacaaaa aacaaaaggc tacgttcgag    660
ggtggatgca ctcgcaaaaa cagtggaact cggccgccgc tacttc                   706
```

<210> SEQ ID NO 10
<211> LENGTH: 607
<212> TYPE: PRT
<213> ORGANISM: Triticum aestivum

<400> SEQUENCE: 10

```
Met Glu Pro Ser Ser Ser Ile Thr Val Ala Ser Ser Ser Ser Tyr Leu
  1               5                  10                  15

Ser Asn Gly Ser Ser Pro Cys Ser Gly Ala Leu Ala Pro Leu Pro Ala
             20                  25                  30

Ala Asp Gly Trp Gly Gly Ala Gly Gly Gly Gly Gly Ser Ser Ser Ser
         35                  40                  45

Val Glu Ala Val Ser Leu Ser Arg Leu Ser Ser Asn Leu Glu Arg Leu
     50                  55                  60

Leu Leu Asp Ser Glu Leu Asp Cys Ser Asp Ala Asp Val Asp Val Ala
 65                  70                  75                  80

Asp Gly Gly Pro Pro Ile Pro Ile His Arg Cys Ile Leu Ala Ala Arg
                 85                  90                  95

Ser Pro Phe Phe His Asp Leu Phe Arg Ala Arg Gly Ser Arg Ser Asp
            100                 105                 110

Gly Ala Val Thr Ala Ser Ala Ser Ala Thr Ser Gly Gly Ala Gly Gly
        115                 120                 125

Asp Val Thr Gly Arg Pro Gln Tyr Lys Met Glu Asp Leu Val Pro Gly
    130                 135                 140

Gly Arg Val Gly Arg Glu Ala Phe Leu Ala Phe Met Gly Tyr Leu Tyr
145                 150                 155                 160

Thr Gly Arg Leu Arg Pro Ala Pro Leu Asp Val Val Ser Cys Ala Asp
                165                 170                 175

Leu Val Cys Pro His Asp Ser Cys Pro Pro Ala Ile Arg Phe Ala Val
            180                 185                 190

Glu Leu Met Tyr Ala Ala Trp Thr Phe Arg Ile Pro Glu Leu Met Ser
        195                 200                 205

Leu Phe Gln Arg Arg Leu Met Asn Phe Val Asp Lys Thr Leu Ala Glu
    210                 215                 220

Asp Val Leu Pro Ile Leu Gln Val Ala Phe His Ser Glu Leu Thr Gln
225                 230                 235                 240
```

-continued

```
Val Arg Glu Lys Cys Val Gln Arg Ile Ala Arg Ser Asp Leu Asp Ile
                245                 250                 255

Met Ser Leu Asp Lys Glu Leu Leu Pro Glu Ile Ala Asp Glu Ile Lys
            260                 265                 270

Arg Ile Arg Gln Lys Ser Pro Pro Ile Asp Gly Asp Thr Ile Ile Ser
        275                 280                 285

Asp Pro Ile His Glu Lys Arg Val Arg Arg Ile His Arg Ala Leu Asp
    290                 295                 300

Ser Asp Asp Val Glu Leu Val Lys Leu Leu Leu Asn Glu Ser Glu Ile
305                 310                 315                 320

Thr Leu Asp Asp Ala Asn Ala Leu His Tyr Ala Ala Ala Tyr Cys Asp
                325                 330                 335

Ser Lys Val Leu Thr Glu Leu Leu Gly Leu Glu Leu Ala Asn Leu Asn
            340                 345                 350

Leu Lys Asn Ser Arg Gly Tyr Thr Ala Leu His Leu Ala Ala Met Arg
        355                 360                 365

Arg Glu Pro Ala Ile Ile Met Cys Leu Leu Ser Lys Gly Ala Val Ala
    370                 375                 380

Ser Gln Leu Thr Asp Asp Gly Arg Leu Ala Ser Asn Ile Cys Arg Arg
385                 390                 395                 400

Leu Thr Arg Leu Lys Asp Tyr Asn Ala Lys Met Glu Gln Gly Gln Glu
                405                 410                 415

Ser Asn Lys Asp Arg Met Cys Ile Asp Ile Leu Glu Arg Glu Met Met
            420                 425                 430

Arg Asn Pro Met Thr Ala Glu Asp Ser Val Thr Ser Pro Leu Leu Ala
        435                 440                 445

Asp Asp Leu His Met Lys Leu Ser Tyr Leu Glu Asn Arg Val Ala Phe
    450                 455                 460

Ala Arg Leu Phe Phe Pro Ala Glu Ala Lys Val Ala Met Gln Ile Ala
465                 470                 475                 480

Gln Ala Asp Ile Thr Pro Glu Val Gly Gly Phe Ser Ala Ala Ser Thr
                485                 490                 495

Ser Gly Lys Leu Arg Glu Val Asp Leu Asn Glu Thr Pro Val Thr Lys
            500                 505                 510

Asn Lys Arg Leu Arg Ser Arg Val Asp Ala Leu Val Lys Thr Val Glu
        515                 520                 525

Leu Gly Arg Arg Tyr Phe Pro Asn Cys Ser Gln Val Leu Asp Lys Phe
    530                 535                 540

Leu Glu Asp Gly Leu Pro Asp Gly Leu Asp Ala Phe Gln Gln Gln Ser
545                 550                 555                 560

Gly Thr Pro Asp Glu Gln Gln Val Lys Lys Met Arg Phe Cys Glu Val
                565                 570                 575

Lys Glu Asp Val Arg Lys Ala Tyr Ser Lys Asp Thr Ala Asp Asn Ser
            580                 585                 590

Met Phe Ser Ala Leu Ser Ser Asn Ser Ser Ser Ser Ala Met Lys
        595                 600                 605
```

<210> SEQ ID NO 11
<211> LENGTH: 609
<212> TYPE: PRT
<213> ORGANISM: Triticum aestivum

<400> SEQUENCE: 11

```
Met Glu Pro Ser Ser Ser Ile Thr Phe Ala Ser Ser Ser Ser Tyr Leu
```

-continued

```
1               5                   10                  15

Ser Asn Gly Ser Ser Pro Cys Ser Gly Ala Leu Ala Pro Leu Pro Ala
            20                  25                  30

Ala Asp Gly Trp Gly Gly Gly Gly Gly Gly Gly Gly Gly Gly Ser Ser
        35                  40                  45

Ser Ser Val Glu Ala Val Ser Leu Asn Arg Leu Ser Ser Asn Leu Glu
    50                  55                  60

Arg Leu Leu Leu Asp Ser Glu Leu Asp Cys Ser Asp Ala Asp Val Asp
65                  70                  75                  80

Val Ala Asp Gly Gly Pro Pro Ile Pro Val His Arg Cys Ile Leu Ala
                85                  90                  95

Val Arg Ser Ser Phe Phe His Asp Leu Phe Arg Ala Arg Gly Ser Arg
            100                 105                 110

Ser Asp Gly Ala Val Thr Ala Ser Ala Ser Ala Thr Gly Gly Gly Ala
        115                 120                 125

Gly Gly Asp Val Asn Gly Arg Pro Gln Tyr Lys Met Glu Asp Leu Val
    130                 135                 140

Pro Gly Gly Arg Val Gly Arg Glu Ala Phe Leu Ala Phe Met Gly Tyr
145                 150                 155                 160

Leu Tyr Thr Gly Arg Leu Arg Pro Ala Pro Leu Asp Val Val Ser Cys
                165                 170                 175

Ala Asp Leu Val Cys Pro His Asp Ser Cys Pro Pro Ala Ile Arg Phe
            180                 185                 190

Ala Val Glu Leu Met Tyr Ala Ala Trp Thr Phe Arg Ile Pro Glu Leu
        195                 200                 205

Met Ser Leu Phe Gln Arg Arg Leu Met Asn Phe Val Asp Lys Thr Leu
    210                 215                 220

Ala Glu Asp Val Leu Pro Ile Leu Gln Val Ala Phe His Ser Glu Leu
225                 230                 235                 240

Thr Gln Val Arg Glu Lys Cys Val Gln Arg Ile Ala Arg Ser Asp Leu
                245                 250                 255

Asp Ile Met Ser Leu Asp Lys Glu Leu Pro Pro Glu Ile Ala Asp Glu
            260                 265                 270

Ile Lys Lys Ile Arg Gln Lys Ser Pro Pro Ile Asp Gly Asp Thr Ile
        275                 280                 285

Ile Ser Asp Pro Val His Glu Lys Arg Val Arg Arg Ile His Arg Ala
    290                 295                 300

Leu Asp Ser Asp Asp Val Glu Leu Val Lys Leu Leu Leu Asn Glu Ser
305                 310                 315                 320

Glu Ile Thr Leu Asp Asp Ala Asn Ala Leu His Tyr Ala Ala Ala Tyr
                325                 330                 335

Cys Asp Ser Lys Val Leu Thr Glu Leu Leu Gly Leu Glu Leu Ala Asn
            340                 345                 350

Leu Asn Leu Lys Asn Ser Arg Gly Tyr Thr Ala Leu His Leu Ala Ala
        355                 360                 365

Met Arg Arg Glu Pro Ala Ile Ile Met Cys Leu Leu Ser Lys Gly Ala
    370                 375                 380

Val Ala Ser Gln Leu Thr Asp Asp Gly Arg Leu Ala Ser Asn Ile Cys
385                 390                 395                 400

Arg Arg Leu Thr Arg Leu Lys Asp Tyr Asn Ala Lys Met Glu Gln Gly
                405                 410                 415

Gln Glu Ser Asn Lys Asp Arg Met Cys Ile Asp Ile Leu Glu Arg Glu
            420                 425                 430
```

-continued

```
Met Met Arg Asn Pro Met Thr Ala Glu Asp Ser Val Thr Ser Pro Leu
        435                 440                 445

Leu Ala Asp Asp Leu His Met Lys Leu Ser Tyr Leu Glu Asn Arg Val
    450                 455                 460

Ala Phe Ala Arg Leu Phe Phe Pro Ala Glu Ala Lys Val Ala Met Gln
465                 470                 475                 480

Ile Ala Gln Ala Asp Val Thr Pro Glu Val Gly Gly Phe Ser Ala Ala
                485                 490                 495

Ser Thr Ser Gly Lys Leu Arg Glu Val Asp Leu Asn Glu Thr Pro Val
            500                 505                 510

Thr Lys Asn Lys Arg Leu Arg Ser Arg Val Asp Ala Leu Ala Lys Thr
        515                 520                 525

Val Glu Leu Gly Arg Arg Tyr Phe Pro Asn Cys Ser Gln Val Leu Asp
    530                 535                 540

Lys Phe Leu Glu Asp Gly Leu Pro Asp Gly Leu Asp Ala Phe Gln Gln
545                 550                 555                 560

Gln Ser Gly Thr Pro Asp Glu Gln Gln Val Lys Lys Met Arg Phe Cys
                565                 570                 575

Glu Val Lys Glu Asp Val Arg Lys Ala Tyr Ser Lys Asp Thr Ala Asp
            580                 585                 590

Asn Ser Met Phe Ser Ala Leu Ser Ser Asn Ser Ser Ser Ser Ala Met
        595                 600                 605

Lys


<210> SEQ ID NO 12
<211> LENGTH: 8
<212> TYPE: PRT
<213> ORGANISM: Arabidopsis thaliana

<400> SEQUENCE: 12

His Arg Ala Leu Asp Trp Asp Asp
  1               5


<210> SEQ ID NO 13
<211> LENGTH: 7
<212> TYPE: PRT
<213> ORGANISM: Arabidopsis thaliana

<400> SEQUENCE: 13

Glu Leu Gly Arg Arg Tyr Phe
  1               5


<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:n=I
<220> FEATURE:
<221> NAME/KEY: primer_bind
<222> LOCATION: (1)..(23)

<400> SEQUENCE: 14

cayarngcny tngaywsnga yga                                            23


<210> SEQ ID NO 15
<211> LENGTH: 21
<212> TYPE: DNA
<213> ORGANISM: Artificial Sequence
<220> FEATURE:
```

-continued

<223> OTHER INFORMATION: Description of Artificial Sequence:n=I
<220> FEATURE:
<221> NAME/KEY: primer_bind
<222> LOCATION: ()..(21)

<400> SEQUENCE: 15
raarwanckn yknccnaryt c 21

<210> SEQ ID NO 16
<211> LENGTH: 1385
<212> TYPE: DNA
<213> ORGANISM: Zea mays

<400> SEQUENCE: 16
gaattcccgg gtcgacccac gcgtccgccc acgcgtccgc aaaggattgc tagatcagat 60
ctcgacgata tatctttgga taaggagctc cctccagaag cagttgatga gataaaaaat 120
ttgcgcaaga attcacaaac tgctgatggt gatacgttca tttcggaccc tgtgcatgag 180
aaaagagtca gaagaatcca cagggcactt gactctgatg atgttgagct tgtgaagttg 240
cttcttaatg agtccgacat cacattagat gatgccaacg cattacacta tgctgcttct 300
tactgtgatc ctaaagttgt ctcagagctg ttagatttgg caatggctaa cttaaatttg 360
aagaattccc gtgggtacac agcactccac ttggctgcta tgaggagaga accagctata 420
atcatgtgtc tccttaacaa aggggcaaat gtgtcacaac tgacagctga tggcaggagc 480
gcaattggta tttgtcggag gttaacaaga gcaaaagact acaatacaaa gatggagcag 540
ggtcaagaat caaataaaga taggctgtgt atagatattc tagagaggga gatgatgcgg 600
aatcctatgg cggtggaaga tgccgtcacc tcgcctttgt tggcagatga tcttcacatg 660
aagcttctct acctggaaaa cagagttgca tttgctagat tgttctttcc tgctgaagcc 720
aaggtcgcca tgcaaatcgc acaagcagac accacgaagg aattcggcgg tatagttgca 780
gttgcagcaa gcacttctgg taaactgagg gaggtggacc ttaatgagac gccagtgaca 840
caaaacaaaa ggctccgttc aagggtagat gcactgatga aaacagtgga gctgggccgt 900
cggtacttcc cgaactgctc gcaggtgctg gacaagttcc tggaggacga tctgccggaa 960
ggtctggacc agttctacct ccagaggggc acagccgatg agcagaaggt gaagaggatg 1020
cgcttctgcg agctgaaaga ggacgtgctg aaggcgttta gcaaggacaa ggcggagggc 1080
agcgtgttct cgggcctgtc ctcgtcgtcg tcgtgctcgc cgccccagaa gtatgcccag 1140
aggtgatcaa ggcaccagtt tttgccgtat agtttgttat catggtcttc gagacttgga 1200
cccggacagc atatagggac atgtacacct gtgtatgtat agtgcttaca attggcgtaa 1260
gtagaactat atgtatggaa cataaggaaa catggcagga acaccgtgca aaaagatgaa 1320
aagatggccg aagtgctcta tgcgagtgcc cacctgaaaa aaaaaaaaaa aaaaagggcg 1380
gccgc 1385

<210> SEQ ID NO 17
<211> LENGTH: 381
<212> TYPE: PRT
<213> ORGANISM: Zea mays

<400> SEQUENCE: 17

Glu Phe Pro Gly Arg Pro Thr Arg Pro Pro Thr Arg Pro Gln Arg Ile
1 5 10 15

Ala Arg Ser Asp Leu Asp Asp Ile Ser Leu Asp Lys Glu Leu Pro Pro
20 25 30

-continued

```
Glu Ala Val Asp Glu Ile Lys Asn Leu Arg Lys Asn Ser Gln Thr Ala
        35                  40                  45

Asp Gly Asp Thr Phe Ile Ser Asp Pro Val His Glu Lys Arg Val Arg
    50                  55                  60

Arg Ile His Arg Ala Leu Asp Ser Asp Asp Val Glu Leu Val Lys Leu
65                  70                  75                  80

Leu Leu Asn Glu Ser Asp Ile Thr Leu Asp Asp Ala Asn Ala Leu His
                85                  90                  95

Tyr Ala Ala Ser Tyr Cys Asp Pro Lys Val Val Ser Glu Leu Leu Asp
            100                 105                 110

Leu Ala Met Ala Asn Leu Asn Leu Lys Asn Ser Arg Gly Tyr Thr Ala
        115                 120                 125

Leu His Leu Ala Ala Met Arg Arg Glu Pro Ala Ile Ile Met Cys Leu
    130                 135                 140

Leu Asn Lys Gly Ala Asn Val Ser Gln Leu Thr Ala Asp Gly Arg Ser
145                 150                 155                 160

Ala Ile Gly Ile Cys Arg Arg Leu Thr Arg Ala Lys Asp Tyr Asn Thr
                165                 170                 175

Lys Met Glu Gln Gly Gln Glu Ser Asn Lys Asp Arg Leu Cys Ile Asp
            180                 185                 190

Ile Leu Glu Arg Glu Met Met Arg Asn Pro Met Ala Val Glu Asp Ala
        195                 200                 205

Val Thr Ser Pro Leu Leu Ala Asp Asp Leu His Met Lys Leu Leu Tyr
    210                 215                 220

Leu Glu Asn Arg Val Ala Phe Ala Arg Leu Phe Phe Pro Ala Glu Ala
225                 230                 235                 240

Lys Val Ala Met Gln Ile Ala Gln Ala Asp Thr Thr Lys Glu Phe Gly
                245                 250                 255

Gly Ile Val Ala Val Ala Ala Ser Thr Ser Gly Lys Leu Arg Glu Val
            260                 265                 270

Asp Leu Asn Glu Thr Pro Val Thr Gln Asn Lys Arg Leu Arg Ser Arg
        275                 280                 285

Val Asp Ala Leu Met Lys Thr Val Glu Leu Gly Arg Arg Tyr Phe Pro
    290                 295                 300

Asn Cys Ser Gln Val Leu Asp Lys Phe Leu Glu Asp Asp Leu Pro Glu
305                 310                 315                 320

Gly Leu Asp Gln Phe Tyr Leu Gln Arg Gly Thr Ala Asp Glu Gln Lys
                325                 330                 335

Val Lys Arg Met Arg Phe Cys Glu Leu Lys Glu Asp Val Leu Lys Ala
            340                 345                 350

Phe Ser Lys Asp Lys Ala Glu Gly Ser Val Phe Ser Gly Leu Ser Ser
        355                 360                 365

Ser Ser Ser Cys Ser Pro Pro Gln Lys Tyr Ala Gln Arg
    370                 375                 380


<210> SEQ ID NO 18
<211> LENGTH: 640
<212> TYPE: DNA
<213> ORGANISM: Zea mays

<400> SEQUENCE: 18

gaattcccgg gtcgacccac gcgtccgccc acgcgtccgc tgagggaggt ggaccttaat      60

gagacgccag tgacacaaaa caaaaggctc cgttcaaggg tagatgcact gatgaaaaca     120

gtggagctgg gccgtcggta cttcccgaac tgctcgcagg tgctggacaa gttcctggag     180
```

-continued

```
gacgatctgc cggaaggtct ggaccagttc tacctccaga ggggcacagc cgatgagcag    240

aaggtgaaga ggatgcgctt ctgcgagctg aaagaggacg tgctgaaggc gtttagcaag    300

gacaaggcgg agggcagcgt gttctcgggc ctgtcctcgt cgtcgtcgtg ctcgccgccc    360

cagaagtatg cccagaggtg atcaaggcac cagtttttgc cgtatagttt gttatcatgg    420

tcttcgagac ttggacccgg acagcatata gggacatgta cacctgtgta tgtatagtgc    480

ttacaattgg cgtaagtaga actatatgta tggaacataa ggaaacatgg caggaacacc    540

gtgcaaaaag atgaaaagat ggccgaagtg ctctatgcga gtgcccacct gattcgatgg    600

ccctattcaa aaaaaaaaaa aaaaaaaaaa aaaaaaaaaa                          640
```

<210> SEQ ID NO 19
<211> LENGTH: 126
<212> TYPE: PRT
<213> ORGANISM: Zea mays

<400> SEQUENCE: 19

```
Glu Phe Pro Gly Arg Pro Thr Arg Pro Pro Thr Arg Pro Leu Arg Glu
  1               5                  10                  15

Val Asp Leu Asn Glu Thr Pro Val Thr Gln Asn Lys Arg Leu Arg Ser
             20                  25                  30

Arg Val Asp Ala Leu Met Lys Thr Val Glu Leu Gly Arg Arg Tyr Phe
         35                  40                  45

Pro Asn Cys Ser Gln Val Leu Asp Lys Phe Leu Glu Asp Asp Leu Pro
     50                  55                  60

Glu Gly Leu Asp Gln Phe Tyr Leu Gln Arg Gly Thr Ala Asp Glu Gln
 65                  70                  75                  80

Lys Val Lys Arg Met Arg Phe Cys Glu Leu Lys Glu Asp Val Leu Lys
                 85                  90                  95

Ala Phe Ser Lys Asp Lys Ala Glu Gly Ser Val Phe Ser Gly Leu Ser
            100                 105                 110

Ser Ser Ser Ser Cys Ser Pro Pro Gln Lys Tyr Ala Gln Arg
        115                 120                 125
```

<210> SEQ ID NO 20
<211> LENGTH: 2235
<212> TYPE: DNA
<213> ORGANISM: Zea mays

<400> SEQUENCE: 20

```
gaattcggct cgagcacgat tcgtgcccgc cggccatcag gtccgcggtc gagctcatgt     60

acgcggcgtg taccttcaag atccccgagc tcacctcgct cttccaggcg aacctggtgg    120

cttgaagtct atgaattgaa atggaatcat tattcattag gctgctcaac atttgaatat    180

tacatttatg gctgtatagt ttatcaatca gtttaacatc aattgagctt tgctttgtct    240

ttacggaagg caaatggtta acatggtctt cttctacagc ggcggcttct taattttgta    300

gacaagactc tagtggagga tgtcattcct attctggaag ttgcttccca ctcagggctg    360

actcaagtga tcgacaaatg tattcaaagg attgctagat cagatcttga tgatatatct    420

ttggataagg agctccctcc agaagcagtt gatgagataa aaaatttgcg caagaagtca    480

caaactgctg atggtgatac gttcatttcg gaccctgtgc atgagaaaag agtcagaaga    540

atccacaggg cacttgactc tgatgatgtt gagcttgtga agttgcttct taatgagtcc    600

gacatcacat tagatgatgc caacgcatta cactatgctg cttcttactg tgatcctaaa    660
```

-continued

```
gttgtctcag agctgttaga tttggcaatg gctaacttaa atttgaagaa tagccgtggg    720
tacacagcac tccacttggc tgctatgagg agagaaccag ctataatcat gtgtctcctt    780
aacaaagggg caaatgtgtc acaactgaca gctgatggca ggagcgcaat tggtatttgt    840
cggaggttaa caagagcaaa agactacaat acaaagatgg agcagggtca agaatcaaat    900
aaagataggc tgtgtataga tattctagag agggagatga tgcggaatcc tatggcggtg    960
gaagatgccg tcacctcgcc tttgttggca gatgatcttc acatgaagct tctctacctg   1020
gaaaacagag ttgcatttgc tagattgttc tttcctgctg aagccaaggt cgccatgcaa   1080
atcgcacaag cagacaccac agaagaattc ggcggtatag ttgcagttgc agcaagcact   1140
tccggtaaac tgagggaggt ggaccttaat gagacgccag tgacacaaaa caaaaggctc   1200
cgttcaaggg tagatgcact gatgaaaaca gtggagctgg gccgtcggta cttcccgaac   1260
tgctcgcagg tgctggacaa gttcctggag gacgatctgc cggaagtctg gaccagttct   1320
tacctccaga ggggcacagc cgatgagcag aagttgaaga ggatgcgctt ctgcgagctg   1380
aaagaggacg tgctgaaggc gtttagcaag gacaaggcgg agggcagcgt gttctcgggc   1440
ctgtcctcgt cgtcgtcgtg ctcgccgccc cagaagtatg cccagaggtg atcaaggcac   1500
cagtttttgc cgtatagttt gttatcatgg tcttcgagac ttggacccgg acagcatata   1560
gggacatgta cacctgtgta tgtatagtgc ttacaattgg cgtaagtaga actatatata   1620
tggaacataa ggaaacatgg caggaacacc gcgcaaaaag atgaaaagat ggccgaagtg   1680
ctctatgcga gtgcgcacct gattcgatgg ccctattcaa cggcgccctg tcagcatgct   1740
gcatgcccac tgagaccttc ggttgcatag ggataggagg agatttctgt tcaattttgg   1800
ctagcaagtg atatagggt gtttaggact gtttcacttt atgaaaatca acttagctca   1860
taaacacttt taacttcaat aacttaggtc ctgtttggag tggctgtatt tttctagtcc   1920
caagaaaata atgtggtatc tgagaatacc atggtctaga aaccaaaatg tgtttggcag   1980
actcttttaa accatggtat ttaaaatctt ggttttgaca agaccacatt atttctgggt   2040
atagaatact gtcagccgag ttcggctcgg ctcggtgcgg ctcgttgact gaacgagctc   2100
gactcggctc gtccattcca cgagctggtg aaagaggctc ggctcggctc gaccttagct   2160
cgcgagccat attcttgtaa aaaaaaaaaa aaaaaaaaaa aaaaaaaaaa aaaaaaaaaa   2220
aaaaagggcg gccgc                                                    2235
```

<210> SEQ ID NO 21
<211> LENGTH: 409
<212> TYPE: PRT
<213> ORGANISM: Zea mays

<400> SEQUENCE: 21

```
His Gly Leu Leu Leu Gln Arg Arg Leu Leu Asn Phe Val Asp Lys Thr
  1               5                  10                  15

Leu Val Glu Asp Val Ile Pro Ile Leu Glu Val Ala Ser His Ser Gly
             20                  25                  30

Leu Thr Gln Val Ile Asp Lys Cys Ile Gln Arg Ile Ala Arg Ser Asp
         35                  40                  45

Leu Asp Asp Ile Ser Leu Asp Lys Glu Leu Pro Pro Glu Ala Val Asp
     50                  55                  60

Glu Ile Lys Asn Leu Arg Lys Lys Ser Gln Thr Ala Asp Gly Asp Thr
 65                  70                  75                  80

Phe Ile Ser Asp Pro Val His Glu Lys Arg Val Arg Arg Ile His Arg
                 85                  90                  95
```

-continued

```
Ala Leu Asp Ser Asp Asp Val Glu Leu Val Lys Leu Leu Leu Asn Glu
            100                 105                 110

Ser Asp Ile Thr Leu Asp Asp Ala Asn Ala Leu His Tyr Ala Ala Ser
        115                 120                 125

Tyr Cys Asp Pro Lys Val Val Ser Glu Leu Leu Asp Leu Ala Met Ala
    130                 135                 140

Asn Leu Asn Leu Lys Asn Ser Arg Gly Tyr Thr Ala Leu His Leu Ala
145                 150                 155                 160

Ala Met Arg Arg Glu Pro Ala Ile Ile Met Cys Leu Leu Asn Lys Gly
                165                 170                 175

Ala Asn Val Ser Gln Leu Thr Ala Asp Gly Arg Ser Ala Ile Gly Ile
            180                 185                 190

Cys Arg Arg Leu Thr Arg Ala Lys Asp Tyr Asn Thr Lys Met Glu Gln
        195                 200                 205

Gly Gln Glu Ser Asn Lys Asp Arg Leu Cys Ile Asp Ile Leu Glu Arg
    210                 215                 220

Glu Met Met Arg Asn Pro Met Ala Val Glu Asp Ala Val Thr Ser Pro
225                 230                 235                 240

Leu Leu Ala Asp Asp Leu His Met Lys Leu Leu Tyr Leu Glu Asn Arg
                245                 250                 255

Val Ala Phe Ala Arg Leu Phe Phe Pro Ala Glu Ala Lys Val Ala Met
            260                 265                 270

Gln Ile Ala Gln Ala Asp Thr Thr Glu Glu Phe Gly Gly Ile Val Ala
        275                 280                 285

Val Ala Ala Ser Thr Ser Gly Lys Leu Arg Glu Val Asp Leu Asn Glu
    290                 295                 300

Thr Pro Val Thr Gln Asn Lys Arg Leu Arg Ser Arg Val Asp Ala Leu
305                 310                 315                 320

Met Lys Thr Val Glu Leu Gly Arg Arg Tyr Phe Pro Asn Cys Ser Gln
                325                 330                 335

Val Leu Asp Lys Phe Leu Glu Asp Asp Leu Pro Glu Val Trp Thr Ser
            340                 345                 350

Ser Tyr Leu Gln Arg Gly Thr Ala Asp Glu Gln Lys Leu Lys Arg Met
        355                 360                 365

Arg Phe Cys Glu Leu Lys Glu Asp Val Leu Lys Ala Phe Ser Lys Asp
    370                 375                 380

Lys Ala Glu Gly Ser Val Phe Ser Gly Leu Ser Ser Ser Ser Ser Cys
385                 390                 395                 400

Ser Pro Pro Gln Lys Tyr Ala Gln Arg
                405
```

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:thermal amplification primer

<400> SEQUENCE: 22
ggattgctag atcagatctc g 21

<210> SEQ ID NO 23
<211> LENGTH: 21
<212> TYPE: DNA
<213> ORGANISM: Artificial Sequence -continued

```
<220> FEATURE:
<223> OTHER INFORMATION: Description of Artificial Sequence:thermal
      amplification primer

<400> SEQUENCE: 23

cggtgttcct gccatgtttc c                                                 21


<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 24

acagggcgtt ggactgggat g                                                 21


<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 25

agtgcatcca ccctcgaacg ta                                                22


<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 26

agctcgcgtg gcgaacggac                                                   20


<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 27

gatggtcatg gtgtccggta g                                                 21


<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 28

gacaagaagt tccagaacgt gtccaagg                                          28


<210> SEQ ID NO 29
<211> LENGTH: 26
<212> TYPE: DNA
<213> ORGANISM: Artificial Sequence
<220> FEATURE:
```

-continued

```
<223> OTHER INFORMATION: Description of Artificial Sequence:thermal
      amplification primer

<400> SEQUENCE: 29

gaccggtaga tgctcgacgc aaagtc                                          26


<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 30

ggatgcacta gtgaaaacag tgg                                             23


<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 31

gctctagagg aattctcact tcatcgccga ggatgagg                             38


<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 32

ccatcgatcc atggagccgt cgtcgtccat cac                                  33


<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 33

gactcagact cacagcctcg acg                                             23


<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 34

ttatctgaac agcaacttct                                                 20


<210> SEQ ID NO 35
<211> LENGTH: 180
<212> TYPE: PRT
<213> ORGANISM: Lycopersicon esculentum

<400> SEQUENCE: 35
```

-continued

```
Glu Ala Ser Leu Ser Leu Ala Met Ala Gly Asp Asp Leu Arg Met Lys
  1               5                  10                  15

Leu Leu Tyr Leu Glu Asn Arg Val Gly Leu Ala Lys Leu Leu Phe Pro
            20                  25                  30

Met Glu Ala Lys Val Ala Met Asp Ile Ala Gln Val Asp Gly Thr Ser
        35                  40                  45

Glu Leu Pro Leu Ala Ser Met Arg Lys Lys Ile Ala Asp Ala Gln Arg
     50                  55                  60

Thr Thr Val Asp Leu Asn Glu Ala Pro Phe Lys Met Lys Glu Glu His
 65                  70                  75                  80

Leu Asn Arg Leu Arg Ala Leu Ser Arg Thr Val Glu Leu Gly Lys Arg
                85                  90                  95

Phe Phe Pro Arg Cys Ser Glu Val Leu Asn Lys Ile Met Asp Ala Asp
            100                 105                 110

Asp Leu Ser Glu Ile Ala Tyr Met Gly Asn Asp Thr Val Glu Glu Arg
        115                 120                 125

Gln Leu Lys Lys Gln Arg Tyr Met Glu Leu Gln Glu Ile Leu Ser Lys
    130                 135                 140

Ala Phe Thr Glu Asp Lys Glu Glu Phe Ala Lys Thr Asn Met Ser Ser
145                 150                 155                 160

Ser Cys Ser Ser Thr Ser Lys Gly Val Asp Lys Pro Asn Asn Leu Pro
                165                 170                 175

Phe Arg Lys Glx
            180


<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:thermal
      amplification primer

<400> SEQUENCE: 36

catgccatgg aggagctcgt gccggga                                        27
```

ACQUIRED RESISTANCE GENES IN PLANTS

CROSS REFERENCE TO RELATED APPLICATIONS

This application is a continuation of U.S. patent application Ser. No. 10/318,780, filed Dec. 13, 2002, now U.S. Pat. No. 7,030,293 which is a divisional of U.S. patent application Ser. No. 09/569,804 filed May 12, 2000, now U.S. Pat. No. 6,506,962 issued Jan. 14, 2003, which claims the benefit of priority to U.S. Provisional Application Ser. No. 60/133, 965 filed May 13, 1999.

FIELD OF THE INVENTION

The invention relates to acquired resistance genes in plants and methods for their use. Specifically, the invention discloses novel nucleic acid sequences encoding for acquired resistance genes, transformed host cells and transgenic plants containing acquired resistance genes, and methods of use for conferring resistance to pathogens in plants. Methods are also disclosed for preparing the transformed host cells and transgenic plants.

BACKGROUND OF THE INVENTION

Plants are exposed to numerous denizens of their environment, including bacteria, viruses, fungi, and nematodes. Although many of the interactions between these organisms and plants, particularly via the roots of the plants, are beneficial, many of the interactions are harmful to the plants. The decimation of agricultural crops, ornamental plants, and other plants by diseases caused by plant pathogens, particularly fungal pathogens, is a worldwide problem that has enormous economic impact.

Damage to plants is caused by pathogens of multiple genera. These genera include *Alternaria, Ascochyta, Aspergillus, Botrytis, Cercospora, Colletotrichum, Diplodia, Erwinia, Erysiphe, Fusarium, Gaeumanomyces, Helminthosporium, Macrophomina, Magnaporthe, Mycosphaerella, Nectria, Peronospora, Phoma, Phym atotrichum, Phytophthora, Plasmopara, Podosphaera, Pseudomonas, Puccinia, Puthium, Pyrenophora, Pyricularia, Pythium, Rhizoctonia, Scerotium, Sclerotinia, Septoria, Thielaviopsis, Uncinula, Venturia, Verticillium*, and *Xanthomonas.*

Many chemical compounds have been developed to combat these various pathogens. Examples of chemical antifungal agents include polyoxines, nikkomycines, carboxyamides, aromatic carbohydrates, carboxines, morpholines, inhibitors of sterol biosynthesis, and organophosphorus compounds (Worthington and Walker, 1983; U.S. Pat. No. 5,421,839). The activity of these compounds is typically limited to several species. As a consequence of the large number and diversity of pathogenic fungi, these compounds have not provided an effective solution to limiting infections in plants.

An alternative approach to controlling pathogenic infections in plants involves exploiting the natural defense mechanisms of plants to confer resistance. Many plants have developed natural resistance to some pathogens. However, resistance may be limited to certain genera of pathogens, or crops of agronomic interest may not exhibit sufficient resistance. Thus, natural plant defenses often do not provide sufficient protection against pathogens. By broadening the spectrum of pathogen defense or strengthening the defense response, it may be possible to enhance existing resistance mechanisms and promote pathogen defense in otherwise susceptible plants.

When present and active, the natural defense mechanisms of plants are highly effective in preventing pathogen colonization and disease. Resistance is multi-tiered, with passive and active, constitutive and inducible elements (Baker et al., 1997; Keen, 1990; Ryals et al., 1996). Inducible defense can be activated through the action of plant recognition of a pathogen determinant, or elicitor, to trigger a localized cell death or hypersensitive response (HR) at the site of pathogen attack (Dixon et al., 1994). This localized apoptotic cell death is often mediated by resistance genes (R-genes) that recognize a specific, cognate "avirulence" product in the pathogen (Greenberg, 1997). The local perception of pathogen attack is conveyed to distant tissues via a transmissible signal that involves salicylic acid (SA), further activating gene expression and conditioning a state known as systemic acquired resistance (SAR; Ryals et al., 1996; Sticher et al., 1997). It has subsequently been found that resistance can be expressed near the region of pathogen attack, as local acquired resistance, or can be induced systemically, depending on triggering signal and plant species. Thus the systemic and local responses collectively are referred to as acquired resistance (AR). Establishment of AR is a powerful line of plant defense because it can provide broad-spectrum resistance against viral, bacterial, and fungal challenges that would otherwise cause disease (Cameron et al., 1994; Gorlach et al., 1996; Ryals et al., 1996). The AR response triggers the transcriptional activation of a suite of genes encoding pathogenesis-related (PR) proteins. Included among these are hydrolases, cell-wall strengthening proteins, proteins involved in oxidative burst, the combination of which are believed to promote heightened resistance (Sticher et al., 1997). Biochemical and genetic analyses have identified genes and molecular signals associated with acquired resistance. The Npr1/Nim1 gene plays a key regulatory role in the AR defense in Arabidopsis against a broad spectrum of fungal and bacterial pathogens (Cao et al., 1994; Cao et al., 1997; Delaney et al., 1995; Ryals et al., 1997; WO 98/06748; WO 94/16077; WO 98/26082). Mutant npr1 plants induce normal HR and accumulate SA after avirulent pathogen challenge, but they fail to accumulate PR proteins or activate the AR response, suggesting that this protein functions in the pathway downstream from salicylic acid (Cao et al., 1994; Cao et al., 1997; Delaney et al., 1995). Features of the Npr1 protein suggest a role as a transcriptional regulator and include motifs such as ankyrin repeats, implied in protein-protein interactions; nuclear localization signals; putative phosphorylation sites; and homology with IFKB, a transcriptional regulator in mammalian systems (Cao et al., 1997; Ryals et al., 1997). Nuclear translocation of activated Npr1 has been demonstrated, strengthening its likely role in transcriptional regulation (WO 98/06748). The central importance of Npr1 in dicots was further substantiated by transgenic overexpression of the cloned gene, which led to heightened disease resistance in *Arabidopsis* against both fungal and bacterial pathogens (Cao et al., 1998; WO 98/06748).

Although the bulk of AR research has defined the pathway in dicotyledonous plants, monocotyledonous plants, such as wheat, rice, and barley, have an inducible pathway that protects against pathogen attack (Hwang and Heitefuss, 1982;.Kmecl et al., 1995; Schweizer et al., 1989; Smith and Metraux, 1991). Acquired resistance can be conditioned by different external stimuli, including avirulent pathogen challenge (Manandhar et al., 1998; Schaffrath et al., 1997), pathogen elicitor exposure (Jin et al., 1997; Schaffrath et al., 1995; Waspi et al., 1998), and chemical treatments, including application of SA or SA analogs, such as 2,6-dichloroisonicotinic acid (INA) or benzo(1,2,3) thiodiazole-7-carbothioic acid S-methyl ester (BTH) (Gorlach et al., 1996; Kessman et al., 1994; Kogel et al., 1994; Manandhar et al., 1998; Schaffrath et al., 1997; Watanabe et al., 1979;). Given the inducibility of the AR pathway by the same classes of activating compounds in monocot and dicot plants, there is likely to be partial conservation of signaling pathways, as subsets of PR genes appear to be induced in both groups (Morris et al., 1998). However, studies also point to marked differences in monocots, with inducers of AR revealing new pathways that are tied to new classes of PR genes (Gorlach et al., 1996; Schaffrath et al., 1997). In monocots, induced acquired resistance is broad-spectrum, extending to fungal and bacterial pests, irrespective of pathogen race, with activated resistance persisting for weeks to months. Thus, manipulation of the AR pathway in monocot plants may promote resistance to pathogens for which there exists no genetic source of resistance.

Thus, there is a need to identify genes from monocotylendonous crops, such as wheat and rice, that may play key roles in disease defense. Overexpression of these genes in transgenic plants is expected to enhance the level of disease resistance against certain microbial pathogens. It has; therefore, been discovered that a gene isolated from rice, designated Nph1, and a gene isolated from wheat, designated Nph2, are induced by chemical elicitors known to stimulate AR. Activation of AR and induced expression of Nph1 and Nph2 therefore is expected to protect wheat and rice against biotrophic pathogens. Transgenic overexpression of Nph1 and Nph2 should condition a stronger AR upon pathogen challenge, thus promoting more effective disease protection.

SUMMARY OF THE INVENTION

The present invention relates to the discovery and use of key regulatory genes in the acquired resistance (AR) pathway of plants. Genes have been isolated and characterized from rice and wheat, designated Nph1 and Nph2, respectively. In a particular embodiment of the invention, genes sharing identity with Nph1 and Nph2 are key regulators of the acquired resistance pathway of plants. Overexpression yields transgenic plants with enhanced disease resistance to a broad diversity of pathogens, including, but not limited to, fungal, bacterial, and viral pathogens.

In one aspect, the present invention provides novel nucleic acid sequences that can promote acquired resistance in rice (SEQ ID NO:1) and in wheat (SEQ ID NOS:5 and 6).

In another aspect, the present invention provides an isolated DNA molecule which is or is complementary to a nucleotide sequence selected from the group consisting of a) the nucleotide sequence of SEQ ID NO:1, 5 or 6 which encodes a protein sequence of SEQ ID NO:4, 10 or 11, respectively; b) nucleotide sequences which through degeneracy of the genetic code encode the protein sequence of SEQ ID NO:4, 10 or 11 encoded by the nucleotide sequence of SEQ ID NO:1, 5 or 6, respectively; and nucleotide sequences that hybridize to any nucleotide sequences mentioned in a) and b).

In still another aspect, the present invention provides a DNA sequence that encodes an acquired resistance gene polypeptide that includes a contiguous amino acid sequence of at least 15 amino acids of SEQ ID NO:4, 10, or 11.

In still another aspect, the present invention provides novel protein sequences that can promote acquired resistance in rice (SEQ ID NO:4) and in wheat (SEQ ID NOS:10 and 11).

In still another aspect, the present invention discloses a method of controlling plant pathogens by providing to a plant the nucleotide sequence of SEQ ID NO:1, 5 or 6 in a sufficient amount to enhance acquired resistance of the plant.

In a further embodiment of the invention, plant cells or transgenic plants comprising a nucleic acid sequence that promotes acquired resistance to a variety of pathogens are provided as well as seed or progeny from such plants also comprising said nucleic acid sequence.

BRIEF DESCRIPTION OF THE DRAWINGS

FIG. 3*a* is a view of an untreated control leaf, while FIG. 3*b* is a view of a leaf treated with 0.5 mM INA. Both leaves were challenged with Magnaporthe grisea 3 days after treatment, and scored (photographed) after 7 days.

BRIEF DESCRIPTION OF THE SEQUENCES IN THE SEQUENCE LISTING

Figure 1:
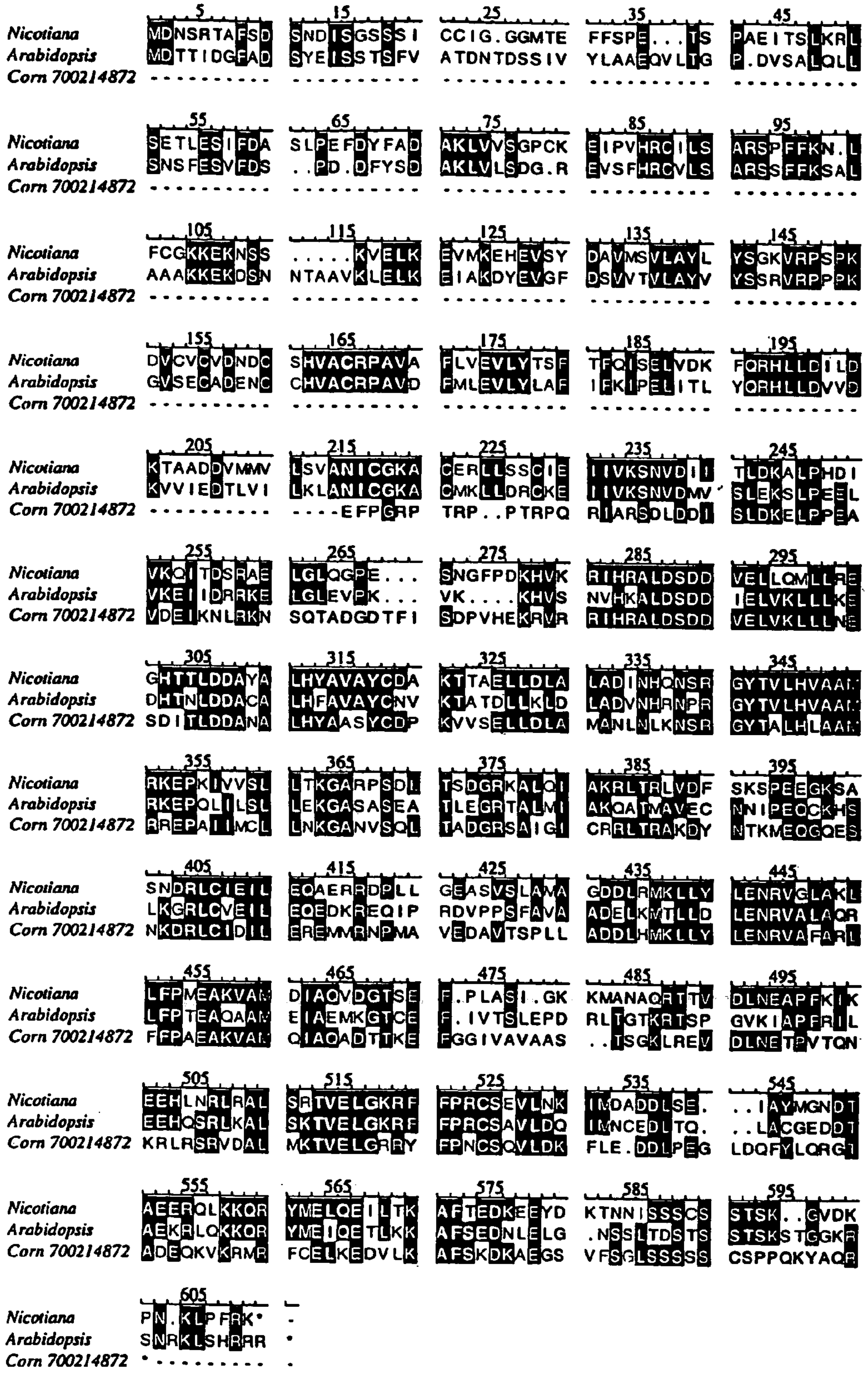
FIG. 1 shows the alignment of the predicted amino acid sequences for Npr1 dicot homologs from *Arabidopsis* (SEQ ID NO; 37) and *Nicotiana glutinosa* (SEQ ID NO; 38) (Ausubel et al., 1998), and corn clone 700214872 sequence (SEQ ID NO:17).

SEQ ID NO:1 Rice Nph1 cDNA sequence for predicted coding region

SEQ ID NO:2 Rice Nph1 cDNA full-length sequence including the 5' and 3' UTRs

SEQ ID NO:3 Rice Nph1 fragment recovered from PCR amplification

SEQ ID NO:4 Rice Nph1 predicted protein sequence

SEQ ID NO:5 Wheat Nph2-1 cDNA sequence for predicted coding region

SEQ ID NO:6 Wheat Nph2-2 cDNA sequence for predicted coding region

SEQ ID NO:7 Wheat Nph2-1 cDNA full-length sequence including the 5' and 3' UTRs

SEQ ID NO:8 Wheat Nph2-2 cDNA full-length sequence including the 5' and 3' UTRs

SEQ ID NO:9 Wheat Nph2 fragment recovered from PCR amplification

SEQ ID NO:10 Wheat Nph2-1 predicted protein sequence

SEQ ID NO:11 Wheat Nph2-2 predicted protein sequence

SEQ ID NO:12 domain 1: corresponding to an Arabidopsis Npr1 protein (aa 270–277)

SEQ ID NO:13 domain 2: corresponding to an Arabidopsis Npr1 protein (aa 501–507)

SEQ ID NO:14 OB09 primer used for monocot thermal amplification

SEQ ID NO:15 OB11 primer used for monocot thermal amplification

SEQ ID NO:16 Corn clone 700214872 nucleotide sequence

SEQ ID NO:17 Corn clone 700214872 predicted amino acid sequence

SEQ ID NO:18 Corn clone 700102819 nucleotide sequence

SEQ ID NO:19 Corn clone 700102819 predicted amino acid sequence

SEQ ID NO:20 Corn contig CPR95 1.FLR nucleotide sequence

SEQ ID NO:21 Corn contig CPR95 1.FLR predicted amino acid sequence

SEQ ID NO:22 OB-01 primer

SEQ ID NO:23 OB-02 primer

SEQ ID NO:24 OB-18 primer

SEQ ID NO:25 OB-19 primer

SEQ ID NO:26 OB-28 primer

SEQ ID NO:27 OB-29 primer

SEQ ID NO:28 OB-38 primer

SEQ ID NO:29 OB-39 primer

SEQ ID NO:30 OB-61 primer

SEQ ID NO:31 OB-62 primer

SEQ ID NO:32 OB-63 primer

SEQ ID NO:33 OB-64 primer

SEQ ID NO:34 Rice NcoI primer

SEQ ID NO:35 NS-10 primer

SEQ ID NO:36 a tomato Npr1 homolog protein sequence used for antibody production

DETAILED DESCRIPTION OF THE INVENTION

Definitions

In order to provide a clear and consistent understanding of the specification and the claims, including the scope given to such terms, the following definitions are provided.

The acquired resistance gene from rice (Npr1 homolog 1) will henceforth be called Nph1 (SEQ ID NO 2). Nph1 is also equivalent to Npo1 (Npr1 homolog oryzae 1).

The acquired resistance genes from wheat (Npr1 homolog 2) will henceforth be called Nph2-1 (SEQ ID NO 7) and Nph2-2 (SEQ ID NO 8). Nph2-1 and Nph2-2 are also equivalent to Npw1 and Npw2, respectively (Npr1 homolog wheat 1 and 2).

The partial sequence for the acquired resistance gene from corn (SEQ ID NO 20) is equivalent to Npc1 (Npr1 homolog corn 1).

"Acquired resistance" refers to an inducible activated defense mechanism in plants treated by certain chemical compounds (activators) or challenged by incompatible pathogens. Acquired in this way, resistance protects plants against subsequent infection by a broad spectrum of different pathogens.

"Antigenic epitope" refers to any discrete segment of a molecule, protein, or nucleic acid capable of eliciting an immune response, wherein the immune response results in the production of antibodies reactive with the antigenic epitope.

"Coding sequence" and "open reading frame" refer to a region of continuous sequential nucleic acid triplets encoding a protein, polypeptide, or peptide sequence.

"Disease resistance" refers to the ability of plants to develop fewer disease symptoms following exposure to a plant pathogen than a susceptible plant that does not exhibit disease resistance. Disease resistance includes complete resistance to the disease and also varying degrees of resistance manifested as decreased symptoms, longer survival or other disease parameters, such as higher yield.

"Homolog" is 70% or more in sequence identity. Significant homology of a sequence very closely related to the probe sequence refers to the sequences hybridizing to the probe at 68° C. overnight (at least 16 hours) and washed at stringent conditions (68° C., final wash with 0.1×SSC/0.1% SDS). Final wash in 2×SSC at 50° C. allows identification of sequences with about 75% homology to the probe. However, the exact relationship between stringency and sequence homology depends on base composition, the length of the probe, and the length of the homologous regions (Hames and Higgins, 1985). Preferably the hybridization conditions refer to hybridization in which the TM value is between 35° C. and 45° C. Most preferably significant homology refers to a DNA sequence that hybridizes with the reference sequence under stringent conditions.

"Hybridization" refers to the ability of a strand of nucleic acid to join with a complementary strand via base pairing.

Hybridization occurs when complementary sequences in the two nucleic acid strands bind to one another.

The "hypersensitive response" (HR) is one plant defense against pathogens. It encompasses a rapid cellular necrosis near the site of the infections that correlates with the generation of activated oxygen species, production of anti-microbial compounds, and reinforcement of host cell walls. Pathogens that elicit an HR on a given host are avirulent on that host, the host is resistant, and the plant-pathogen interaction is incompatible.

"Identical" nucleotide or protein sequences are determined by using programs such as GAP or BestFit from GCG (Genetics Computer Group, Inc., Madison, WI) using the default parameters.

"Nucleic acid" refers to deoxyribonucleic acid (DNA) and ribonucleic acid (RNA).

"Plant" is used herein in a broad sense and refers to differentiated plants as well as undifferentiated plant material, such as protoplasts, plant cells, seeds, plantlets, etc., that under appropriate conditions can develop into mature plants, the progeny thereof, and parts thereof such as cuttings and fruits of such plants.

"Phenotype" refers to traits exhibited by an organism resulting from the interaction of genotype and environment.

"Polyadenylation signal" or "polyA signal" refers to a nucleic acid sequence located 3' to a coding region that promotes the addition of adenylate nucleotides to the 3' end of the mRNA transcribed from the coding region.

"Promoter" or "promoter region" refers to a nucleic acid sequence, usually found upstream (5') to a coding sequence, that controls expression of the coding sequence by controlling production of messenger RNA (mRNA) by providing the recognition site for RNA polymerase or other factors necessary for start of transcription at the correct site.

"Recombinant nucleic acid vector" refers to any agent such as a plasmid, cosmid, virus, autonomously replicating sequence, phage,.or linear or circular single-stranded or double-stranded DNA or RNA nucleotide segment, derived from any source, capable of genomic integration or autonomous replication, comprising a nucleic acid molecule in which one or more nucleic acid sequences have been linked in a functionally operative manner. Such recombinant nucleic acid constructs or vectors are capable of introducing a 5' regulatory sequence or promoter region and a DNA sequence for a selected gene product into a cell in such a manner that the DNA sequence is transcribed into a functional mRNA, which is subsequently translated into a polypeptide or protein. Recombinant nucleic acid constructs or recombinant vectors may be constructed to be capable of expressing antisense RNAs, in order to inhibit translation of a specific RNA of interest.

"Regeneration" refers to the process of growing a plant from a plant cell (e.g., plant protoplast or explant).

"Resistance gene" is a nucleic acid isolate encoding a protein that is directly or indirectly involved in the induction of a signal transduction pathway eventually leading to a plant defense response against any pathogen or insect, upon contact of the plant with that particular pathogen or insect. Resistance gene products are activated in response to pathogen signal molecules termed elicitors.

"Selectable marker" refers to a nucleic acid sequence whose expression confers a phenotype facilitating identification of cells containing the nucleic acid sequence. Selectable markers include those that confer resistance to toxic chemicals (e.g., ampicillin resistance, kanamycin resistance; glyphosate resistance), complement a nutritional deficiency (e.g., uracil, histidine, leucine), or impart a visually distinguishing characteristic (e.g., color changes or fluorescence).

"Structural gene" means a gene that is expressed to produce a polypeptide.

"Structural coding sequence" refers to a DNA sequence that encodes a peptide, polypeptide, or protein that is made by a cell following transcription of the structural coding sequence to messenger RNA (mRNA), followed by translation of the mRNA to the desired peptide, polypeptide, or protein product.

"Transcription" refers to the process of producing an RNA copy from a DNA template.

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

"Transgenic" refers to organisms into which exogenous nucleic acid sequences are integrated.

"Vector" refers to a plasmid, cosmid, bacteriophage, or virus that carries exogenous DNA into a host organism.

The invention relates to acquired resistance genes in plants and methods for their use. Specifically, the invention discloses novel nucleic acid sequences encoding for genes that activate acquired resistance genes in plants, transformed host cells and transgenic plants containing acquired resistance genes, and methods of use for conferring resistance to pathogens in plants. Methods are also disclosed for preparing the transformed host cells and transgenic plants.

Nucleic Acid Sequences

The invention is also directed to a nucleic acid sequence comprising a nucleic acid sequence at least about 70% identical to SEQ ID NO:1, more preferably at least about 75%, 80%, 85%, 90%, or 95% identical to SEQ ID NO:1, and most preferably is SEQ ID NO:1.

Alternatively, the nucleic acid sequence is preferably at least about 70% identical to SEQ ID NQ:5, more preferably is at least about 75%, 80%, 85%, 90%, or 95% identical to SEQ ID NO:5, and most preferably is SEQ ID NO:5.

Alternatively, the nucleic acid sequence is preferably at least about 70% identical to SEQ ID NO:6, more preferably is at least about 75%, 80%., 85%, 90%, or 95% identical to SEQ ID NO:6, and most preferably is SEQ ID NO:6.

The structural nucleic acid sequences may be obtained (i.e., cloned or isolated) from various species of plants, animals, bacteria, and fungi and utilized in the present invention. Preferably, the structural nucleic acid sequence is derived from a plant, fungal, or bacterial source or is chemically synthesized.

Nucleic Acid Hybridization

The nucleic acid sequence may be further identified by its ability to hybridize with a complementary sequence. Nucleic acid hybridization is a technique well-known to those of skill in the art of DNA manipulation. The hybridization properties of a given pair of nucleic acids are an indication of their similarity or identity.

Low stringency conditions may be used to select sequences with lower sequence identities to a target sequence. One may wish to employ conditions such as about 0.15 M to about 0.9 M sodium chloride, at temperatures ranging from about 20° C. to about 55° C.

High stringency conditions may be used to select for nucleic acid sequences with higher degrees of identity to the disclosed sequences (Sambrook et al., 1989).

The high stringency conditions typically involve nucleic acid hybridization in about 2× to about 10×SSC (diluted from a 20× SSC stock solution containing 3 M sodium chloride and 0.3 M sodium citrate, pH 7.0 in distilled water), about 2.5× to about 5× Denhardt's solution (diluted from a 50× stock solution. containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. The high stringency conditions are preferably provided by 6×SSC, 5× Denhardt's solution, 100 mg/mL fish sperm DNA, and 0.1% (w/v) SDS, with an incubation at 55° C. for several hours.

The hybridization is generally followed by several wash steps. The wash compositions generally comprise 0.5× to about 10×SSC, and 0.01% (w/v) to about 0.5% (w/v) SDS with a 15-minute incubation at about 20° C. to about 70° C. Preferably, the nucleic acid segments remain hybridized after washing at least one time in 0.1×SSC at 65° C.

The nucleic acid sequence preferably hybridizes, under low or high stringency conditions, with SEQ ID NO:1, or the complement thereof. Alternatively, the nucleic acid sequence preferably hybridizes, under low or high stringency conditions, with SEQ ID NO:5, or the complement thereof. Alternatively, the nucleic acid sequence preferably hybridizes, under low or high stringency conditions, with SEQ ID NO:6, or the complement thereof.

Protein Sequences

The invention is directed to a protein sequence that preferably is at least about 70% identical to SEQ ID NO:4, more preferably is at least about 75%, 80%, 85%, 90%, or 95% identical to SEQ ID NO:4, and most preferably is SEQ ID NO:4.

Alternatively, the protein sequence preferably is at least about 70% identical to SEQ ID NO:10, more preferably is at least about 75%, 80%, 85%, 90%, or 95% identical to SEQ ID NO:10, and most preferably is SEQ ID NO:10.

Alternatively, the protein sequence preferably is at least about 70% identical to SEQ ID NO:11, more preferably is at least about 75%, 80%, 85%, 90%, or 95% identical to SEQ ID NO:11, and most preferably is SEQ ID NO:11.

To further aid in the study and application of the protein of SEQ ID NOS:4, 10, or 11 antibodies may be prepared. These antibodies may be raised against any portion of the protein that provides an antigenic epitope. The antibodies may be polyclonal or monoclonal. Such an antibody is preferably immunoreactive with SEQ IDNOS:4, 10, or 11.

The protein, which is at least about 70% to 100% identical to SEQ ID NOS:4, 10, or 11, is preferably reactive with such antibodies.

The antibodies may be used to detect the presence of SEQ ID NOS:4, 10, or 11 by ELISA, radioimmunoassay, immunoblot, western blot, immunofluorescence, immunoprecipitation, or any other comparable technique. In addition, a kit may be designed that incorporates one or more of these techniques that use the antibodies described above to detect SEQ ID NOS:4, 10, or 11.

Codon Usage

Due to the degeneracy of the genetic code, different nucleotide codons may be used to code for a particular amino acid. A host cell often displays a preferred pattern of codon usage (Campbell et al., 1990). Nucleic acid sequences are preferably constructed to utilize the codon usage pattern of the particular host cell. This generally enhances the expression of the nucleic acid sequence in a transformed host cell. The nucleic acid sequences disclosed herein preferably utilize the optimal codon usage for bacterial, fungal, and plant host cells.

Modifications of Nucleic Acid Sequences Encoding Proteins for Acquired Resistance Variations in the nucleic acid sequence encoding acquired resistance proteins may lead to mutant acquired resistance protein sequences that display equivalent or superior acquired resistance characteristics when compared to the sequences disclosed herein. Mutations may include deletions, insertions, truncations, substitutions, fusions, shuffling of subunit sequences, and the like.

Mutations to a nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a nucleic acid sequence. Examples include single strand rescue (Kunkel, 1985), unique site elimination (Deng and Nickloff, 1992), nick protection (Vandeyar et al., 1988), and PCR (Costa et al., 1996). Random or non-specific mutations may be generated by chemical agents (for a general review, see Singer and Kusmierek, 1982) such as nitrosoguanidine (Cerda-Olmedo et al., 1968; Guerola et al., 1971) and 2-aminopurine (Rogan and Bessman, 1970), or by biological methods such as passage through mutator strains (Greener et al., 1997).

The modifications may result in either conservative or non-conservative changes in the amino acid sequence. Conservative changes result from additions, deletions, substitutions, etc. in the nucleic acid sequence that do not alter the final amino acid sequence of the protein. Non-conservative changes include additions, deletions, and substitutions that result in an altered amino acid sequence.

Additional methods of making the alterations described above are described by Ausubel et al. (1995); Bauer et al. (1985); Craik (1985); Frits Eckstein et al. (1982); Sambrook et al. (1989); Smith et al. (1981); Osuna et al. (1994); and Walder et al. (1986).

Modification and changes may be made in the sequence of the proteins of the present invention and the nucleic acid segments that encode them and still obtain. a functional molecule that encodes a protein with desirable resistance properties. The following is a discussion based upon changing the amino acid sequence of a protein to create an equivalent, or possibly an improved, second-generation molecule. The amino acid changes may be achieved by changing the codons of the nucleic acid sequence, according to the standard codon table known in the art.

Certain amino acids may be substituted for other amino acids in a protein sequence without appreciable loss of enzymatic activity. It is thus contemplated that various changes may be made in the peptide sequences of the disclosed protein sequences, or their corresponding nucleic acid sequences, without appreciable loss of the biological activity.

In making such changes, the hydropathic index of amino acids may be considered. The importance of the hydropathic amino acid index in conferring interactive biological function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics. These are isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 (Hopp, T. P., issued Nov. 19, 1985) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine, and isoleucine. Changes that are not expected to be advantageous may also be used if these resulted in functional acquired resistance proteins.

Recombinant Vectors

Any of the above mentioned structural nucleic acid sequences may be used to prepare a recombinant vector. The recombinant vector typically comprises, in a 5' to 3' orientation: a promoter to direct the transcription of a structural nucleic acid sequence, a structural nucleic acid sequence, a 3' transcriptional terminator, and a 3' polyadenylation signal. The recombinant vector may further comprise untranslated sequences, transit and targeting sequences, selectable markers, enhancers, or operators.

Means for preparing recombinant vectors are well known in the art. Methods for making recombinant vectors particularly suited to plant transformation are described in U.S. Pat. Nos. 4,971,908, 4,940,835, 4,769,061 and 4,757,011. These types of vectors have also been reviewed (Rodriguez et al., 1988; Glick et al., 1993).

Typical vectors useful for expression of nucleic acids in higher plants are well known in the art and include vectors derived from the tumor-inducing (Ti) plasmid of *Agrobacterium tumefaciens* (Rogers et al., 1987). Other recombinant vectors useful for plant transformation, including the pCaMVCN transfer control vector, have also been described (Fromm et al., 1985).

Promoters

The selection of a suitable promoter depends on the type of host cell in which it will be used. Promoters that function in bacteria, yeast, and plants are all well taught in the art.

The promoter may also be selected on the basis of transcriptional regulation that it provides. Such regulation may include enhancement of transcriptional activity, inducibility, tissue specificity, and developmental stage specificity. In plants, promoters that are inducible, of viral or synthetic origin, constitutively active, temporally regulated, and spatially regulated have been described (Poszkowski et al., 1989; Odell et al., 1985; Chau et al., 1989).

Often-used constitutive promoters include the CaMV 35S promoter (Odell, 1985), the enhanced CAMV 35S promoter, the Figwort Mosaic Virus (FMV) promoter (Richins et al., 1987), the enhanced FMV promoter, the mannopine synthase (mas) promoter, the nopaline synthase (nos) promoter, and the octopine synthase (ocs) promoter.

Useful inducible promoters include promoters induced by salicylic acid or polyacrylic acids (PR-1, Williams et al., 1992), or SA analogs, such as 2,6-dichloroisonicotinic acid (INA) or benzo(1,2,3) thiodiazole-7-carbothioic acid S-methyl ester (BTH) (Gorlach et al., 1996; Kessman et al., 1994), induced by application of safeners (substituted benzenesulfonamide herbicides, Hershey and Stoner, 1991), heat-shock promoters (Ou-Lee et al., 1986; Ainley et al., 1990), a nitrate-inducible promoter derived from the spinach nitrite reductase sequence (Back et al., 1991), hormone-inducible promoters (Yamaguchi-Shinozaki et al., 1990; Kares et al., 1990), the WCI-3 promoter, and light-inducible promoters associated with the small subunit of RuBP carboxylase and LHCP families (Kuhlemeier et al., 1989; Feinbaum et al., 1991; Weisshaar et al., 1991; Lam and Chua, 1990; Castresana et al., 1988; Schulze-Lefert et al., 1989).

Examples of useful tissue-specific, developmentally regulated promoters include the β-conglycinin 7S promoter (Doyle et al., 1986; Slighton and Beachy, 1987) and seed-specific promoters (Knutzon et al., 1992; Bustos et al., 1991; Lam and Chua, 1991; Stayton et al., 1991). Plant functional promoters useful for preferential expression in seed plastids include those from plant storage proteins and from proteins involved in fatty acid biosynthesis in oilseeds. Examples of such promoters include the 5' regulatory regions from such sequences as napin (Kridl et al., 1991), phaseolin, zein, soybean trypsin inhibitor, ACP, stearoyl-ACP desaturase, and oleosin. Seed-specific regulation is discussed in EP 0 255 378.

A suitable promoter may also be induced during a plant defense response against a pathogen infection. Typically, a pathogen infection triggers an induction of a large number of pathogenesis-related (PR) proteins by the infected plant (Bowles, 1990; Bol et al., 1990; Gorlach et al., 1996; Linthorst, 1991). Such PR sequences may encode enzymes involved in phenylpropanoid metabolism (e.g., phenylalanine ammonia lyase, chalcone synthase), proteins that modify plant cell walls (e.g., hydroxyproline-rich glycoproteins, glycine-rich proteins, peroxidases), enzymes that degrade fungal cell walls (e.g., chitinases, glucanases), thaumatin-like proteins, lipoxygenases, cysteine proteases, or proteins with as yet unknown functions. Promoters from the genes Pir7b (Waspi et al., 1998), Rir1a (Mauch et al., 1998), Rir1b (Mauch et al., 1998), and WIR1a (Bull et al., 1992) may be useful in the present invention.

The promoters of these PR sequences may be obtained and utilized in the present invention. Isolation of these PR promoters has been reported from potato plants (Fritzemeier et al., 1987; Cuypers et al., 1988; Logemann et al., 1989; Matton et al., 1989; Schroder et al., 1992), tobacco plants (Martini et al., 1993), and asparagus plants (Warner et al., 1994).

Promoter hybrids can also be constructed to enhance transcriptional activity (Comai, L. and Moran, P. M., U.S. Pat. No. 5,106,739, issued Apr. 21, 1992) or to combine desired transcriptional activity and tissue specificity.

Promoters having particular utility in the present invention include the nopaline synthase (nos), mannopine synthase (mas), and octopine synthase (ocs) promoters, which are carried on tumor-inducing plasmids of Agrobacterium tumefaciens; the cauliflower mosaic virus (CaMV) 19S and 35S promoters; the enhanced CAMV 35S promoter; the Figwort Mosaic Virus (FMV) 35S promoter; the enhanced FMV 35S promoter; the light-inducible promoter from the small subunit of ribulose-1,5-bisphosphate carboxylase (ss-RUBISCO); the EIF-4A promoter from tobacco (Mandel et al., 1995); the 4ASI promoter; the RB7 promoter; the ATEF1 promoter from Arabidopsis; the hsp90 promoter; corn sucrose synthetase 1 (Yang and Russell, 1990); corn alcohol dehydrogenase 1 (Vogel et al., 1989); corn light harvesting complex (Simpson, 1986); corn heat shock protein (Odell et al., 1985); the chitinase promoter from Arabidopsis (Samac et al., 1991); the LTP (Lipid Transfer Protein) promoters from broccoli (Pyee et al., 1995); petunia chalcone isomerase (Van Tunen et al., 1988); bean glycine rich protein 1 (Keller et al., 1989); potato patatin (Wenzler et al., 1989); the ubiquitin promoter from maize (Christensen et al., 1992); the hsp90 promoter (Marrs et al., 1993; Yabe et al., 1994); the sugarcane badnavirus promoter; the rice RC2 promoter; and the actin promoter from rice (McElroy et al., 1990). All of these promoters have been used to create various types of DNA constructs that have been expressed in plants. See, for example, U.S. Pat. No. 5,034,322 in this regard.

Structural Nucleic Acid Sequences

The structural nucleic acid sequence preferably encodes a protein at least about 70% identical to SEQ ID NO:4, more preferably encodes a protein at least about 75%, 80%, 85%, 90%, or 95% identical to SEQ ID NO:4, and most preferably encodes SEQ ID NO:4.

Alternatively, the structural nucleic acid sequence preferably encodes a protein at least about 70% identical to SEQ ID NO:10, more preferably encodes a protein at least about 75%, 80%, 85%, 90%, or 95% identical to SEQ ID NO:10, and most preferably encodes SEQ ID NO:10.

Alternatively, the structural nucleic acid sequence preferably encodes a protein at least about 70% identical to SEQ ID NO:11, more preferably encodes a protein at least about 75%, 80%, 85%, 90%, or 95% identical to SEQ ID NO:11, and most preferably encodes SEQ ID NO:11.

Alternatively, the nucleic acid sequence is preferably at least about 70% identical to SEQ ID NO:1, more preferably is at least about 75%, 80%, 85%,90%, or 95% identical to SEQ ID NO:1, and most preferably is SEQ ID NO:1.

Alternatively, the nucleic acid sequence is preferably at least about 70% identical to SEQ ID NO:5, more preferably is at least about 75%, 80%, 85%, 90%, or 95% identical to SEQ ID NO:5, and most preferably is SEQ ID NO:5.

Alternatively, the nucleic acid sequence is preferably at least about 70% identical to SEQ ID NO:6, more preferably is at least about 75%, 80%, 85%, 90%, or 95% identical to SEQ ID NO:6, and most preferably is SEQ ID NO:6.

The structural nucleic acid sequence may be further identified by its ability to hybridize with a complementary sequence. Various conditions for nucleic acid hybridizations are well taught in the art (Sambrook et al., 1989; Ausubel et al., 1995). The structural nucleic acid sequence preferably hybridizes, under low or high stringency conditions, with SEQ ID NO:1, or the complement thereof. Alternatively, the structural nucleic acid sequence preferably hybridizes, under low or high stringency conditions, with SEQ ID NO:5, or the complement thereof. Alternatively, the structural nucleic acid sequence preferably hybridizes, under low or high stringency conditions, with SEQ ID NO:6, or the complement thereof.

The recombinant vector may further comprise a nucleic acid sequence encoding a transit peptide. This peptide may be useful for directing a protein to the extracellular space or to some other compartment inside or outside of the cell.

The structural nucleic acid sequences may be obtained (i.e., cloned or isolated) from various species of plants, animals, bacteria, and fungi and utilized in the present invention. Preferably, the structural nucleic acid sequence is derived from a plant, fungal, or bacterial source or is chemically synthesized.

Other Elements of the Recombinant Vector

A 3' non-translated region typically provides a transcriptional termination signal and a polyadenylation signal that functions in plants to cause the addition of adenylate nucleotides to the 3' end of the mRNA. These may be obtained from the 3' regions to the nopaline synthase (nos) coding sequence, the soybean 7S storage protein coding sequence, and the pea ssRUBISCO E9 coding sequence, or from the Agrobacterium tumor-inducing (Ti) plasmid (Fischhoff et al., U.S. Pat. No. 5,500,365).

The recombinant vector may further comprise a selectable marker. The nucleic acid sequence serving as the selectable marker functions to produce a phenotype in cells that facilitates their identification relative to cells not containing the marker. Useful selectable markers include GUS, green fluorescent protein (GFP), neomycin phosphotransferase II (nptII), luciferase (LUX), chloramphenicol acetyl transferase (CAT), antibiotic resistance sequences, and herbicide (e.g., glyphosate) tolerance sequences. The selectable marker is preferably a kanamycin, hygromycin, or herbicide resistance marker.

Typically, nucleic acid sequences located a few hundred base pairs downstream of the polyadenylation site serve to terminate transcription. These regions are required for efficient polyadenylation of transcribed mRNA.

Translational enhancers may also be incorporated as part of the recombinant vector. Thus the recombinant vector may preferably contain one or more 5' non-translated leader sequences that serve to enhance expression of the nucleic acid sequence. Such enhancer sequences may be desirable to increase or alter the translational efficiency of the resultant mRNA.

Probes and Primers

Short nucleic acid sequences having the ability to specifically hybridize to complementary nucleic acid sequences may be produced and utilized in the present invention. These short nucleic acid molecules may be used as probes to identify the presence of a complementary sequence in a given sample. Thus, by constructing a nucleic acid probe that is complementary to a small portion of a particular nucleic acid sequence, the presence of that sequence may be assessed. Use of these probes may greatly facilitate the identification of transgenic plants that contain a particular nucleic acid sequence (e.g., a nucleic acid sequence encoding an acquired resistance gene). The probes may also be used to screen cDNA or genomic libraries for additional sequences encoding acquired resistance genes.

Alternatively, the short nucleic acid sequences may be used as oligonucleotide primers to amplify or mutate a complementary nucleic acid sequence using PCR technology. These primers may also facilitate the amplification of related complementary sequences (e.g., related nucleic acid sequences from other species).

The primer or probe is generally complementary to a portion of the nucleic acid sequence that is to be identified, amplified, or mutated. The primer or probe should be of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long.

The primer or probe may be prepared by direct chemical synthesis, by PCR (U.S. Pat. Nos. 4,683,195, and 4,683,202), or by excising the nucleic acid specific fragment from a larger nucleic acid molecule.

Transgenic Plants and Transformed Host Cells

The invention is also directed to transgenic plants and transformed host cells that comprise, in a 5' to 3' orientation: a promoter to direct the transcription of a structural nucleic acid sequence, a structural nucleic acid sequence, a 3' transcriptional terminator, and a 3' polyadenylation signal.

The promoter may be seed selective, tissue selective, constitutive, or inducible. Such promoters include the nopaline synthase (NOS), octopine synthase (OCS), mannopine synthase (mas), cauliflower mosaic virus 19S and 35S (CaMV19S, CaMV35S), enhanced CaMV (eCaMV), ribulose 1,5-bisphosphate carboxylase (ssRUBISCO), figwort mosaic virus (FMV), enhanced FMV, CaMV derived AS4, tobacco RB7, tobacco EIF-4, lectin protein (Lel), 4ASI, RB7, *Arabidopsis* AtEFI, hsp90, rice RC2 promoter, and the sugarcane badnavirus promoter. The structural nucleic acid sequence encodes a protein at least about 70% identical to SEQ ID NO:4, more preferably encodes a protein at least about 75%, 80%, 85%, 90%, or 95% identical to SEQ ID NO:4, and most preferably encodes SEQ ID NO:4.

Alternatively, the structural nucleic acid sequence encodes a protein at least about 70% identical to SEQ ID NO:10, more preferably encodes a protein at least about 75%, 80%, 85%, 90%, or 95% identical to SEQ ID NO:10, and most preferably encodes SEQ ID NO:10.

Alternatively, the structural nucleic acid sequence. encodes a protein at least about 70% identical to SEQ ID NO:11, more preferably encodes a protein at least about 75%, 80%, 85%, 90%, or 95% identical to SEQ ID NO:11, and most preferably encodes SEQ ID NO:11.

Alternatively, the structural nucleic acid sequence is preferably at least about 70% identical to SEQ ID NO:1, more preferably is at least about 75%, 80%, 85%, 90%, or 95% identical to SEQ ID NO:1, and most preferably is SEQ ID NO:1.

Alternatively, the structural nucleic acid sequence is preferably at least about 70% identical to SEQ ID NO:5, more preferably is at least about 75%, 80%, 85%, 90%, or 95% identical to SEQ ID NO:5, and most preferably is SEQ ID NO:5.

Alternatively, the structural nucleic acid sequence is preferably at least about 70% identical to SEQ ID NO:6, more preferably is at least about 75%, 80%, 85%, 90%, or 95% identical to SEQ ID NO:6, and most preferably is SEQ ID NO:6.

The structural nucleic acid sequence may be further identified by its ability to hybridize with a complementary sequence. Various conditions for nucleic acid hybridizations are well taught in the art (Sambrook et al., 1989; Ausubel et al., 1995). The structural nucleic acid sequence preferably hybridizes, under low or high stringency conditions, with SEQ ID NO:1, or the complement thereof. Alternatively, the structural nucleic acid sequence preferably hybridizes, under low or high stringency conditions, with SEQ ID NO:5, or the complement thereof. Alternatively, the structural nucleic acid sequence preferably hybridizes, under low or high stringency conditions, with SEQ ID NO:6, or the complement thereof.

The transformed host cell may generally be any cell that is compatible with the present invention. The transformed host cell preferably is prokaryotic, such as a bacterial cell, and more preferably is an *Agrobacterium, Arthrobacter, Azospyrillum, Clavibacter, Escherichia, Pseudomonas*, or *Rhizobacterium* cell. The transformed host cell preferably is eukaryotic, and more preferably is a plant, yeast, or fungal cell. If a yeast cell is selected to be transformed, it preferably is a *Saccharomyces cerevisiae, Schizosaccharomyces pombe*, or *Pichia pastoris*. If a plant cell is selected to be transformed, it may be of any type capable of being transformed, preferably one with an agronomic, horticultural, ornamental, economic, or commercial value, and more preferably is. an *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice,. rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini cell.

A transgenic plant is. then preferably regenerated from the transformed cell using routine. techniques available to one skilled in the art. The resulting transgenic plant is preferably more resistant to pathogen infection relative to a non-transgenic plant of the same species.

Method for Preparing Transformed Host Cells Containing an Acquired Resistance Gene The invention is further directed to a method for preparing a transformed host cell comprising, in a 5' to 3' orientation: a promoter to direct the transcription of a structural nucleic acid sequence, a structural nucleic acid sequence, a 3' transcriptional terminator, and a 3' polyadenylation signal.

The method generally comprises the steps of selecting a suitable host cell, transforming the host cell with a recombinant vector, and obtaining the transformed host cell (Newell et al., 1991). There are many methods for introducing nucleic acids into host cells. Suitable methods include bacterial infection (e.g., Agrobacterium), binary bacterial artificial chromosome vectors, direct delivery of DNA (e.g., via PEG-mediated transformation, desiccation/inhibition-mediated DNA uptake, electroporation, agitation with silicon carbide fibers, and acceleration of DNA coated particles, etcetera (reviewed in Potrykus et al., 1991).

Technology for introduction of DNA into cells is well known to those of skill in the art. These methods can generally be classified into four categories: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253), and particle acceleration (Johnston and Tang, 1994; Fynan et al., 1993); (3) viral vectors (Clapp, 1993; Lu et al., 1993; Eglitis and Anderson, 1988); and (4) receptor-mediated mechanisms (Curiel et al., 1992; Wagner et al., 1992).

Alternatively, nucleic acids can be introduced into pollen by directly injecting a plant's reproductive organs (Zhou et al., 1983; Hess, 1987; Luo et al., 1988; Pena et al., 1987). The nucleic acids may also be injected into immature embryos (Neuhaus et al., 1987).

The recombinant vector used to transform the host cell typically comprises, in a 5' to 3' orientation: a promoter to direct the transcription of a structural nucleic acid sequence, a structural nucleic acid sequence, a 3' transcriptional terminator, and a 3' polyadenylation signal. The recombinant vector may further comprise untranslated sequences, transit and targeting sequences, selectable markers, enhancers; or operators.

Method For Preparing Transgenic Plants Containing an Acquired Resistance Gene

The invention is further directed to a method for preparing transgenic plants, more resistant to pathogen infections than non-transgenic plants of the same species, comprising selecting a suitable plant cell, transforming the plant cell with a recombinant vector, and obtaining the transformed host cell.

The recombinant vector typically comprises, in a 5' to 3' orientation: a promoter to direct the transcription of a structural nucleic acid sequence, a structural nucleic acid sequence, a 3' transcriptional terminator, and a3' polyadenylation signal. The recombinant vector may further comprise untranslated sequences, transit and targeting sequences, selectable markers, enhancers, or operators.

The regeneration, development, and cultivation of plants from transformed plant protoplasts or explants is well taught in the art (Weissbach and Weissbach, 1988; Horsch et al., 1985). In this method, transformants are generally cultured in the presence of a media that selects for the successfully transformed cells and induces the regeneration of plant shoots (Fraley et al., 1983). These shoots are typically obtained within two to four months.

The shoots are then transferred to an appropriate root-inducing medium containing the selective agent and an antibiotic to prevent bacterial growth. Many of the shoots will develop roots. These are then transplanted to soil or other media to allow the continued development of roots. The method, as outlined, will generally vary depending on the particular plant strain employed.

Preferably, the regenerated transgenic plants are self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transgenic plant may pass along the nucleic acid sequence encoding the acquired resistance protein to its progeny. The transgenic plant is preferably homozygous for the nucleic acid encoding the acquired resistance protein and transmits that sequence to all of its offspring as a result of sexual reproduction. Progeny may be grown from seeds produced by the transgenic plant. These additional plants may then be self-pollinated to generate a true breeding line of plants.

The progeny from these plants are evaluated, among other things, for gene expression and disease resistance (e.g., induction of acquired resistance). The gene expression may be detected by several common methods such as western blotting, northern blotting, immunoprecipitation, and ELISA. Disease resistance is generally tested in the field, greenhouse, or growth chamber under a range of environmental conditions.

EXAMPLES

The following examples further illustrate the present invention. They are in no way to be construed as a limitation in scope and meaning of the claims.

Example 1

Identification of Acquired Resistance Genes From Rice and Wheat

A corn EST (Incyte) database was searched using the *Arabidopsis* Npr1 gene sequence (Cao et al., 1997) to identify monocot homologs. The search was conducted with software from GCG (Genetics Computer Group, Madison, Wis.). This search yielded 19 ESTs with weak DNA homology to Npr1 (25–46% identity at the amino acid level with the predicted Npr1 protein). Cluster analyses indicated that two clusters of ESTs were represented by two corn clones: clone 700214872 corresponded to 4 ESTs; clone 700102819 corresponded to 3 ESTs. Full-length sequencing of corn clone 700214872 showed that it contained a 1385 bp cDNA insert (SEQ ID NO:16), potentially encoding a 381 amino acid protein (SEQ ID NO:17). The putative protein from clone 700214872 aligns with Arabidopsis Npr1 protein from amino acid 220 to C-terminus, spanning the ankyrin repeat domains and the C-terminal half of the protein. This clone was derived from library SATMON016 (filed May 15, 1998 as U.S. application 60/085,533), which was generated from corn sheath tissue.

Corn clone 700102819 contained a smaller 640 bp cDNA. insert (SEQ ID NO:18), potentially encoding a polypeptide of 126 amino acids (SEQ ID NO:19) that aligned with the C-terminal end of *Arabidopsis* Npr1 and confirmed the corn clone 700214872 deduced protein sequence. Assembly of a 2235 bp contig for all corn cDNAs, CPR951 FL (SEQ ID NO:20), potentially encoding a corn protein of 409 amino acids (SEQ ID NO:21), confirmed key monocot-specific domains.

Alignment of a corn clone 700214872 with divergent dicot Npr1 homologs, i.e., *Arabidopsis* and *N. glutinosa* (Ausubel at al., 1998) (FIG. 1), identified two highly conserved regions: Domain 1 with amino acids HRALDSDD, corresponding to Arabidopsis Npr1 position amino acid 270–277 (SEQ ID NO:12), and domain 2 with amino acids ELGRRYF, corresponding to Arabidopsis Npr1 amino acid position 501–507 (SEQ ID NO:13). These regions were used to design the degenerated primers OB09: 5'-CAY ARI GCI YTI GAY WSI GAY GA-3' (SEQ ID NO:14), and OB11: 5'-RAA RWA ICK IYK ICC IAR YTC-3' (SEQ ID NO:15) (Y=C,T; R=A,G; I=inosine; W=A,T; S=G,C; K=G,T).

Figure 2:
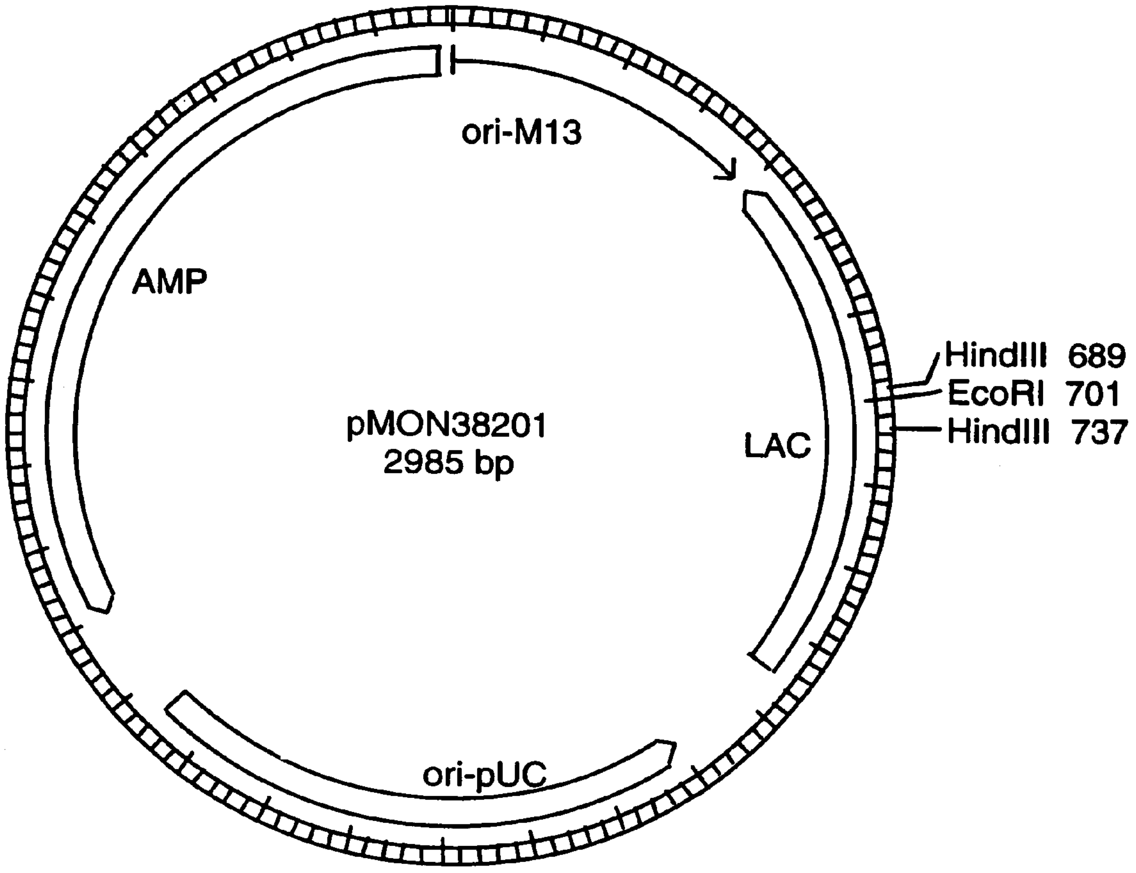
FIG. 2 shows the plasmid pMON38201.

To amplify acquired resistance sequences from monocot sources, a polymerase chain reaction (PCR) was performed using the primers OB09 and OB11. Conditions were optimized for $MgCl_2$ concentration and temperature of primer annealing. A $MgCl_2$ concentration of 2.5–3.0 mM with an annealing temperature of 44° C. produced strong, reproducible PCR amplification products (35 cycles of PCR: 94° C. 5 min/94° C. 1 min/44° C. 45 sec/72° C. 1 min/72° C. 10 min). Under these conditions, amplification of rice (cv. M202), wheat (cv. Bobwhite), barley (cv. Perry), and corn (cv. B-73) genomic DNA yielded two fragments of about 1.5 kb and 0.7 kb. Use of the OB09–OB11 primers in RT-PCR of rice (cv. M202), wheat (cv. Bobwhite), barley (cv. Perry) RNA from different tissue sources yielded bands approximately.0.7 kb in size. Total RNA was purified using TRIZOL®) reagent (GibcoBRL, Life Technologies, Rockville, Md.) according to manufacturer's instructions. Purified poly A+ mRNA was recovered from these different sources using PolyATract mRNA Isolation System IV (Promega, Madison, Wis.). For the reverse transcription reaction, 4 μL of polyA+ mRNA was used as template with a DT anchor primer to generate a cDNA under conditions recommended by the manufacturer (CloneTech, Palo Alto, Calif.). The resulting cDNA product was subjected to PCR using the OB09-OB11 primers (35 cycles of PCR: 94° C. 5 min/94° C. 1 min/45° C. 45 sec/72° C. 1 min/72° C. 10 min at cycle 35). PCR products from these experiments were separated by agarose gel electrophoresis, amplified fragments eluted from the gel (Qiaex II Gel Extraction Kit) according to manufacturer's directions (Qiagen, Valencia, Calif.), cloned into pMON38201 (FIG. 2), which accepts direct cloning of PCR products, and the inserts subjected to sequence analysis (ABI PRISM® Dye Terminator Cycle Sequencing, Perkin-Elmer, Foster City, Calif.).

By employing this strategy, we were able to clone fragments of genes believed to function in the acquired resistance pathways of rice and wheat. These homologs have been called Nph, with the rice gene designated Nph1 and wheat gene designated Nph2.

The rice Nph1 fragment was isolated from etiolated rice tissue and from young green leaf tissue by RT-PCR as described above. Total RNA was purified using TRIZOL® reagent (GibcoBRL, Life Technologies, Rockville, Md.) according to manufacturer's instructions. Poly A+ RNA was recovered using PolyATract mRNA Isolation System IV according to manufacturer's protocol (Promega, Madison, Wis.). For reverse transcription, 0.5 μg of purified, poly A+ RNA was used as template, with the cDNA generated using a DT anchor primer under conditions recommended by the manufacturer (CloneTech, Palo Alto, Calif.). Four microliters of the resulting cDNA product was then PCR amplified using OB09–OB11 primers. The 0.7 kb amplification products from both tissue sources were treated independently. The final PCR products were separated by agarose gel electrophoreses, purified from the agarose gel (Qiagen, Valencia, Calif.), cloned directly into pMON38201, and transformed into *E. coli* bacterial cells (DH5α; GibcoBRL, Life Sciences Technologies, Rockville, Md.). Full length sequencing of the inserts (ABI PRISM® Dye Terrninator Cycle Sequencing, Perkin-Elmer) confirmed strong homology to the corn clone 700214872. Six inserts were analyzed and found to share an identical 705 bp fragment (SEQ ID NO:3).

The wheat Nph2 fragment was also recovered by RT-PCR. Total RNA was isolated from two-week-old, green leaf tissue from wheat (cv. Bobwhite) using TRIZOL® reagent (GibcoBRL) according to manufacturer's instructions. Poly A+ RNA was recovered using PolyATract mRNA Isolation System IV (Promega, Madison, Wis.). For reverse transcription, 0.5 μg of purified, poly A+ RNA was used as template, with the cDNA generated using a DT anchor primer under conditions recommended by the manufacturer (CloneTech, Palo Alto, Calif.). The resulting cDNA product (4 μL) was then PCR amplified using OB09–OB11 primers. The final 0.7 kb amplification product was agarose gel purified (Qiagen, Valencia, Calif.), cloned into pMON38201, and transformed into *E. coli* bacterial cells (DH5a; GibcoBRL, Life Sciences Technologies, Rockville, Md.). Bacterial colonies were screened by transferring the bacterial DNA onto positively charged nylon membrane (HYBOND N+; Amersham Life Science Inc., Arlington Heights, Ill.) and probing with a random primed $^{32}P$ labeled probe developed using the corn clone 700214872. Positively hybridizing clones were subjected to sequence analysis (ABI PRISM® Dye Terminator Cycle Sequencing, Perkin-Elmer). Full length sequencing of three inserts showed an identical 706 bp fragment (SEQ ID NO:9) with strong homology to the corn clone 700214872 (SEQ ID NO:16).

Example 2

Cloning the Nph1 Gene From Rice

Cloning of the full length Nph1 gene from rice was facilitated by using the cloned 0.7 kb rice PCR fragment (SEQ ID NO:3) as a probe. Specifically, an internal 471 bp PstI fragment from the PCR product was used to screen a λgt11 5' STRETCH-cDNA library generated from etiolated rice seedlings (*Oryza sativa* L. indica var. IR36; CloneTech, Palo Alto, Calif.). Bacteriophage were plated on NZY media using Y1090R-bacterial host cells (CloneTech). Approximately $2\times10^6$ independent plaques were screened by transferring the phage DNA to positively charged nylon membrane (HYBOND N+, Amersham Life Science). The internal PstI fragment from the rice PCR product was prepared as a probe by $^{32}P$ random priming and used to screen the library by overnight hybridization at 62° C. in Rapid Hyb buffer(Amersham Life Science). The filters were washed once with 2×SSC/0.1% SDS (10 min/room temperature) and once 1×SSC/0.1% SDS (40 min/65° C.). After autoradiography, 77 positively hybridizing plaques were identified. Phage DNA was isolated from 15 plaques and the insert DNA amplified by PCR using the λgt11 forward and λgt11 reverse primers (35 cycles of PCR: 94° C. 5 min/94° C. 1 min/55° C. 1 min/72° C. 1.5 min/72° C. 10 min at cycle 35). The two largest inserts amplified were 2.3 kb in size. The PCR products from these two largest inserts were agarose gel electrophoresed, purified from the gel, cloned in the vector pGEM-T (Promega), and transformed into XL1-Blue *E. coli* bacteria cells (Stratagene, La Jolla, Calif.). Sequence analysis demonstrated that both clones were identical at the nucleotide level (SEQ ID NO:1).

The full length cDNA for rice Nph1 contained a 2368 nucleotide insert encompassing 618 nucleotides of 5' untranslated region upstream of the predicted first ATG and 322 nucleotides of 3' untranslated region beyond the predicted stop codon (SEQ ID NO:2). The predicted Nph1 coding region extends for 1428 nucleotides (SEQ ID NO:1), potentially encoding a polypeptide 475 amino acids in length (SEQ ID NO:4). The rice Nph1 cDNA (SEQ ID NO:1) shares 79.3% nucleotide identity with the partial corn clone 700214872 (SEQ ID NO:16), but only 52.9% identity with the *Arabidopsis* Npr1 cDNA (Cao et al., 1997). At the predicted amino acid level, rice Nph1 (SEQ ID NO:4) is 82.4% identical with the partial corn clone 700214872 (SEQ ID NO:17) but shares only 41% amino acid identity with *Arabidopsis* Npr1 (Cao et al., 1997). Alignment of the rice Nph1 and *Arabidopsis* Npr1 protein sequences necessitates the introduction of 4 gaps. The rice Nph1 protein sequence is 113 amino acids shorter at the 5' end than the *Arabidopsis* Npr1 protein sequence.

Table 1 summarizes the percentage identity of the rice Nph1, wheat Nph2-1, corn clone 700214872, and *Arabidopsis* Npr1 nucleotide and predicted protein sequences, respectively.

TABLE 1

Percentage Identity between Rice Nph1, Wheat Nph2-1, Corn clone 700214972, and *Arabidopsis* Npr1 nucleotide and predicted protein sequences

| | Rice Nph1 | Wheat Nph2-1 | Corn clone 700214972 | *Arabidopsis* Npr1 |
|---|---|---|---|---|
| Rice Nph1 | 100% | DNA: 82% Protein: 82.6% | DNA: 79.3% Protein: 82.4% | DNA: 52.9% Protein: 41% |
| Wheat Nph2-1 | DNA: 82% Protein: 82.6% | 100% | DNA: 78.8% Protein: 79.5% | DNA: 49% Protein: 39.1% |

Example 3

Isolation of the Wheat Nph2-1 and Nph2-2 Genes

To isolate the wheat Nph2 genes, a commercial wheat 5'-STRETCH cDNA library from 13-day-old *T. aestivum* (var. TAM 107) post-emergence seedlings grown in ambient light was screened (CloneTech, Palo Alto, Calif.). Screening probes were prepared by PCR amplification of the wheat Nph2 PCR fragment (SEQ ID NO:9) using primers OB01 (SEQ ID NO:22) and OB02 (SEQ ID NO:23), and by PCR amplification of the 1.38 kb insert of the corn clone 700214872 (SEQ ID NO:16) amplified using gene-specific primers OB18 (SEQ ID NO:24) and OB19 (SEQ ID NO:25). Amplified wheat and corn PCR fragments were agarose gel purified and labeled using $^{32}$p random priming. A 1:2 concentration ratio of wheat probe:corn probe was used in library screening.

Bacteriophage containing the library were plated on NZY media using Y1090R-bacterial host cells (CloneTech). Approximately $2\times10^{6}$ independent plaques were screened by transferring the phage DNA to positively charged nylon membrane (HYBOND N+, Amersham Life Science), incubating the filter with the mixed probe overnight at 60° C. in 20 mL Rapid-Hyb buffer (Amersham Life Science) with 100 μg/mL fish sperm DNA. Filters were washed once at 2×SSC (10 min/room temperature), twice at 60° C. (2×SSC/0.1% SDS), and once at 60° C. (1×SSC/0.1% SDS), and subjected to autoradiography. Of the 45 identified positive phage, two were found to contain inserts of approximately 2.4 kb. Phage DNA from these clones was isolated, and the inserts were independently subcloned into EcoRI site of pBluescript SK+ plasmid (Stratagene, La Jolla, Calif.). Full-length sequence analyses confirmed that both clones encoded wheat Nph2-homologous sequences. Wheat clone 1 contained a 2420 bp insert (SEQ ID NO:7) with 1824 bp potential coding region (SEQ ID NO:5) specifying a 607 amino acid putative protein, designated Nph2-1 (SEQ ID NO:10). Wheat clone 2 had an insert size of 2120 bp (SEQ ID NO:8) with an 1830 bp open reading frame (SEQ ID NO:6) that is expected to encode a 609 amino acid protein designated Nph2-2 (SEQ ID NO:11).

Pairwise alignment of Nph2-1 and Nph2-2 revealed 98% identity between the predicted protein sequences. Wheat Nph2-1 and Nph2-2 are most similar to the corn clone 700214872, with the nucleotide and predicted protein sequences sharing about 79% identity. The wheat Nph2-1/Nph2-2 sequences share about 82% nucleotide identity with rice Nph1, and about 83% predicted protein sequence identity. Comparison of wheat Nph2-1 with *Arabidopsis* Npr1 shows a low level of shared nucleotide and predicted protein identity, at 49% and 39%, respectively. Alignment of wheat Nph2-1 and Arabidopsis Npr1 protein sequences necessitates introduction of 14 gaps, using default GAP parameters (Genetics Computer Group, Inc., Madison, Wis.). Multiple alignments with the deduced amino acid sequences of the wheat Nph2-1 homolog with the Arabidopsis Npr1, the corn clone 700214872, and rice Nph1 demonstrated that Nph2-1 shares significant sequence homology in the region of ankyrin repeats and C-terminal part of the protein but contained a unique N-terminal sequence. The predicted start codon of wheat Nph2-1/2-2 sequences added an additional 25 amino acids to the N-terminus of Nph2-1/2-2 relative to *Arabidopsis* Npr1, and an additional 137 amino acids at the N-terminus relative to rice Nph1.

Example 4

Southern Blot Analysis of Nph1 and Nph2 in Monocots

The gene copy number of Nph homologs in monocot species was examined using monocot-specific probes in Southern blot analysis. The cloned wheat Nph2-1 cDNA (SEQ ID NO:7) in pBluescript SK+ plasmid (Stratagene; 30 cycles of PCR: 94° C. 5 min/94° C. 1 min/55° C. 1 min/72° C. 1.5 min/72° C. 10 min at cycle 30) was amplified using KS and SK primers (Stratagene, La Jolla, Calif.) to generate the Nph2 probe. Genomic DNA isolated from wheat (cv. Bobwhite), barley (cv. Perry), corn (cv. B-73), and rice (cv. M202) was digested with either EcoRI or HinDIII restriction enzyme, fragments were separated on agarose gels, transferred to a HYBOND N+ nylon filter (Amersham Life Sciences, Inc., Arlington Heights, Ill.), and incubated with the wheat Nph2-1 probe prepared by $^{32}$P random priming. Southern hybridization was performed overnight at 65° C. using 20 mL Rapid-Hyb buffer (Amersham Life Science, Inc., Arlington Heights, Ill.) with 100 μg/mL fish sperm DNA. Filters were washed twice at 2×SSC/0.1% SDS (65° C., 20 min) and twice at 0.5×SSC 0.1% SDS (65° C. 20 min.). Hybridizing bands were detected by autoradiography.

A simple pattern of hybridization was found, with only one or two bands detected in each of these monocot species. In rice, corn, barley, and wheat, the pattern of hybridization is consistent with the presence of a single related gene, suggesting that genes related to Nph2 do not appear to be part of a large gene family. Compared to rice, the wheat and barley hybridization signals appeared more intense, presumably due to the strong homology of the wheat probe to the wheat and barley genes. Also, in the case of wheat, the stronger hybridization signal could also be partially attributed to multiple copies of the same gene represented in the hexaploid wheat genome.

Example 5

Assignment of Wheat Nph2 Homologs on the Wheat Genome

The position of wheat Nph2 gene on chromosome three in the wheat genome was defined using the Chinese Spring nullisomic-tetrasomic lines (Sears, 1966). The euploid parental line was compared to lines that are nullisomic in each one of the three chromosome sets. Total genomic DNA was isolated from the collection of aneuploids and analyzed by Southern blot for the alteration of Nph2 hybridizing bands. Genomic DNA was extracted from wheat nullisomic-tetrasomic lines, digested using EcoRi, separated on an agarose gel, and fragments transferred to nylon membrane (HYBOND N+, Amersham Life Science). The 0.7 kb wheat PCR product for the Nph2 gene (as in Example 3 using OB01/OB02 primers) was prepared by $^{32}P$ random priming and used as a probe. Hybridization was conducted overnight at 65° C. in 20 mL Rapid-Hyb buffer (Amersham Life Sciences) with 100 μg/mL fish sperm DNA. Filters were washed at 65° C.: twice for 20 min in 2×SSC/0.1% SDS, twice for 20 min in 1×SSC/0.1% SDS, and twice for 20 min in 0.1×SSC/0.1% SDS. Autoradiography of the hybridized membrane demonstrated the presence of the Nph2-hybridizing fragment on homologous group 3 of wheat chromosomes, with corresponding absence of bands in the nullisomic 3A (N3DT3A), 3B (N3BT3A), or 3D (N3AT3B) aneuploid lines.

A number of agronomically valuable traits have been localized on the group 3 homologous chromosomes in monocotyledonous plant species. Resistance genes Lr24, Lr27, Lr32, Sr35 were placed on genetic maps of wheat chromosome group 3. Quantitative trail loci (QTLs) for plant height (denso), heading date, and kernel yield were mapped to the barley chromosome 3H. Comparative chromosome mapping between monocot species revealed that collinear arrangement of the markers is consistent between chromosomes of homologous groups within related plant species. Therefore, we speculate that an isolated Nph2 gene from wheat chromosome group 3 could be linked to the agronomically valuable traits mapped on the barley chromosome 3H.

Example 6

Production and Use of Antibodies Directed Against Npr1 Homologs

In order to track the accumulation of dicot Npr1 and monocot Nph-1 and Nph-2 homologous proteins, we generated polyclonal antibodies with wide species cross-reactivity. Polyclonal antibodies were raised against a fusion protein of a partial sequence of tomato Npr1 (in collaboration with Dr. X. Dong, Duke University) in the following way. The HinDIII C-terminal fragment of the tomato Npr1 homolog (180 aa; Glu 398-Stop 577 [SEQ ID NO:36]) was cloned into the HinDIII site of pRSETB vector (Invitrogen Corp., Carlsbad, Calif.) to create a polyhistidine fusion protein of 226 amino acids with a predicted molecular mass of 25.6 kDa. Protein overexpression in E. coli (strain BL2 1; Invitrogen, Carlsbad, Calif.) was induced through the addition of 1 mM IPTG to growth media, growing cells at 37° C. for an additional 2 hours. Cells were harvested by centrifugation and the pellet lysed by addition of 8M urea, 0.1 M Na-phosphate, 0.010 M Tris/HCl pH 8.0 for 1 hr at room temperature. Extracts were bound to an equilibrated affinity column composed of Ni-NTA resin (Qiagen, Valencia, Calif.). The column was washed with the binding buffer and treated with the elution buffer (8M urea, 10 mM Tris/HCl pH 6.8, 100 mM EDTA). The eluted polyhistidine fusion protein was dialyzed against PBS buffer overnight (4° C.) and used as an immunogen for production of polyclonal antibodies in rabbits (200 μg primary immunization/100 μg first boost/50 μg subsequent immunizations).

Antiserum recovered from immunized rabbits (Pocono Rabbit Farm and Laboratory, Inc., Canadesis, Pa.) was used at 1:5,000 dilution and evaluated by western blot analysis against whole plant extracts and protein recovered from *E. coli* expressing the target fusion protein. Plant extracts for western analysis and ELISA determinations were recovered as following. Approximately 100 mg fresh tissue was ground to a fine powder on dry ice using a microfuge pestle and extracted for 30–60 min at 4° C. in buffer [0.05M Tris-Cl,(pH 7.2), 0.05 M NaF, 0.150 M NaCl, 0.5% NP-40, 1 mM PMSF, 1 mM protease inhibitor cocktail (Sigma, St. Louis, Mo.)]. The extract was pelleted (10,000 μl 10 min/4° C.), supernatant recovered, and protein concentration determined (Ausubel et al., 1995). For western analysis, a range of total extracted protein was tested (20–100 μg/lane); for ELISA, 50–100 μg/well was typically assayed.

Western analysis followed standard protocols as described by Ausubel et al. (1995) using the ECL western blotting analysis system (Amersham Life Science) and x-ray film exposure to visualize hybridizing proteins. Total protein extracts were solubilized in SDS-PAGE sample buffer and separated on 8–16% SDS-PAGE gradient gels. Separated proteins were electrotransferred at 100 volts onto nitrocellulose membrane (Protran BA 85, 0.45 μm; Midwest Scientific, Valley Park, Mo.) in 0.025M Tris-Cl, 0.192 M glycine, pH 8.3 with 10% (v/v) methanol. Western blots were washed 5 min in PBS buffer (Boehringer Mannheim, Indianapolis, Ind.) with 0.05% Tween-20 (PBST), blocked in PBST plus 5% (w/v) Carnation nonfat dry milk (Nestle Food Company, Glendale, Calif.) for 1 hr at room temperature or overnight at 4° C. Blots were then washed with PBST (3×10 min/room temperature) and challenged with primary antibody solution (1:5,000 antisera in PBST) for 1 hr at room temperature. After primary antibody incubation, blots were washed (3×5 min/PBST) and incubated for 1 hr/room temperature with secondary antibody (anti-rabbit IgG conjugated horseradish peroxidase in PBST). Blots were washed (3×5 min PBST/1×5 min PBS) and recognized bands visualized using the ECL kit according to manufacturer's specifications (Amersham Life Sciences).

Titration experiments using purified fusion protein demonstrated that this antisera can target the fusion protein at a level of 10–20 ngaane in westem blot analysis. Extracts from a broad variety of monocot and dicot species were assayed. In each case, an endogenous plant protein of around 65–66 kDa was recognized, which corresponds to the approximate molecular mass for Arabidopsis Npr1. This antisera recognizes single bands in protein extracts from rice, wheat, soybean, potato, tobacco, and tomatQ. The protein. extracts. were isolated from non-induced plants, suggesting these proteins are constitutively present in all species examined.

These polyclonal antibodies have enabled monitoring of Nph1 and Nph2 protein expression and accumulation under different conditions. ELISA protocols can be customized for optimum resolution depending on antibody and protein target. For ELISA of dicot and monocot samples, we coated microtiter assay plates overnight at 4° C. with antisera diluted 1:1000 in coating buffer (15 mM $Na_2CO_3$, 35 mM $NaHCO_3$, pH 9.3). Wells were washed (3×3 min/PBST), and extracted samples diluted in PBST with ovalbumin (0.2% w/v; PBSTO) to the appropriate concentration and allowed to bind overnight at 4° C. The wells were washed (3×3 min/PBST), and 200 μL of alkaline phosphatase conjugate (diluted 1:2,000 in PBSTO) added per well and incubated (4 hr/37° C.). Wells were washed with PBST, and freshly prepared phosphatase substrate (97 mL diethanolamine/800 μL $H_2O$) added, and optical density monitored at 405 nm. Purified fusion protein served as a concentration standard.

ELISA tests have been optimized for dicots and monocots after chemical or pathogen induction of acquired resistance, and we have thus verified protein accumulation correlative with heightened transcription of the corresponding gene. We anticipate these antibodies will prove instrumental in measuring the overexpression of Nph1 and Nph2-1/2-2 protein in transgenic plants, under non-induced conditions and under conditions that may induce acquired resistance.

Example 7

Induced Acquired Resistance in Rice Enhances Expression of Nph1 and Confers Resistance Against *Magnaporthe grisea* fungus To examine whether expression of Nph1 is also coordinately regulated with activation of AR in rice, we identified a chemical inducer of AR and determined whether treatment of rice plants with this inducer boosted transcript levels of Nph1. Dichloro-2,6-isonicotinic acid (INA), a well-studied activator of AR (Ryals et al., 1996), was tested for its efficacy to induce Nph1 transcription and condition AR in rice. Fourteen-day-old rice plants (cv. M202) were grown under greenhouse conditions and sprayed with 0.5 mM INA in 20% acetone/80% water (v/v) plus 0.05% Tween 20 (v/v) for treated plants. Mock-treated plants were sprayed with the acetone/water/Tween 20 solution only. Three days after treatment, plants were inoculated with the biotrophic pathogen Magnaporthe grisea, causal agent of rice blast. Freshly isolated spores of *M. grisea* (3–5×$10^4$ spores/mL) suspended in water and Tween 20 (0.025% v/v) were sprayed uniformly on the leaves of treated plants using a Devilbiss hand-held sprayer. Plants were incubated at 24° C., in the dark, under 100% humidity conditions for 24 hr. Plants were then shifted into a 12 hr light/dark cycle growth chamber, and disease symptoms monitored over the course of 7 days.

Figure 3:
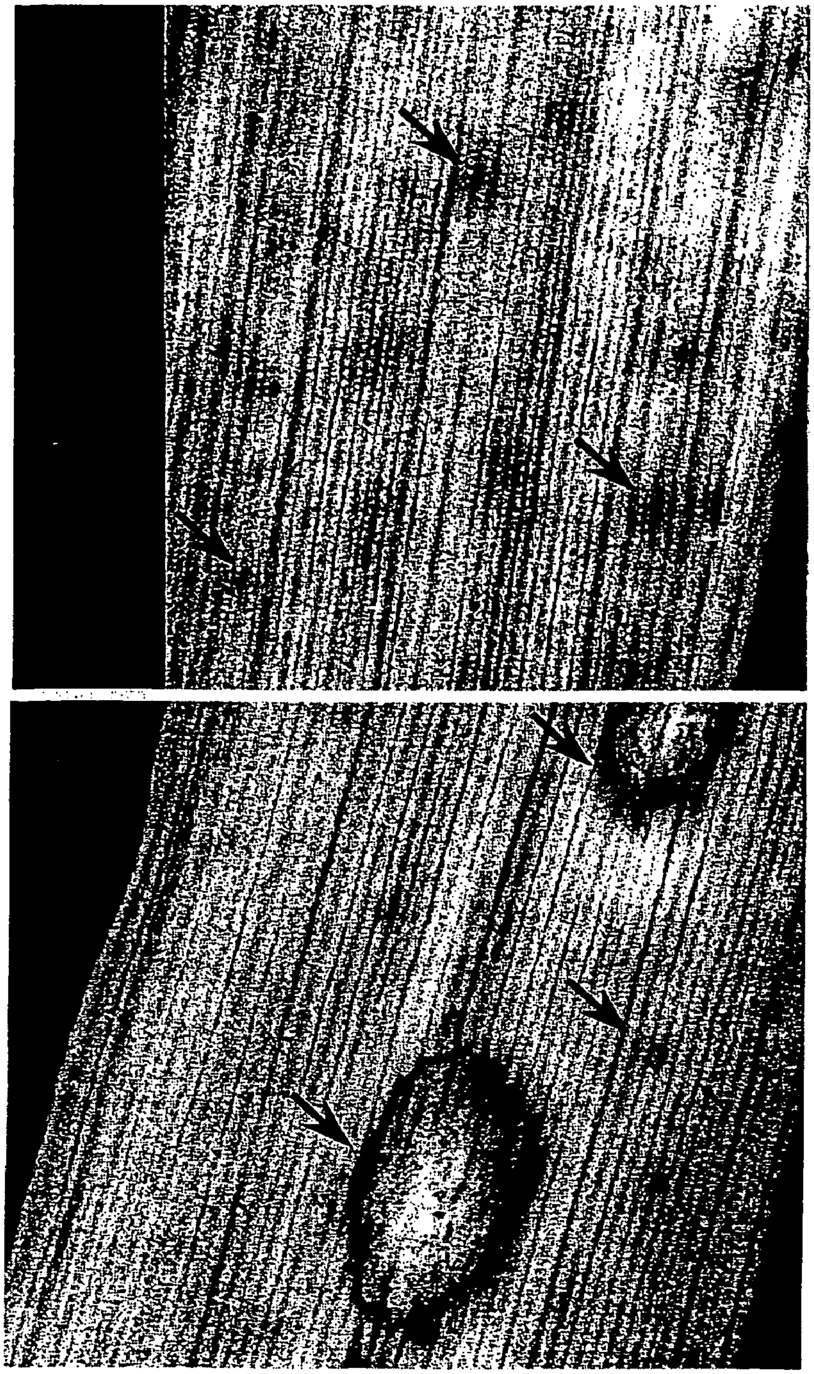
FIG. 3 shows the induction of AR in rice (cv. M202) by chemical treatment with INA and protection against rice blast fungus (*Magnaporthe grisea*).

By day 5, strong rice blast disease symptoms were evident on the control plants, appearing as large, spreading lesions typical of rice blast disease. Plants pre-treated with INA, however, displayed strong resistance against the pathogen, with only small flecks of necrosis or cell death evident on the inoculated leaves (FIG. 3). No disease symptoms or fungal sporulation was seen on INA-treated plants. This result demonstrates (1) that chemically induced AR in rice promotes pathogen resistance and (2) that induced AR in the rice cultivar M202 protects against rice blast fungus.

The influence of INA treatment on Nph1 gene activation was evaluated by northern blot analysis of INA-treated and untreated rice leaves (cv. M202). Total RNA was isolated from INA-treated leaf tissues using TRIZOL® reagent (GibcoBRL, Life Technologies) before the onset of AR (0 hours after treatment), and at time intervals after treatment. Total RNA was separated by denaturing agarose gel electrophoresis (20 μg/lane) and transferred to HYBOND N+ membranes (Amersham Life Science). The rice Nph1 probe was generated using an internal 0.47 kb PstI DNA fragment of the PCR Nph1 gene (SEQ ID NO:3) that was agarose gel purified and prepared using $^{32}P$ random priming. Filters were hybridized overnight at 62° C. with 20 mL Rapid-Hyb (Amersham Life Science) with the radiolabeled rice Nph1 DNA probe. After hybridization, filters were washed once at room temperature (2×SSC/0.1% SDS, 10 min), twice at 65° C. (1×SSC/0.1% SDS, 20 min), and subjected to autoradiography.

Figure 4:
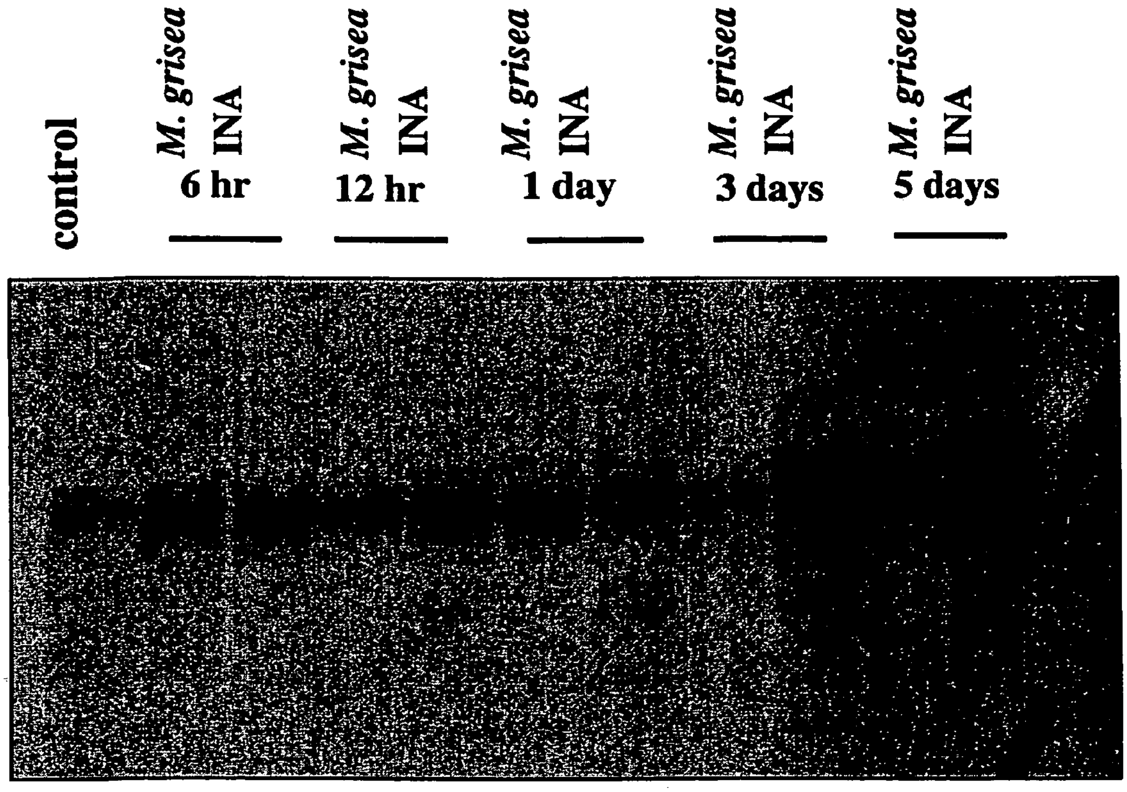
FIG. 4 shows the induction pattern of rice Nph1 after INA treatment and after challenge with rice blast fungus (*Magnaporthe grisea*) by northern blot analysis.

We found spraying with INA induced a twofold to threefold accumulation of Nph1 transcript, with peak expression three days post-INA treatment (FIG. 4). By day five, the final time point of the experiment, Nph1 transcription remained high. The maximal induction level of approximately threefold higher than non-induced control for rice Nph1 is comparable to induced transcription levels reported for *Arabidopsis* Npr1 (Cao et al., 1998). The same northern blot experiment also surveyed the temporal expression of Nph1 in rice (cv. M202) challenged with the Magnaporthe grisea pathogen, using inoculation conditions described above. Tissue was harvested, total RNA prepared, and northern blot analysis performed as detailed previously. Pathogen challenge only transiently up-regulated the expression of Nph1. One day after infection, pathogen-induced Nph1 transcription was boosted to the levels induced by INA treatment, but by day three, Nph1 expression in the pathogen challenged plants was back to non-induced control levels. In contrast, INA-induced plants showed persistently high levels of Nph1 expression to at least day five post-treatment, suggesting that persistently high levels of Nph1 may aid in fostering acquired resistance and protect against blast infection.

Nph1 protein accumulation correlates with increases in Nph1 gene transcription. Protein extracts from rice (cv, M202) that were mock treated or INA treated (12 hrs and 5 days) were compared by ELISA (as described in Example 6). No increased Nph1 protein was detected 12 hours after INA spraying. However, by day 5 post-INA treatment, we found a reproducible 1.7-fold rise in Nph1 protein accumulation. This boost in accumulated protein correlates well with the heightened transcription levels of Nph1 over the same timecourse.

The longevity of induced AR was assayed by challenging INA-treated rice (cv. M202) with *M. grisea* over a longer timecourse. A population of rice plants was sprayed once with 0.5 mM INA [20% acetone/80% water (v/v) plus 0.05% Tween 20 (v/v)] and subsets of plants, both treated and untreated controls, were infected at different timepoints with the rice blast fungus as described above. We found that chemically conditioned AR persisted for more than thirty days after the single INA treatment. At each timepoint, the INA-treated plants demonstrated consistently high resistance to rice blast infection, whereas parallel control plants were uniformly diseased.

We predict that overexpression of Nph1 in transgenic rice will promote an enhanced accumulation of the Nph1 protein and allow a stronger response to pathogen attack, and subsequently, promote a more effective, long-lived “immunity” period in transgenic plants. By expressing Nph1 transgenically, we expect to achieve strong and uniform AR after pathogen challenge. We anticipate that a variety of rice diseases will be combated through overexpression of Nph1, including those caused by fungal, bacterial, and viral pathogens. Transgenic Nph1 expression can be further optimized by driving the transgene with constitutive promoters, such a pFMV, pe35S, or sugarcane badnavirus promoter, for expression throughout the plant, or by using tissue-specific promoters to drive Nph1 expression in particular regions of the plant, such as roots or leaves, or in particular cell types, such as epidermal, vascular, or mesophyll cells.

Example 8

Wheat Nph2 Expression is Inducible and Developmentally Regulated

To determine the relationship between wheat Nph2 gene expression and AR, we treated wheat plants with INA and monitored powdery mildew disease and Nph2 transcription. Treatment with INA has been demonstrated to.activated the AR pathway in wheat as indicated by transcriptional activation of a limited number of marker genes and by enhanced disease resistance (Gorlach et al., 1996). Greenhouse grown, 14-day-old wheat plants (cv. TAM 107) were sprayed either with 1 mM INA (dichloro-2,6-isonicotinic acid) in 20% acetone/80% water (v/v) plus 0.05% Tween 20 (v/v) or with the spray solution alone (mock-treated controls). Five days after treatment, treated and mock-treated controls were inoculated with wheat powdery mildew pathogen (*Erysiphe graminis* f sp hordei). For powdery mildew disease testing, condia from previously infected plants were dislodged onto the foliage of the test plants, which then remained in the growth chamber of the inoculated plants. Conditions in the chamber were maintained at 20° C. with a 12 hr/12 hr day/night light cycle, 300 μE light intensity, 80% relative humidity; plants are subirrigated twice daily. Disease symptoms for INA treated plants and untreated controls were scored 7 days later.

Figure 5:
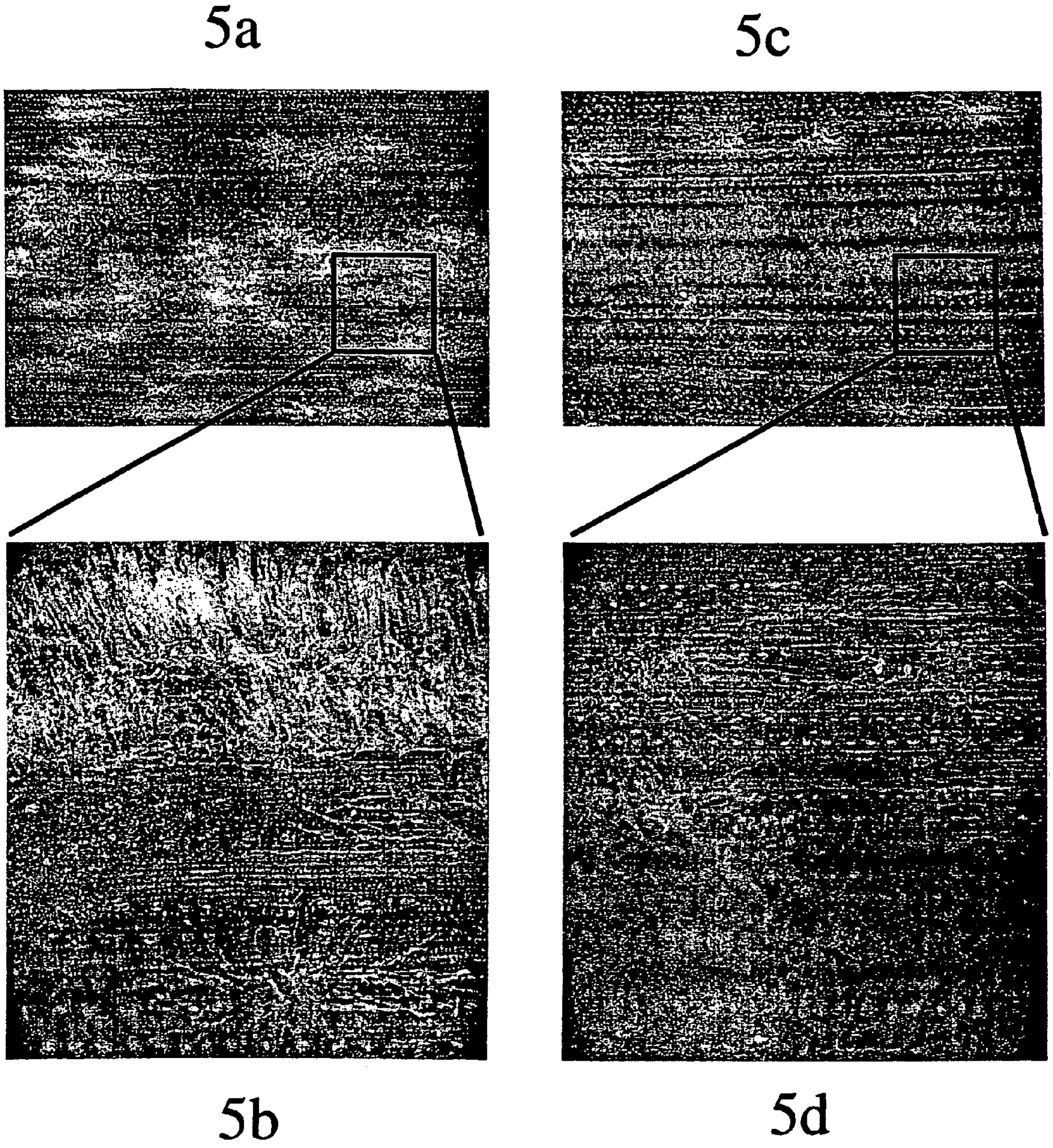
FIG. 5 illustrates the induction of AR in wheat (cv. TAM107) after INA treatment and protection against powdery mildew fungus (*Erysiphe graminis* f sp *hordei*). 5*a*) shows a mock sprayed control at low magnification, while 5*b*) shows a higher magnification of a smaller selected area. 5*c*) shows a low magnification view of a portion of a leaf sprayed with 200 ppm INA, while 5*d*) shows a higher magnification of a smaller area of the same leaf .

Wheat plants sprayed with INA showed fewer foci of fungal growth and displayed enhanced resistance, with 60% control of wheat powdery mildew in replicated trials (FIG. 5). In contrast, control plants were strongly diseased and showed many strong foci of fungal growth. These data demonstrate that treatment of. the wheat cultivar TAM107 with INA enhances acquired resistance that is effective against powdery mildew.

To molecularly assess the uptake of INA and activation of downstream genes, transcription of two wheat genes identified as being either INA-inducible (WCI-2; Gorlach et al., 1996) or pathogen-inducible (WIR-2; Kmecl et al., 1995) were evaluated under different induction conditions in the wheat cultivar Bobwhite. Fourteen-day-old wheat plants were sprayed with 1 mM INA in 20% acetone/80% water (v/v) plus 0.05% Tween 20 (v/v), mock-treated with the spray solution (-INA), or challenged with *Erysiphe graminis* f sp *hordei* (powdery mildew fungus) as described above. Leaf tissue was harvested at day three, and total RNA isolated using TRIZOL® reagent (GibcoBRL) according to the manufacturer's instructions. Ten micrograms of total RNA was agarose gel separated and transferred to HYBOND N+ nylon (Amersham Life Science) membranes. The DNA probe for WCI-2 gene was prepared by PCR amplification using gene-specific primers OB28 (SEQ ID NO:26) and OB29 (SEQ ID NO:27). The DNA probe for WIR-2 was prepared by PCR amplification of the plasmid containing the WIR-2 cDNA, using M13 Forward and Reverse primers (Stratagene). In both cases, PCR was performed using the following conditions: 35 cycles at 94° C. 5 min/94° C. 1 min/45° C. 45 sec/72° C. 1 min/72°C. 10 min (cycle 35). PCR-derived probes were agarose gel purified, labeled by $^{32}P$ random priming, added to 20 mL Rapid-Hyb (Amersham) with 100 μg/mL fish DNA, and the filters hybridized overnight at 60° C. Filters were washed at 65° C. two times at 2×SSC/0.1% SDS (20 min. each), two times at 0.1×SSC/0.5% SDS (20 min. each), and subjected to autoradiography.

In wheat cultivar Bobwhite, the WCI-2 gene is specifically induced by INA in duplicate experiments with no induction detected by pathogen challenge. The pathogen-specific gene WIR-2 is slightly induced by INA but strongly induced by wheat powdery mildew (*E. graminis* f sp *hordei*) in this wheat cultivar. These results support activation of the INA-inducible acquired resistance pathway in Bobwhite wheat as monitored by an identified marker for acquired resistance.

Figure 6:
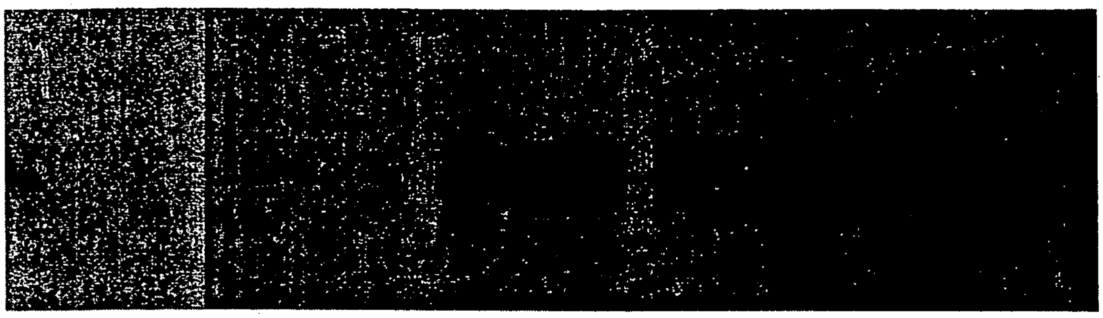
FIG. 6 shows a northern blot analysis of the induction profile of wheat Nph2 gene expression in wheat after INA treatment. Northern blot was probed with maize EST 700214872 Npr1 homolog. 0.5 μg of wheat mRNA was loaded per lane. Lane 1, time "0" plants; Lane 2, INA treated plants at 24 hours; Lane 3, INA treated plants at 48 hours; Lane 4, INA treated plants at 72 hours; Lane 5, INA treated plants at 96 hours.

The induction of the wheat Nph2 gene under INA and pathogen-induced conditions was tested (FIG. 6). Wheat (cv. Bobwhite) plants were sprayed with 1 mM INA or mock-treated, as described above. Total RNA was recovered from the INA-treated leaves before the onset of AR (0 hours after treatment) and after the local onset of AR (24 and 72 hours) as described above. RNA (10 μg) was separated by denaturing agarose gel electrophoresis, transferred to HYBOND N+ membranes (Amersham Life Sciences), and hybridized with the Nph2 probe. The wheat Nph2 probe was generated by PCR of the original Nph2-1 cDNA (SEQ ID NO:7) using KS and SK primers (Stratagene; 30 cycles of PCR: 94° C. 5 min/94° C. 1 min/55° C. 1 min/72° C. 1.5 min/72° C. 10 min at cycle 30). The PCR fragment was agarose gel purified and prepared by $^{32}P$ random priming for use as a probe. Conditions for northern blot analysis were as described above.

We demonstrated that by day three, INA treatment resulted in 1.5- to 2-fold up-regulation in expression of Nph2. The timing and induction of wheat Nph2 is similar to that demonstrated with Nph1 in rice. These results confirm that the acquired resistance pathway appears to be activated in the Bobwhite cultivar. However, the AR response of Bobwhite does not effectively protect the plant from powdery mildew infection, whereas the wheat cultivar TAM107 has a highly effective INA-inducible acquired resistance response that provides strong defense against powdery mildew. We are extending this analysis, evaluating both INA-induced powdery mildew resistance and activation of downstream marker genes, to identify wheat cultivars exhibiting strong transcriptional activation and disease resistance. This survey initially included the wheat cultivars Kanzler, Slejpner, Ritmo, Tremie, Rialto, Soisson, Brigadier.

We anticipate that the inducible AR pathway may have different strengths and effectiveness between cultivars within the same species. This may be due to the effectiveness of key regulatory proteins in the AR pathway, such as Nph2. The wheat cultivar TAM107 was the source of Nph2-1 and Nph2-2 genes and may represent a source of superior Nph2 alleles. We expect that overexpression of TAM107 Nph2 alleles in weaker cultivars, such as Bobwhite, may serve to enhanced the AR response transgenically. Overexpression of the TAM107 Nph2 alleles in cultivars with strong AR may lead to enhancement of resistance, conceivably resulting in a stronger response or broadening of the spectrum of pathogen defense.

In addition to Nph2, we hypothesize that genes involved in stress adaptation may be up-regulated during the AR response. For example, the heat shock protein gene hsp90 has been shown to be involved in cellular stress adaptation (Ali et al., 1998; Marrs et al., 1993). To test this hypothesis, we performed an identical northern blot analysis as above to determine the timing and influence of INA and pathogen challenge on hsp90 gene expression. The probe for barley hsp90 was prepared by RT-PCR (see Example 1). First strand cDNA was synthesized from polyA RNA (2.5 μg) extracted from barley (cv. Morex) using oligo dT primer (Stratagene). Approximately 125 ng of first strand cDNA was used as template to PCR amplify 452 bp fragment of a pathogen-inducible barley hsp90 (GeneBank accession x67960) using OB38 (SEQ ID NO:28) and OB39 (SEQ ID NO:29; 35 cycles of PCR: 94° C. 5 min/94° C. 1 min/44° C. 45 sec/72° C. 1 min/72° C. 10 min). The PCR fragment was cloned into pMON38201 (FIG. 2) and sequence confirmed to be a partial hsp90 cDNA (ABI PRISM® Dye Terminator Cycle Sequencing, Perkin-Elmer). The PCR product was agarose gel purified, $^{32}$p labeled by random priming, and used as a probe. The same northern blots used for Nph2 and WCI-2 were probed for hsp90 gene expression. We found that hsp90 was strongly induced in wheat after INA treatment, with an identical timing and pattern as Nph2, indicating that hsp90 may serve as another marker gene for activation of acquired resistance.

We evaluated the developmental pattern of wheat Nph2 transcription to determine the level of expression under non-induced conditions. Wheat plants (cv. Bobwhite) grown under growth chamber conditions (12 hr/12 hr day/night cycle) were harvested after 7 days. Plants were removed from potting soil, roots washed in tap water, and plants divided into the following samples: roots, coleoptiles, leaf base, and the leaves divided into five equal segments above the base of the blade (above coleoptile=leaf segment 1) to the leaf tip (leaf segment 5). Total RNA (10 μg/lane) was isolated, and northern blot analysis was performed as described above, using the 0.7 kb Nph2 PCR fragment as probe. Filters were hybridized overnight at 65° C., washed once at room temperature (2×SSC/0.1% SDS, 5 min), twice at 65° C. (1×SSC/0.1% SDS, 20 min), once at 65° C. (0.5×SSC/0.1% SDS), and subjected to autoradiography.

Figure 7:
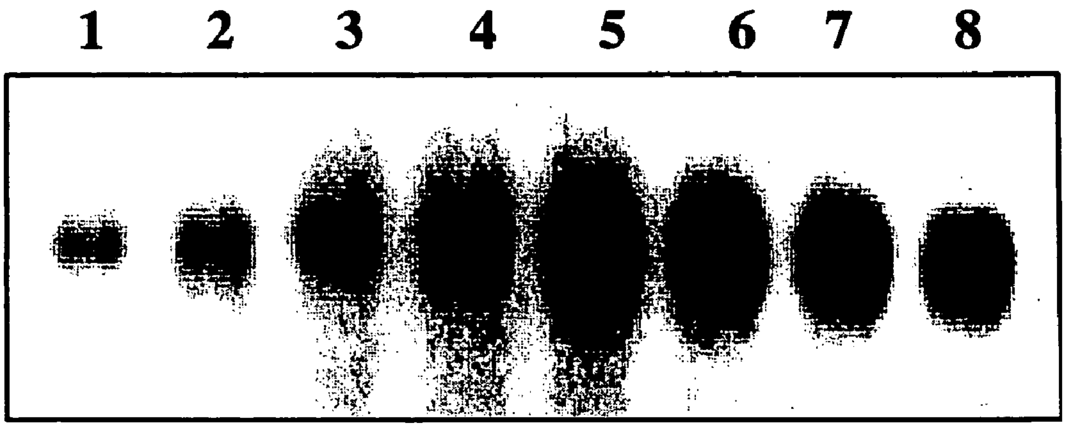
FIG. 7 shows a northern blot analysis of the developmental expression pattern of wheat Nph2 in cultivar TAM107. Northern blot was probed with a 0.7 kb wheat Nph 2 PCR fragment. 15 μg of wheat (cv. Bobwhite) mRNA was loaded per lane. Lane 1, root tissue; Lane 2, coleoptile; Lane 3, leaf base; Lane 4; leaf segment 1; Lane 5, leaf segment 2; Lane 6, leaf segment 3; Lane 7, leaf segment 4; Lane 8, leaf segment 5 (leaf tip).

Northern blot analysis demonstrated an elevated expression of Nph2 in the middle part of wheat leaves (FIG. 7), which corresponds to the zone of cell division and elongation. In contrast, Nph2 expression in the other portions of the leaf and in the root was low. By transgenically overexpressing Nph2 globally in all tissue types or by directing expression to particular cell types or tissues, we anticipate that particular classes of pathogens may be effectively controlled.

Example 9

Identification of Monocot Nph Genes

To identify plants expressing Nph2 wheat homologs that are strongly INA-responsive, we compared expression levels of both Nph2 and downstream response genes in INA-treated and untreated plants of the following accessions: *T. aestivum*-8 accessions; *T. dicoccum*-7 accessions; *T. monococcum*-7 accessions; *T. durum*-8 accessions; *T. tauschii*-33 accessions. Plants were greenhouse grown, treated with INA (or mock treated), total RNA isolated, and northern blot analysis performed using the Nph2 PCR fragment, the hsp90, or the WCI-2 probes (detailed in Example 8). Filters were hybridized overnight at 65° C., washed once at room temperature (2×SSC/0.1% SDS, 5 min), twice at 65° C. (1×SSC/0.1% SDS, 20 min), once at 65° C. (0.5×SSC/0.1% SDS), and hybridizing bands visualized by autoradiography.

Northern blot analyses revealed that induction of Nph2 is up-regulated 1- to 2.5-fold after INA treatment in all studied accessions. Much greater variations in gene inducibility were observed for downstream response genes. The highest levels of two downstream response genes, encoding heat shock 90 protein, hsp90 (Marts et al., 1993), and lipoxygenase (WCI-2; Gorlach et al., 1996) respectively, were observed in the accessions PI538722 (cv. *T. monococcum*), TA5023 (cv. *T. durum*), and TA1599 (cv. *T. tauschii*).

Example 10

Transformation of Monocot Plants With Nph1 and Nph2

Transformation of the rice Nph1 and wheat Nph2 genes into monocot plant species was facilitated by the assembly of molecular constructs suitable for transgenic plant expression. Several approaches were taken, including assembly of constructs for Agrobacterium-mediated transformation and for particle bombardment transformation.

Rice Agrobacterium Transformation

Figure 8:
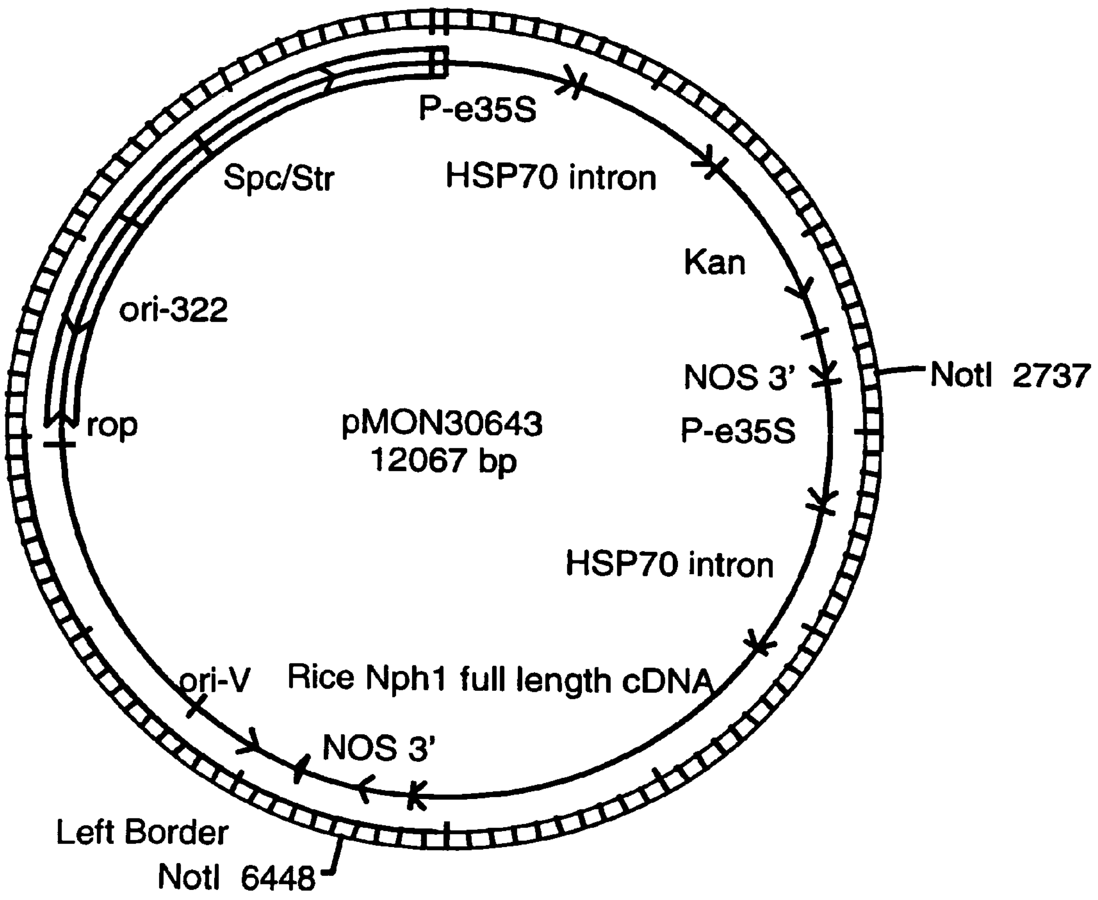
FIG. 8 shows the pMON30643 binary plasmid for rice transformation which contains a rice Nph1 cDNA along with the endogenous rice 5' leader sequence. T-DNA structures of the binary cosmid vector include: LB=left border; RB=right border; P-e35S=enhanced 35S promoter of cauliflower mosaic virus; Kan=coding region for Tn5 neomycin phosphotransferase II; Nos 3'=termination sequences of the nopaline synthase gene.

Rice Nph1 and wheat Nph2 constructs were prepared for rice transformation. Three initial constructs were made for Agrobacterium-mediated transformation, two for particle bombardment. Assembly of the binary plasmid with rice Nph1 gene containing the 5' untranslated region involved the following steps. The plasmid carrying Nph1 (Example 2) was digested with restriction enzymes NcoI and EcoRV, the 1.9 kb fragment gel purified, and cloned into the NcoI/EcoRI (blunt) sites of pMON19648 shuttle vector. This created a cassette of enhanced 35S promoter-hsp70 intron-Nph1cDNA- Nos 3' flanked by NotI restriction sites. The cassette was recovered as a NotI 3.7 kb fragment and cloned into the corresponding NotI site of the binary pMON18634. The final binary plasmid carrying Nph1 containing the 5' UTR is pMON30643 (FIG. 8).

Figure 9:
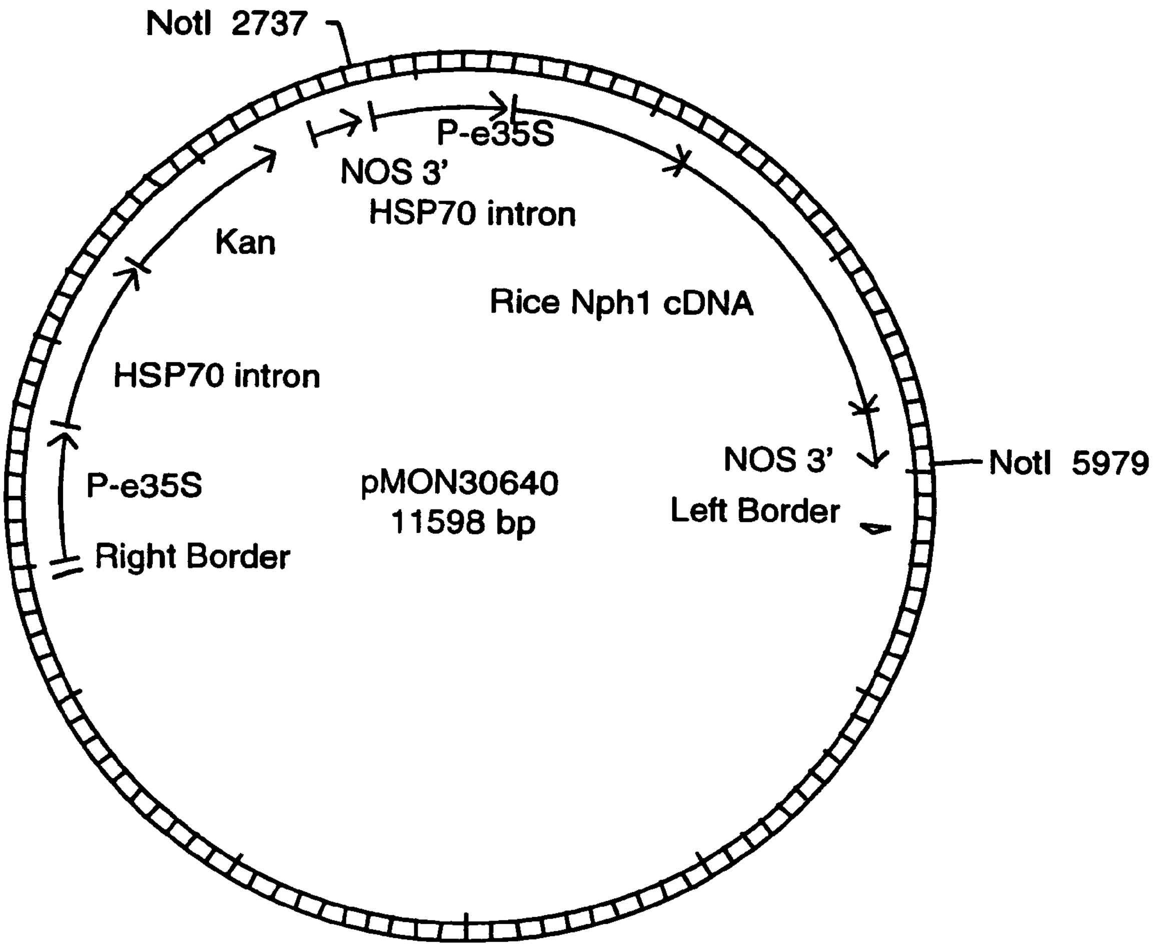
FIG. 9 depicts the pMON30640 binary plasmid for rice transformation which contains a rice Nph1 cDNA corresponding to the predicted coding region and lacking the rice 5' leader sequence.

A second version of Nph1 lacking the 5' UTR was constructed by PCR amplification of the Nph1 cDNA in pGEMT plasmid (Example 2) using Rice NcoI primer (SEQ ID NO:34) and NS-10 primer (SEQ ID NO:35) to generate a 386 bp fragment, which was purified using QIAquick PCR purification kit (Qiagen). The PCR product was digested with NcoII/Nar1 restriction enzymes to yield a 83 bp. fragment, which was used to replaced the endogenous NcoI/Nar1 fragment in Nph1 full length cDNA, utilizing an NcoI site in the plasmid polylinker to deleted the entire 5' UTR. The PCR modification repositioned the novel NcoI site immediately upstream of the first methionine codon in the predicted Nph1 coding sequence. The plasmid carrying the modified Nph1 gene was restriction digested with NcoI/EcoRV, the 1.5 kb fragment agarose gel purified, and subcloned into pMON19648 as described to create the pMON30639 shuttle vector. The cassette carrying e35S promoter-hsp70 intron- Nph1 (lacking 5' UTR)-Nos 3' terminator sequence was liberated as a NotI fragment and subcloned into pMON 18364 to generate the pMON30640 binary plasmid (FIG. 9).

Figure 10:
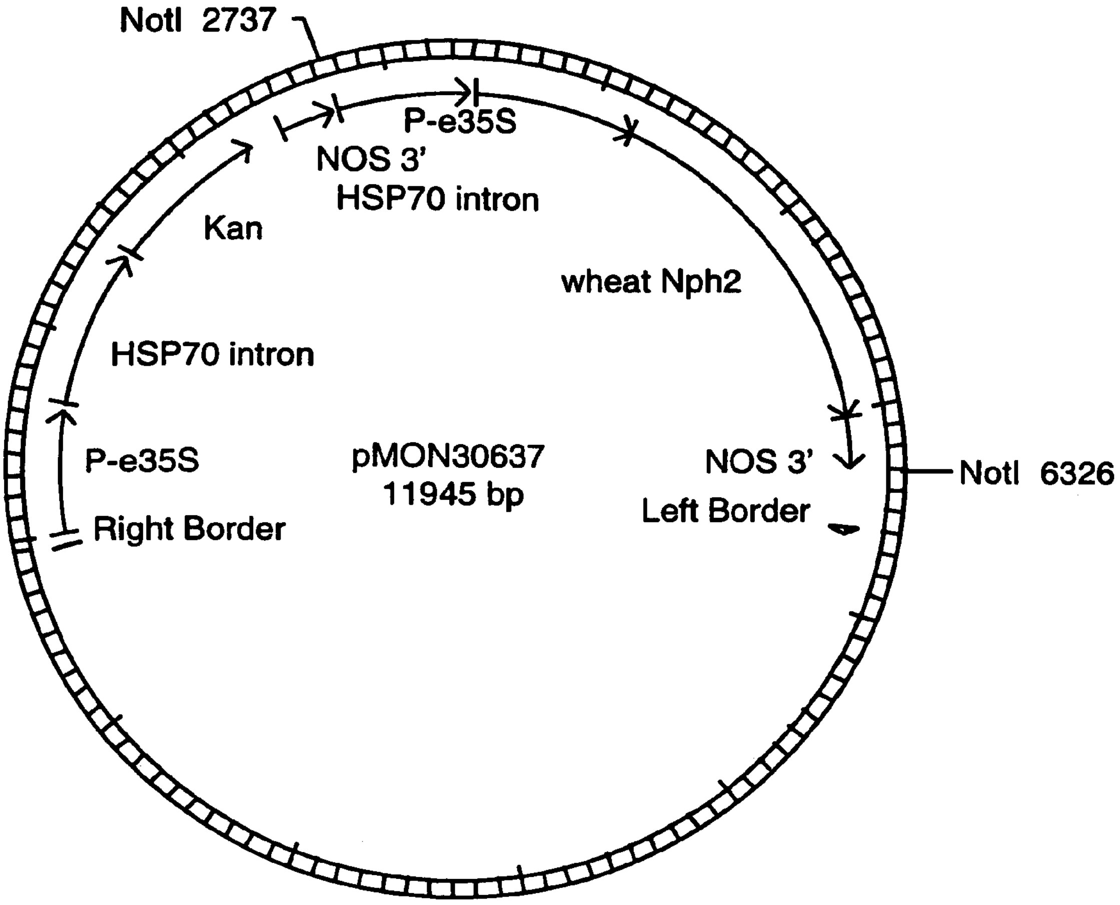
FIG. 10 shows the pMON30637 binary plasmid for rice transformation which contains a wheat Nph2-1 cDNA corresponding to the predicted coding region used.

The wheat Nph2-1 cDNA was also assembled in a binary plasmid for rice transformation. Several steps were required to subclone the Nph2-1 gene from the original Bluescript SK+vector (Stratagene; Example 3) into the final binary vector suitable for Agrobacterium-mediated transformation of monocot plants. The Nph2-1 cDNA was modified at the 3' and 5' ends to provide restriction sites suitable for later subcloning into a shuttle vector. Modification at the 5' end was accomplished by PCR amplification of the Nph2-1 cDNA using OB-63 (SEQ ID NO:32) and OB-64 (SEQ ID NO:33) to generate a 175 bp fragment, which was purified using QIAquick PCR purification kit (Qiagen). The PCR product was digested with ClaI/NarI restriction enzymes to yield a 83 bp fragment, which was used to replaced the endogenous ClaI/NarI fragment in Nph2-1. The PCR modification introduced a novel NcoI site immediately upstream of the first methionine codon in the predicted Nph2-1 coding sequence. Modification at the 3' end of Nph2-1 was accomplished by PCR amplification of the Nph2-1 cDNA using the OB-61 (SEQ ID NO:30) and OB-62 primers (SEQ ID NO:3 1). The amplified 280 bp fragment was purified as above and digested with the restriction enzymes XbaI/BsmI to yield a 170 bp fragment, which was used to replace the endogenous XbaI/BsmI fragment in Nph2-1. This replacement introduced a unique EcoRI restriction site at the 3' end of Nph2-1, downstream from the predicted stop codon. Sequences through the 5' and 3' modified regions were confirmed (ABI PRISM® Dye Terminator Cycle Sequencing, Perkin-Elmer). The plasmid carrying the modified wheat Nph2-1 cDNA was restriction digested with NcoI/EcoRI to release a 1.8 kb fragment, which was subcloned into the NcoI/EcoRI sites of pMON19846 to create the pMON30636 shuttle vector. The enhanced 35S promoter-hsp70 intron-Nph2-1-Nos 3' cassette was liberated from the shuttle vector by NotI digestion and cloned into the NotI site of pMON18364. The final binary carrying Nph2-1 is pMON30637 (FIG. 10).

Method of Transformation

Stock plants and explant tissue:

Harvest immature embryos of Japonica rice variety M202 at 7–11 days post-anthesis. Collect panicles in a container with reverse osmosis (RO) water. Swirl panicles in RO water with a drop of mild detergent (Tween 20). Rinse 3× in RO water. Swirl panicles in 70% ethanol for approximately 60 seconds. Rinse with RO water. Remove seed coats. Place dehusked seeds in RO water. Place in sterile container and rinse with 70% ethanol for approximately 30 seconds. Remove ethanol with sterile pipette. Add 50% bleach plus 1 drop of Tween 20. Cover and put on shaker at 150 rpm for at least 30 minutes at room temperature. Rinse 6× with sterile RO water. Remove embryos.

*Agrobacterium* culture and inoculation:

A disarmed *Agrobacterium* strain C58 (ABI) harboring a binary vector was used for all the experiments. Cultures of *Agrobacterium* were initiated from glycerol stocks or from a freshly streaked plate and grown overnight at 26° C.–28° C. with shaking (approximately 150 rpm) to mid-log phase (about $OD_{660}$=1–1.5) in liquid LB medium, pH 7.0 (Miller, 1972) containing 50 mg/L kanamycin, 50 mg/L streptomycin and spectinomycin, and 25 mg/L chloramphenicol with 200 μM acetosyringone (AS). The cells were centrifuged for 15 min at 4° C. at 5000 rpm. The pellet was rinsed/resuspended with MSVI media, containing 2.2 g/L MS salts,1 mL/L MS vitamins (1000X stock), 115 mg/L proline, 10 g/L glucose, 20 g/L sucrose. Cells were centrifuged for 15 min at 4° C. at 5000 rpm. The *Agrobacterium* cells were resuspended in the inoculation medium (MSPL) and the density was adjusted to an $OD_{660}$ of 1. Add MSPL (MS salt, 2.2 g/L; MS vitamins, 1 mL of 1000x stock; proline, 115 mg/L; glucose, 26 g/L; sucrose, 68.5 g/L) with acetosyringone at 1 μL/5 mL of MSPL to the pellet of *Agrobacterium*, bringing it to the desired OD. On the inside of a sterile petri dish, place 75–100 μL droplets of Agrobacterium. Place 5 embryos in each droplet. Incubate 15 minutes at room temperature. Remove the *Agrobacterium* droplets. Place embryos on co-culture medium (MS salt, 2.2 g/L; MS vitamins, 1 mL of 1000x stock; thiamine HCI, 0.5 mg/L; proline,l 15 mg/L; glucose, 10 g/L; sucrose, 20 g/L; 2,4-D, 2 mg/L; pichloram, 2.2 mg/L; low EEO agarose, 5.5 g/L; acetosyringone, 200 μM; $AgNO_3$, 20 μM) and incubate for 1–3 days at 23° C. After one day, embryos were transferred to Delay media, containing 4.4 mg/L MS salts, 1 mL/L MS vitamins (1000X stock), 1 mg/L Thiamine HCL, 20 g/L sucrose, 500 mg/L glutamine, 750 mg/L Magnesium Chloride, 100 mg/L Casein Hydrolysate, 2 mg/L 2,4-D, pH at 5.8, 2 g/L Phytagel. After autoclaving, add 2.2 mg/L pichloram, 500 mg/L carbenicillin, 20 μM silver nitrate (1.7 mLL of a 2 mg/mL stock).

Selection and Regeneration

After 7 days at 24° C. in the dark on delay medium, the immature embryos were transferred to NIPT1 (Table 2) supplemented with 40 mg/L G418 and 250 mg/L carbenicillin. After 1 week, the embryos were subcultured into small pieces and placed on pre-regeneration medium (NPT2) supplemented with 40 mg/L G418 and 250 mg/L carbenicillin. After 2 weeks, transfer pieces to NPT3 supplemented with 25 mg/L G418 and 100 mg/L carbenicillin, place in percival, 16hr photoperiod at 24° C. After 2 weeks, when green shoots start to form, transfer all greening areas to NPT4 in phytatrays, supplemented with 25 mg/L G418 and 100 mg/L carbenicillin. After 2–4 more weeks, non-transformed plants will be stunted and will not grow to the top of the phytatray. Retain clusters of plants that have grown to the top of the phytatrays and have root hairs on the roots. Gently split plants apart and put individual plants in NPT4 phytatrays supplemented with 25 mg/L G418 and 100 mg/L carbenicillin. Plants can be sent to the greenhouse at this point (when they have reached the top of the phytatrays and have a good root system with root hairs.)

TABLE 2

Supplemental Components in Basal Media[1]

| Components | NPT1 | NPT2 | NPT3 | NPT4 |
|---|---|---|---|---|
| 2,4-D (mg/L) | 2.0 | 0.2 | — | — |
| Pichloram (mg/L)[2] | 2.2 | — | — | — |
| Glutamine (g/L) | 0.5 | — | — | — |
| Sucrose (g/L) | 20.0 | 20.0 | 120.0 | 60.0 |
| $MgCl_2$ (g/L) | 0.75 | — | — | — |
| Casein Hydrolysate (g/L) | 0.1 | — | — | — |
| Abscisic Acid(mg/L)[2] | — | .052 | — | — |
| NAA (mg/L)[2] | — | — | 1.0 | — |
| Kinetin (mg/L)[2] | — | — | 1.0 | — |
| BAp(mg/L)[2] | — | — | 2.0 | — |
| pH | 5.8 | 5.8* | 5.8 | 5.8 |
| 2.5N HCL[2] | — | 280 μl | — | — |
| phytagel (g/L) | 2.0 | 2.5 | 2.5 | 2.5 |

[1]All media contain basal salts (MS basal salts) and vitamins (MS vitamins) from Murashige and Skoog (1962).
[2]Filter sterilized and added after autoclaving.
*Final pH of NPT2 will be 4.0

Rice Particle Bombardment Transformation

Figure 11:
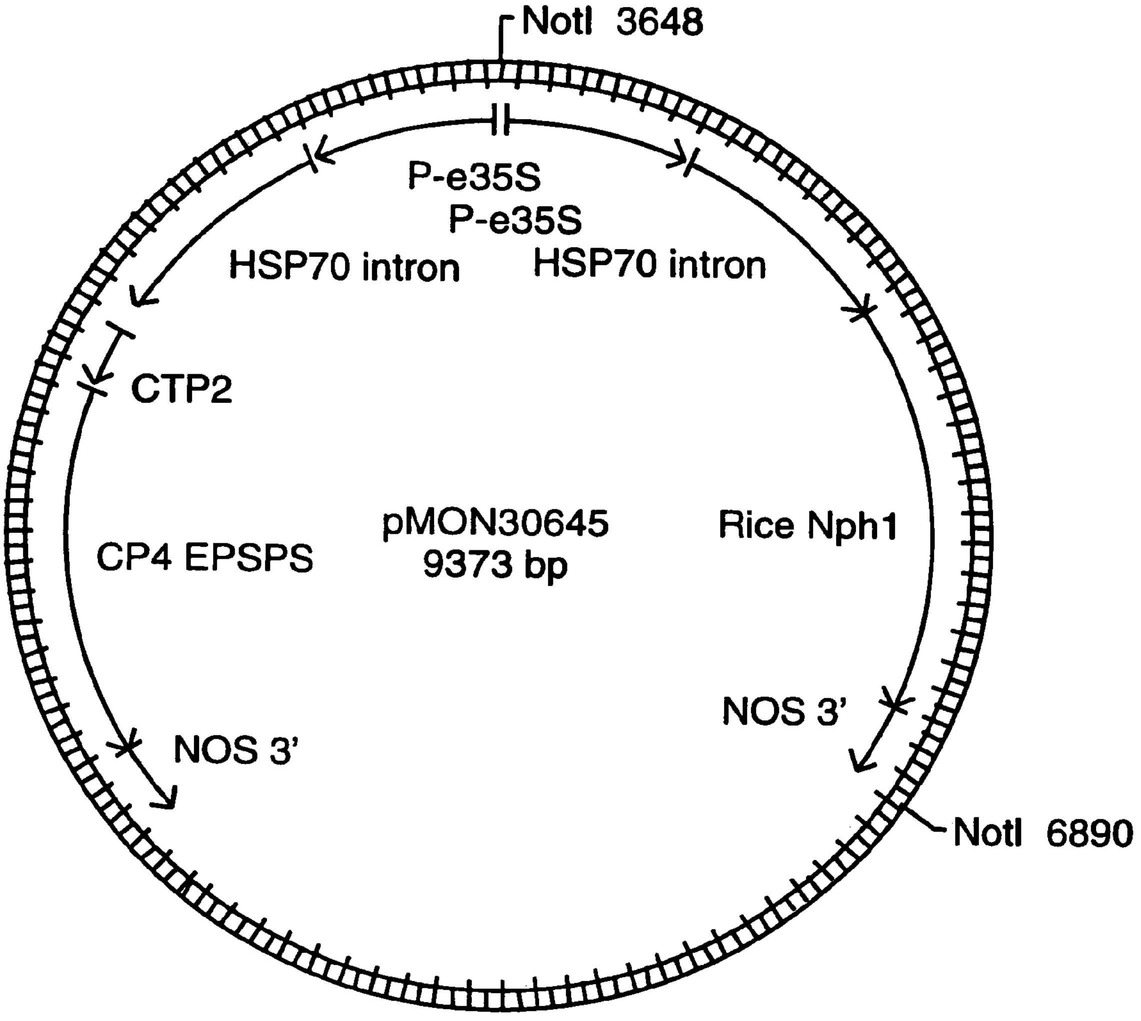
FIG. 11 shows the pMON30645 plasmid used for particle bombardment transformation of rice which contains a rice Nph1 cDNA containing the endogenous rice 5' leader sequence.
Figure 12:
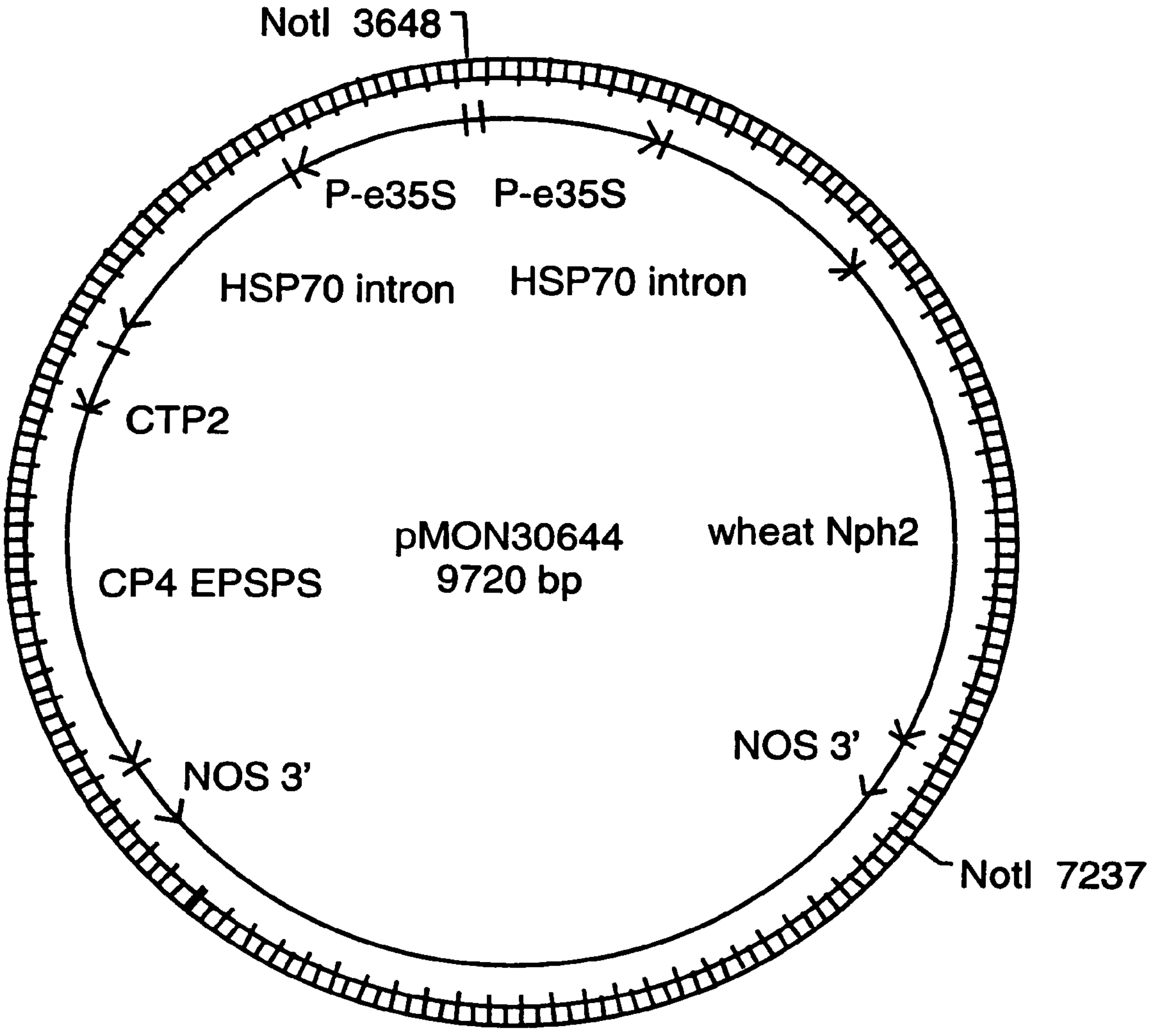
FIG. 12 shows the pMON30644 plasmid used for particle bombardment transformation of rice which contains a wheat Nph2-1 cDNA corresponding to the predicted coding region.

Two constructs were assembled for particle bombardment transformation of rice. The cassette containing the e35S promoter-hsp70 intron-rice Nph1 cDNA (lacking the 5' UTR)-Nos 3' terminator was subcloned as a NotI fragment from pMON30639 shuttle vector into the NotI site of pMON19572. The final plasmid, pMON30645 (FIG. 11), was restriction digested with KpnI and the purified 6754 bp fragment used for particle bombardment of rice embryos. The cassette containing the e35S promoter-hsp70 intron-wheat Nph2-1 cDNA-Nos 3' terminator was subcloned as a NotI fragment from pMON30636 into the NotI site of pMON19572. The final plasmid, pMON30644 (FIG. 12), was restriction digested with PvuII, and the purified 7412 bp fragment used to bombard rice embryos.

Rice was transformed via particle bombardment using the method of Christou et al. (1991) with the elimination of the PEG from the bead preparation step. Selection was performed using the method of Abedinia et al. (1997) except that 1 mM glyphosate was used for 6 weeks. Putative transgenic callus pieces were transferred to MS medium supplemented with 0.1 mg/L IAA, 0.1 mg/L zeatin and 0.02 mM glyphosate and cultured for three weeks at 23° C. under lights. Small green shoots were transferred to medium containing 1/2 MS salts, MS vitamins, 100 mg Myo-inositol, 60 gm/L sucrose, 0.5 mg/L IBA and 0.02 mM glyphosate added post autoclaving. Shoots were cultured for 2 weeks under lights at 23° C.

Transformation of Wheat

Figure 13:
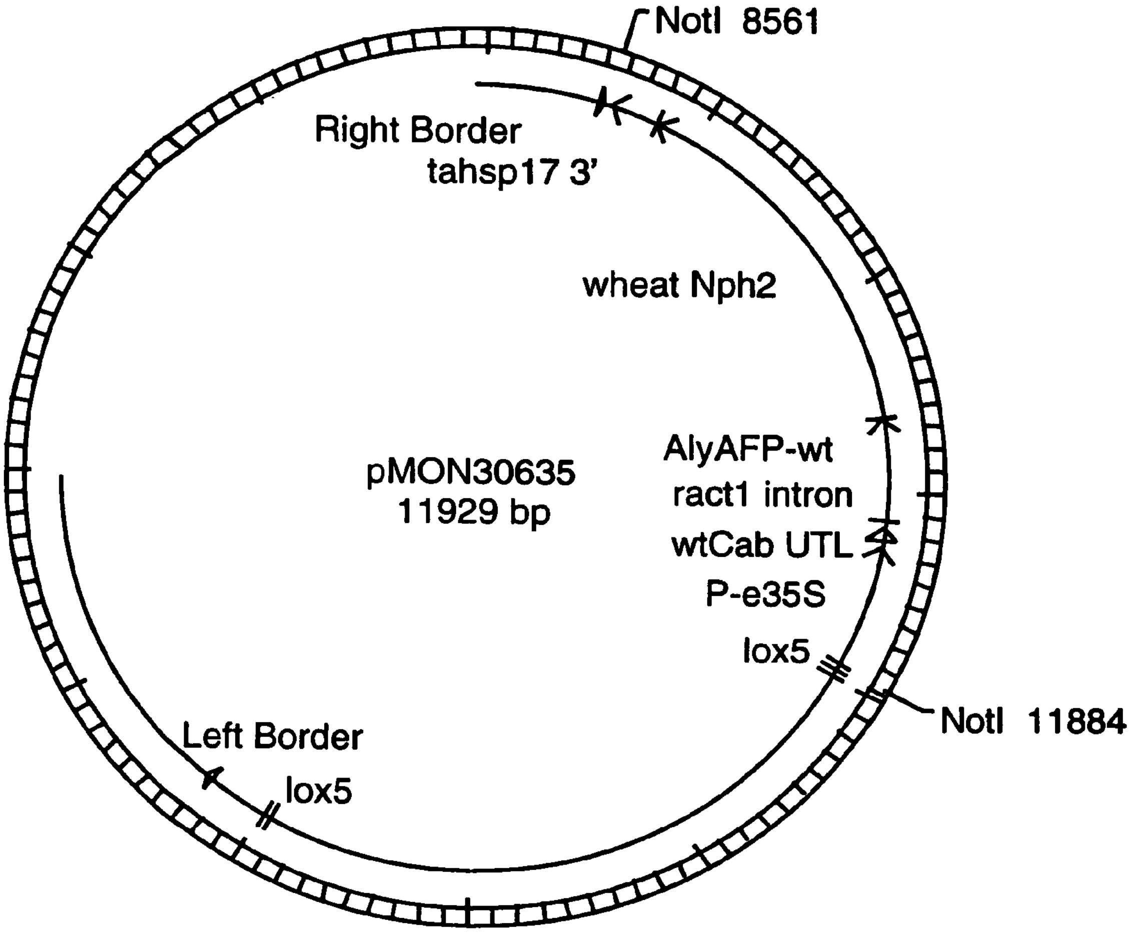
FIG. 13 shows the pMON30635 plasmid for wheat transformation which contains a wheat Nph2-1 coding sequence.

For transformation of wheat plants, the modified Nph2-1 cDNA in pBluscript described above was digested with NcoI/EcoRI and the 1.8 kb fragment subcloned into a shuttle vector (pMON32635) at the corresponding NcoI/EcoRI sites. This created a cassette containing the e35S promoter-CAB leader-rice actin intron-Nph2-1-wheat hsp17 3' terminator. The entire cassette was excised as a NotI restriction fragment and cloned into the corresponding NotI site in the binary vector pMON45119. The final binary for Agrobacterium-mediated transformation of monocots with Nph2-1 is pMON30635 (FIG. 13).

1. Explant Preparation

Immature embryos of wheat (Triticum aestivum L) cv Bobwhite were isolated from the immature caryopsis (wheat spikelets) 13–15 days after pollination, and cultured on CM4C (Table 3) for 3–4 days. The embryos without embryogenic callus were selected for *Agrobacterium* inoculation.

TABLE 3

Supplemental Components in Basal Media[1]

| Components | CM4 | CM4C | MMS.2C | MMS0 |
|---|---|---|---|---|
| 2,4-D (mg/L) | 0.5 | 0.5 | 0.2 | — |
| Pichloram (mg/L)[2] | 2.2 | 2.2 | | |
| Maltose (g/L) | 40.0 | 40.0 | 40.0 | 40.0 |
| Glutamine (g/L) | 0.5 | 0.5 | | |
| $MgCl_2$ (g/L) | 0.75 | 0.7 | | |
| Casein Hydrolysate (g/L) | | 0.1 | 0.1 | |
| MES (g/L) | | 1.95 | 1.95 | 1.95 |
| Ascorbic Acid (mg/L)[2] | | 100.0 | 100.0 | 100.0 |
| Gelling Agent (g/L)[3] | 2 (P) | 2 (P) | 2 (G) | 2 (G) |

[1]All media contain basal salts (MS basal salts) and vitamins (MS vitamins) from Murashige and Skoog (1962). The pH in each medium was adjusted to 5.8.

[2]Filter-sterilized and added to the medium after autoclaving.

[3]PHYTAGEL (P) (PHYTAGEL is a registered trademark of Sigma Chemical Co., St. Louis, MO) or GELRITE (G) (GELRITE is available from Schweizerhall, Inc., South Plainfield NJ) (GELRITE is a registered trademark of Monsanto Company, St. Louis, MO).

2. *Agrobacterium* Culture and Inoculation

A disarmed *Agrobacterium* strain C58 (ABI) harboring a binary. vector was used for all the experiments. Cultures of *Agrobacterium* were initiated from glycerol stocks or from a freshly streaked plate and grown overnight at 26° C.–28° C. with shaking (approximately 150 rpm) to mid-log phase (about $OD_{660}$=1–1.5) in liquid LB medium, pH 7.0 (Miller, 1972) containing 50 mg/L kanamycin, 50 mg/L streptomycin and spectinomycin, and 25 mg/L chloramphenicol with 200 μM acetosyringone (AS). The *Agrobacterium* cells were resuspended in the inoculation medium and the density was adjusted to an $OD_{660}$ of 1. The immature embryos cultured in CM4C medium were transferred into sterile petri plates (16×20 mm) or wells of a 6-well cell culture plate (Costar Corporation, Cambridge, Mass.) containing 10 mL of inoculation medium per petri plate or 5 mL per cell culture cluster plate. An equal amount of the *Agrobacterium* cell suspension was added such that the final concentration of *Agrobacterium* cells was an $OD_{600}$ of 0.5 or in some experiments 0.25. In most experiments, pluronic F68 was added to the inoculation mixture at a final concentration of 0.01%. The ratio between the *Agrobacterium* and immature embryos (IEs) was about 10 mL: 20–200 IEs. The conditions for inoculation were temperatures from 23° C.–26° C. with a duration from 25–30 minutes.

3. Co-Culture

After the inoculation period, the remaining *Agrobacterium* cells were removed from the explants by using the in-house vacuum equipment. A piece of sterile Whatman No. 1 filter paper (to fit the size of the petri plate) was placed in each of 60×15 or 60×20 mm petri dishes. One hundred and seventy-five to one hundred and ninety microliters of sterile water was placed in the middle of the filter paper. After 2–3 minutes, the inoculated immature embryos were placed in the plates. Usually, 20–50 explants are grouped as one stack (about 1 cm in size and 60–80 mg/stack), with 4–5 stacks on each plate. The plates were immediately parafilmed and then co-cultivated in the dark at 24° C.–26° C. for 2–3 days.

4. Selection and Regeneration

After 2–3 days on the delay medium, the immature embryos were transferred to CM4C supplemented with 25 mg/L G418 and 500 mg/L carbenicillin. After 2–3 weeks, the embryos were broken into smaller pieces (~2 mm) and subcultured to the first regeneration medium, MMS.2C (Table 2) with 25 mg/L G418 and 250 mg/L carbenicillin. Upon transfer to the regeneration medium, each piece of callus was further divided into several small pieces (~2 mm). Two weeks post-transfer, young shoots and viable callus tissue were transferred to a second regeneration medium MMSOC (Table 2) with the same concentrations of G418 and carbenicillin. Larger pieces of tissues were separated into smaller pieces as previously described. Plantlets, which were confirmed later to be true transformants, grew vigorously and formed strong root systems on this medium. The plants with strong root hairs, with more than ten short and strong roots, or secondary roots, were transferred to Sundae cups (Sweetheart Cup Company, Chicago, Ill.) containing the second regeneration medium for further growth and selection. During the growth period in the Sundae cups, most of the non-transformants died or showed signs of susceptibility to G418. The plants highly resistant to G418, which grew vigorously with strong root systems, were transferred to soil before they grew to the top of the Sundae cups. All the plants that originated from the same embryo were considered to be siblings from the same event.

5. Detection and Analysis of the Transgenic Plants

The plants were grown in an environmentally controlled growth chamber with a 16-hour photoperiod at 800 $molm^{-2} s^{-1}$ provided by high-intensity discharge (HID) Sylvania lights (GTE Products Corp., Manchester, N.H.). The day/night temperatures were 18/16° C. It took about 2.5 to 3 months from inoculation to transferring most of the plants to soil, and no visible abnormalities were observed. Each plant is tested for acquired resistance genes as described below.

Example 11

Analysis of Transgenic Wheat Carrying the Nph2-1 transgene

*Agrobacterium*-mediated transformation of Nph2-1 (pMON30635) into the wheat cultivar "Bobwhite" yielded 51 independent transgenic lines. RNA gel blot analysis of R0 plants revealed a range of transgene expression, with 36 lines expressing Nph2-1 at low levels (below or similar to control plants), six plants contained relative transcript levels 2 to 5-fold higher, and nine lines contained levels that were at least 5-fold above non-transformed controls. To determine the number of T-DNA loci genetically, thirteen randomly chosen R0 plants, representing a range of expression levels, were grown to maturity for the isolation of R1 seed. About 40 R1 seed per R0 plant were germinated and grown to the 3-leaf stage. These R1 seedlings were sprayed with paramomycin to assay for expression of the NPTII gene. In all 14 cases analyzed, a 3:1 (resistant: sensitive) segregation of paramomycin resistance was observed in the R1 families, indicating that the T-DNAs had integrated at single loci.

Inoculation tests using the powdery mildew fungus (*Erysiphe graminis* pv. *tritici*) were conducted on nine of the aforementioned R1 families. Each family contained twenty-four paramomycin resistant R1 plants which were grown to the 3-week stage. Both these transgenic plants and untransformed controls were infected with *E. g. tritici* and rated for disease symptoms after 11 days. In this test, none of the transgenic lines displayed an increased level of resistance compared to control plants. In fact, seven of nine lines displayed a slightly enhanced disease susceptibility ($P<0.05$). On average, the relative severity of disease symptoms was about 10% higher in transgenic lines than in controls. Unlike the case with NPR1 in Arabidopsis, overexpression of Nph2-1 does not appear to promote disease resistance in wheat.

To determine the level of resistance potentially induced in transgenic lines after chemical activation of SAR, four RI populations were each divided into two groups of 12 plants; one group was INA treated and the second group mock-treated. After three days, each subgroup was disease tested with *E. g. tritici* as described above. After INA treatment of control, non-transgenic Bobwhite plants, disease symptoms were reduced 25% relative to mock-treated plants. This level of disease reduction caused by INA spray treatment is consistent test to test under our assay conditions. However, no significant symptom reductions were observed in any of the four transgenic populations after INA induction. In all cases, the treated and mock-treated control subpopulations showed no enhanced pathogen resistance, with disease severity comparable to untreated Bobwhite controls. These results indicate that transgenic wheat plants containing Nph2-1 are impaired in their systemically acquired resistance responses.

Example 12

Analysis of Transgenic Rice for Enhanced Resistance

As described in Example 10, different binary constructs have been introduced into rice (cv. M202) and the resulting transgenic plants analyzed molecularly and by disease testing (Table 4).

TABLE 4

Summary of transgenic constructs and disease analysis

| pMON | elements | R0 lines (Agro/Gun) | disease resistant lines |
|---|---|---|---|
| 30640 | e35S-Nph1-nos 3' | Agro: 58 lines | 12536 |
| 30643 | e35S-5' UTR-Nph1-nos 3' | Agro: 22 lines | 13943, 13948, 13949, 13950, 13954 |
| 30644 | e35S-Nph1-nos 3' | Gun: 48 lines | 15008, 15011, 15038, 15050, 15110, 15122, 15146, 15383, 15470 |
| 30645 | e35S-Npw2-1-nos 3' | Gun: 44 lines | 15191, 15233, 15263, 15308 |

Each transgenic population was screened for NptII expression and for expression of the Nph1 protein (ELISA and/or western blot analysis). Selected R0 lines were also assessed by RNA blot analysis for altered Nph1 transcript levels. For a subset of low, medium, and high expressing lines, the R0 plants were selfed and resulting R1 populations assayed for disease resistance, Nph1 transcript level, and Nph1 protein accumulation.

For pMON30640, 58 independent R0 lines were generated by Agrobacterium transformation. Plants were screened by ELISA, resulting in 9 high, 8 moderate, and 41 low expressing lines (high=2.5 fold or higher above control; medium=1.5–2.5 fold above control; low=1.0–1.5 fold of control). Of these, 19 lines (6 high expressing lines, 5 medium, and 7 low expressing lines) were selfed and the R1 populations screened for disease resistance against *Magnaporthe grisea*, casual agent of rice blast disease. Of the 19 populations tested, only one line (12536) showed enhanced resistance among the R1 segregants (6 resistant: 14 susceptible). The line 12536 resistance response appears as pinpoint specks of cell death after pathogen challenge, resembling the phenotype of INA-induced, resistant rice. No spreading necrosis is seen and plants remain healthy. Western blot analysis of the 12536 R1 segregants showed segregation of Nph1 protein levels, with a cross-hybridizing band equal to or significantly more intense than the recognized protein band from control plants. For pMON30643, 22 independent lines were generated, all of which yielded R0 plants that had low levels of Nph1 protein accumulation. In contrast to the pMON30640 construct, these lines showed only modest boosts in protein expression with 15/22 being identical to control plants, and the remaining 7/22 at 1.1 fold to 1.4 fold higher than controls. Sixteen R0 plants were selfed to generate R1 populations for disease screening. Among these 16 R1 populations, 5 lines contained blast resistant segregants.

In addition, 92 R0 rice transgenic lines generated by DNA particle gun bombardment using one of two different constructs. Forty-eight lines were generated using the rice construct, pMON30644, while 44 lines were generated using the wheat Nph2-1 construct pMON30645. From the pMON30644 construct, which would be equivalent to the pMON30640, we see 10/44 R0 lines that show enhanced resistance. Of the 44 lines carrying the wheat Nph2-1 gene (pMON30645), we identified 4 independent resistant lines. As noted above, resistance among these transgenics appeared phenotypically similar to that induced by the chemical INA, appearing as restricted, pinpoint lesions at the sites of fungal infection. Unlike the spreading disease lesions noted in susceptible interactions, these specks of necrosis never increased in size and fungal spore production was dramatically limited. These results suggest that both wheat and rice Npr homologs, when expressed in rice, enhance the SAR pathway.

Transgenic overexpression of Nph1 and Nph2-1 promotes strong resistance against *M. grisea*, similar to that noted with INA induction and should also improve rice tolerance to abiotic stress, such as heat, drought, and cold, and plant vigor will be enhanced by the Nph1 or Nph2 transgenic expression.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

REFERENCES

Abedinia et al., *Aust. J. Plant Physiol.,* 24: 133–141, 1997.

Ainley et al., *Plant Mol. Biol.* 14: 949, 1990.

Ali et al., *Mol. Cell Biol.* 18: 4949–4960, 1998.

Ausubel et al., PCT publication, WO98/06748, 1998

Ausubel et al., *Current Protocols in Molecular Biology*, John Wiley and Sons, Inc., 1995.

Back et al., *Plant Mol. Biol.* 17: 9, 1991.

Baker et al., *Science* 276: 726–733, 1997.

Bauer et al., *Gene,* 37: 73, 1985.

Bol et al., *Ann. Rev. Phytophathol,* 28: 13–138, 1990.

Bowles, Ann. Rev. Biochem, 59: 873–907, 1990.

Bull et al., *Mol. Plant-Microbe Interact.,* 5(6):516–519, 1992.

Bustos et al., *EMBO J.* 10: 1469–1479, 1991.

Cameron et al., *Plant J.* 5:715–725, 1994.

Campbell et al., *Plant Physiol.,* 92: 1–11, 1990.

Cao et al., *Plant Cell* 6: 1583–1592, 1994.

Cao et al., *Cell* 88:57–63, 1997.

Cao et al., *Proc. Natl. Acad. Sci. USA* 95: 6531–6536, 1998.

Capecchi, *Cell,* 22(2): 479–488, 1980.

Castresana et al., *EMBO J.* 7: 1929–1936, 1988.

Cerda-Olmedo et al., *J. Mol. Biol.* 33: 705–719, 1968

Chau et al., *Science,* 244:174–181. 1989.

Christensen et al., *Plant Mol. Biol.,* 18: 675,689, 1992.

Christou et al., *Biotechnology,* 9:957–962, 1991.

Clapp, *Clin. Perinatol.,* 20(1): 155–168, 1993.

Costa et al., *Methods Mol. Biol.* 57: 31–44, 1996

Craik, *BioTechniques,* 3: 12–19, 1985.

Curiel et al., *Hum. Gen. Ther.,* 3(2):147–154, 1992.

Cuypers et al., *Mol. Plant-Microbe Interact,* 1: 157–160, 1988.

Delaney et al., *Proc. Natl. Acad. Sci. USA* 92: 6602–6606, 1995.

Deng and Nickloff, Anal. Biochem. 200: 81, 1992.

Dixon et al., *Annu. Rev. Phytopathol.* 32: 479–501, 1994.

Doyle et al., *J. Biol. Chem.* 261: 9228–9238, 1986

Eglitis and Anderson, *Biotechniques,* 6(7): 608–614, 1988.

Feinbaum et al., *Mol. Gen. Genet.* 226: 449–456, 1991

Fraley et al., *Proc. Natl. Acad. Sci. U.S.A.,* 80: 4803, 1983.

Frits Eckstein et al., Nucleic Acids Research, 10: 6487–6497, 1982.

Fritzemeier et al., *Plant Physiol.,* 85: 34–41, 1987.

Fromm et al., *Proc. Natl. Acad. Sci. USA,* 82(17): 5824–5828, 1985.

Fynan et al., *Proc. Natl. Acad. Sci. USA,* 90(24): 11478–11482, 1993.

Glick et al., Methods in Plant Molecular Biology and Biotechnology, CRC Press, Boca Raton, Fla., 1993.

Gorlach et al., *Plant Cell,* 8: 629–643, 1996.

Graham and Van der Eb, *Virology,* 54(2): 536–539, 1973.

Greenberg, *Annu. Rev. Plant Physiol. Plant Mol. Biol.* 48: 525–545, 1997.

Greener et al., *Mol. Biotechnol.* 7: 189–195, 1997.

Guerola et al., *Nature New Biol.* 230: 122–125, 1971

Hames and Higgins, *Nucleic Acid Hybridization: A Practical Approach*, IRL Press Limited, Oxford, Wash. DC, 1985.

Hershey and Stoner, *Plant Mol. Biol.* 17: 679–690, 1991

Hess, *Intern Rev. Cytol.,* 107: 367, 1987.

Horsch et al., *Science,* 227: 1229–1231, 1985.

Hwang and Heitefuss, *Phytopath. Z.,* 103: 41–47, 1982.

Jin et al., *Physiol. Mol. Plant Pathol.* 51: 243–257, 1997.

Johnston and Tang, *Methods Cell Biol.,* 43(A): 353–365, 1994.

Kares et al., *Plant Mol. Biol.* 15: 905, 1990.

Keen, *Annu. Rev. Genet.,* 24: 447–463, 1990.

Keller et al., *EMBO J.,* 8: 1309–1314, 1989.

Kessmann et al., *Annu. Rev. Phytopathol.,* 32: 439–459, 1994.

Kmecl et al., *Physiol. Mol. Plant Pathol.,* 47: 185–199, 1995.

Knutzon et al., *Proc. Natl. Acad. Sci U.S.A.* 89: 2624–2628, 1992.

Kogel et al., *Plant Physiol.,* 106: 1269–1277, 1994.

Kridl et al., *Seed Sci. Res.* 1: 209, 1991.

Kuhlemeier et al., *Plant Cell* 1: 471, 1989.

Kunkel, *Proc. Natl. Acad. Sci. U.S.A.,* 82: 488–492, 1985.

Kyte and Doolittle, *J. Mol. Biol.,* 157: 105–132, 1982.

Lam and Chua, *J. Biol. Chem.* 266: 17131–17135, 1990

Lam and Chua, *Science* 248: 471, 1991

Linthorst, *Crit. Rev. Plant Sci.,* 10: 123–150, 1991.

Logemann et al., *Plant Cell,* 1: 151–158, 1989.

Lu et al., *J. Exp. Med.,* 178(6): 2089–2096, 1993.

Luo et al., *Plant Mol Biol. Reporter,* 6; 165, 1988.

Manandhar et al., *Phytopathol.,* 88: 735–739, 1998.

Mandel et al., *Plant Mol. Biol,* 29: 995–1004, 1995.

Marrs et al., *Dev. Genet.* 14: 27–41, 1993.

Martini et al., *Mol. Gen. Genet.,* 263: 179, 1993.

Matton et al., *Mol. Plant-Microbe Interact,* 2: 325–331, 1989.

Mauch et al., *Plant Mol. Biol.,* 38(4):577–586, 1998.

McElroy et al., *Plant Cell,* 2:163–171, 1990.

Morris et al., *Mol. Plant Microbe Interact.* 11: 643–658, 1998.

Mursahige and Skoog, *Physiol. Plant,* 15:473–497, 1962.

Newell et al., *Plant Cell Rep.,* 10(1):30–34, 1991.

Neuhaus et al., *Theor. Appl. Genet.,* 75: 30, 1987.

Odell et al., *Nature,* 313: 810, 1985.

Osuna et al., *Critical Reviews In Microbiology,* 20: 107–116, 1994.

Ou-Lee et al., *Proc. Natl. Acad. Sci U.S.A.* 83: 6815, 1986.

Pena et al., *Nature,* 325: 274, 1987.

Poszkowski et al., *EMBO J.,* 3: 2719, 1989.

Potrykus et al., *Ann. Rev. Plant Physiol. Plant Mol. Biol.,* 42: 205, 1991.

Pyee et al., *Plant J.,* 7: 49–59, 1995.

Richins et al., *Nucleic Acids Res.* 20: 8451, 1987.

Rodriguez et al., Vectors: A Survey of Molecular Cloning Vectors and Their Uses, Butterworths, Boston, 1988.

Rogan and Bessman, *J. Bacteriol.* 103: 622–633, 1970.

Rogers et al., *Meth. In Enzymol,* 153: 253–277, 1987.

Ryals et al., *Plant Cell,* 8: 1809–1819, 1996.

Ryals et al., *Plant Cell* 9: 425–439, 1997.

Samac et al., *Plant Cell,* 3:1063–1072, 1991.

Sambrook et al., *Molecular Cloning: A Laboratory Manual*, Second Edition, Cold Spring Harbor Laboratory Press, Cold Spring Harbor, N.Y., 1989.

Schaffrath et al., Physiol. Mol. Plant Pathol., 46: 293–307, 1995.

Schaffrath et al., Mol. Plant Microbe Interact., 6: 779–783, 1997.

Schroder et al., *Plant J.,* 2: 161–172, 1992.

Schulze-Lefert et al., *EMBO J.* 8: 651, 1989.

Schweizer et al., *Plant Mol. Biol.,* 12: 451–461, 1989.

Sears, *Chromosome Manipulations and Plant Genetics*, Oliver and Boyd, London, 1966.

Simpson, *Science,* 233: 34, 1986.

Singer and Kusmierek, *Ann. Rev. Biochem.* 52: 655–693, 1982

Slighton and Beachy, *Planta* 172: 356, 1987.

Smith and Metraux, *Physiol. Mol. Plant Pathol.,* 39: 451–461, 1991.

Smith et al., *In: Genetic Engineering: Principles and Methods*, Setlow et al., Eds., Plenum Press, N.Y., 1–32, 1981.

Stayton et al., *Aust. J. Plant. Physiol.* 18: 507, 1991.

Sticher et al., *Annu. Rev. Phytopathol.* 35: 235–270, 1997.

Vandeyar et al., *Gene* 65: 129–133, 1988

Van Tunen et al., *EMBO J.* 7: 1257, 1988.

Vodkin et al., *Cell* 34: 1023, 1983.

Vogel et al., *J. Cell Biochem.*, (Suppl) 13D: 312, 1989.

Wagner et al., *Proc. Natl. Acad. Sci. USA,* 89(13): 6099–6103, 1992.

Walder et al., *Gene,* 42:133, 1986.

Warner et al., *Plant J.* 6: 31–34, 1994.

Waspi et al., *Mol. Plant Microbe Interact.* 11: 727–733, 1998.

Watanabe et al., *J. Pestic. Sci.,* 4: 53–59, 1979.

Weissbach and Weissbach, *Methods for Plant Molecular Biology*, (Eds.), Academic Press, Inc., San Diego, Calif., 1988.

Weisshaar et al., *EMBO J.* 10: 1777–1786, 1991.

Wenzler et al., *Plant Mol. Biol.,* 12: 41–50, 1989.

Williams et al., *Biotechnology* 10: 540–543, 1992.

Wong and Neumann, *Biochim. Biophys. Res. Commun.,* 107(2): 584–587, 1982.

Worthington and Walker, *The Pesticide Manual*, Seventh Edition, British Crop Protection Council, 1983.

Yabe et al., *Plant Cell Physiol.* 35: 1207–1219, 1994.

Yamaguchi-Shinozaki et al., *Plant Mol. Biol.* 15: 905, 1990.

Yang and Russell, *Proc. Natl. Acad. Sci. USA,* 87:4144–4148, 1990.

Zatloukal et al., *Ann. N.Y. Acad. Sci.,* 660: 136–153, 1992.

Zhou et al., *Methods in Enzymology,* 101: 433, 1983.

Although the invention has been described in detail for the purpose of illustration, it is understood that such detail is solely for that purpose, and variations can be made therein by those skilled in the art without departing from the spirit and scope of the invention which is defined by the claims.

What is claimed is:

1. An isolated nucleic acid sequence that encodes a polypeptide comprising the amino acid sequence as set forth in SEQ ID NO:10.

2. the nucleic acid sequence of claim 1 further defined as an RNA sequence.

3. A recombinant vector comprising the nucleotide sequence of SEQ ID NO:5.

4. The recombinant vector of claim 3 wherein said nucleotide sequence is operatively linked to a plant functional promoter and said promoter expresses the polypeptide sequence as set forth in SEQ ID NO:10 from said nucleotide sequence.

5. The recombinant vector of claim 4, wherein the promoter is selected from the group consisting of: constitutive promoters, tissue-specific promoters, and inducible promoters.

6. A transgenic plant having incorporated into its genome a nucleotide sequence that encodes the acquired resistance polypeptide as set forth in SEQ ID NO:10.

7. The transgenic plant of claim 6 wherein the polypeptide is encoded by the nucleotide sequence as set forth in SEQ ID NO:5.

8. Progeny or seed of the plant of claim 6 comprising said nucleotide sequence.

* * * * *